United States Patent
Thiele

(10) Patent No.: US 9,586,980 B2
(45) Date of Patent: Mar. 7, 2017

(54) SILANE SULFIDE MODIFIED ELASTOMERIC POLYMERS

(75) Inventor: Sven Thiele, Halle (DE)

(73) Assignee: TRINSEO EUROPE GMBH, Horgen (CH)

( * ) Notice: Subject to any disclaimer, the term of this patent is extended or adjusted under 35 U.S.C. 154(b) by 0 days.

(21) Appl. No.: 14/427,025

(22) PCT Filed: Sep. 14, 2012

(86) PCT No.: PCT/EP2012/068120
§ 371 (c)(1),
(2), (4) Date: Apr. 8, 2015

(87) PCT Pub. No.: WO2014/040639
PCT Pub. Date: Mar. 20, 2014

(65) Prior Publication Data
US 2015/0322098 A1    Nov. 12, 2015

(51) Int. Cl.
| | | |
|---|---|---|
| *C08F 8/34* | (2006.01) | |
| *C08F 8/42* | (2006.01) | |
| *C07F 7/18* | (2006.01) | |
| *C07F 7/22* | (2006.01) | |
| *C08F 236/10* | (2006.01) | |
| *C08K 3/04* | (2006.01) | |
| *C08K 3/36* | (2006.01) | |
| *C08J 3/24* | (2006.01) | |

(52) U.S. Cl.
CPC ............ *C07F 7/2268* (2013.01); *C07F 7/184* (2013.01); *C07F 7/1836* (2013.01); *C07F 7/2264* (2013.01); *C08F 236/10* (2013.01); *C08J 3/24* (2013.01); *C08K 3/04* (2013.01); *C08K 3/36* (2013.01); *C08J 2347/00* (2013.01); *C08K 2003/045* (2013.01)

(58) Field of Classification Search
CPC .. C08F 8/34; C08F 8/42; C07F 7/0898; C07F 7/18
See application file for complete search history.

(56) References Cited

U.S. PATENT DOCUMENTS

| | | | |
|---|---|---|---|
| 6,893,495 B2 * | 5/2005 | Korth | C08K 9/06 106/481 |
| 2004/0266968 A1 | 12/2004 | Korth et al. | |
| 2007/0203274 A1 | 8/2007 | Korth et al. | |
| 2008/0287601 A1 * | 11/2008 | Thiele | B60C 1/0016 524/588 |

FOREIGN PATENT DOCUMENTS

CH    WO 9828256 A1 *   7/1998   ......... B01J 31/0228

* cited by examiner

*Primary Examiner* — Brieann R Fink
(74) *Attorney, Agent, or Firm* — Eric D. Babych; Brinks Gilson & Lione

(57) ABSTRACT

The present invention relates to silane sulfide modifier compounds and methods of making them. The invention also relates to a silane sulfide modified macromolecular compound obtainable by reacting a living anionic elastomeric polymer and a silane sulfide modifier. The silane sulfide modified macromolecular compound may be provided in the form of a polymer composition, and the polymer composition may be vulcanized (cross-linked) by making use of and reaction with at least one vulcanization agent, resulting in a vulcanized polymer composition.

23 Claims, No Drawings

US 9,586,980 B2

SILANE SULFIDE MODIFIED ELASTOMERIC POLYMERS

This application claims priority to International Application No. PCT/EP2012/068120 filed Sep. 14, 2012, the entire contents of which are incorporated herein by reference.

FIELD OF THE INVENTION

This invention relates to silane sulfide modifier compounds and methods of making them. The invention also relates to a silane sulfide modified macromolecular compound obtainable by reacting a living anionic elastomeric polymer and a silane sulfide modifier. The silane sulfide modified macromolecular compound may be provided in the form of a polymer composition, and the polymer composition may be vulcanized (crosslinked) by making use of and reaction with at least one vulcanization agent, resulting in a vulcanized polymer composition. Finally, the invention also provides an article comprising at least one component formed from (constituted by) the vulcanized polymer composition. The vulcanized polymer composition has relatively low hysteresis loss and is useful in many articles, including tire treads having low heat build up, low rolling resistance, good wet grip and ice grip, in combination with a good balance of other desirable physical and chemical properties, for example, abrasion resistance and tensile strength and excellent processability.

BACKGROUND OF THE INVENTION

It is generally accepted, that increasing oil prices and national legislation demand the reduction of automotive carbon dioxide emissions, thus requesting from tire and rubber producers to produce "fuel efficient" tires. One general approach to obtain fuel efficient tires is to produce tire formulations that have reduced hysteresis loss. A major source of hysteresis in vulcanized elastomeric polymers is attributed to free polymer chain ends, that is, the section of the elastomeric polymer chain between the last cross-link and the end of the polymer chain. This free end of the polymer does not participate in any efficient elastically recoverable process, and as a result, energy transmitted to this section of the polymer is lost. This dissipated energy leads to a pronounced hysteresis under dynamic deformation. Another source of hysteresis in vulcanized elastomeric polymers is attributed to an insufficient distribution of filler particles in the vulcanized elastomeric polymer composition. The hysteresis loss of a cross-linked elastomeric polymer composition is related to its Tan $\delta$ at 60° C. value (see ISO 4664-1:2005; Rubber, Vulcanized or thermoplastic; Determination of dynamic properties—part 1: General guidance). In general, vulcanized elastomeric polymer compositions having relatively small Tan $\delta$ values at 60° C. are preferred as having lower hysteresis loss. In the final tire product, this translates into a lower rolling resistance and better fuel economy.

Furthermore, there are also demands to maintain or improve tire grip properties, particularly the grip of the tire on a wet or icy road. The tire wet and ice grip of a cross-linked elastomeric polymer composition is related to its Tan $\delta$ at 0° C. and Tan $\delta$ at −10° C. values. It is generally accepted that a lower rolling resistance tire can be made on the expense of deteriorated wet grip properties and vice versa. For example, if, in a random solution styrene-butadiene rubber (random SSBR), the polystyrene unit concentration is reduced with respect to the total polybutadiene unit concentration and the 1,2-polydiene unit concentration is kept constant, both tan delta at 60° C. and tan delta at 0° C. are reduced, generally corresponding to improved rolling resistance and deteriorated wet grip performance of a tire. Similarly, if, in a random solution styrene-butadiene rubber (random SSBR), the 1,2-polybutadiene unit concentration is reduced with respect to the total polybutadiene unit concentration and the polystyrene unit concentration is kept constant, both tan delta at 60° C. and tan delta at 0° C. are reduced, generally corresponding to improved rolling resistance and deteriorated wet grip performance of a tire. Accordingly, when assessing the rubber vulcanizate performance correctly, both the rolling resistance, or tan delta at 60° C., and the wet grip, or tan delta at 0° C., should be monitored.

One generally accepted approach to reducing hysteresis loss is to reduce the number of free chain ends of elastomeric polymers. Various techniques are described in the open literature including the use of "coupling agents," such as tin tetrachloride, which may functionalize the polymer chain end, and react with components of an elastomeric composition, such as, for example, with a filler or with unsaturated portions of a polymer. Examples of such techniques, along with other documents of interest, are described in the following patents: U.S. Pat. Nos. 3,281,383; 3,244,664 and 3,692,874 (for example, tetrachlorosilane); U.S. Pat. No. 3,978,103; U.S. Pat. Nos. 4,048,206; 4,474,908; U.S. Pat. No. 6,777,569 (blocked mercaptosilancs) and U.S. Pat. No. 3,078,254 (a multi-halogen-substituted hydrocarbon, such as 1,3,5-tri(bromo methyl) benzene); U.S. Pat. No. 4,616,069 (tin compound and organic amino or amine compound); and U.S. 2005/0124740.

The use of "coupling agents" as reactants to living polymers more often than not leads to the formation of polymer blends comprising one fraction of linear or uncoupled polymers, and one or more fractions comprising more than two polymer arms at the coupling point. The reference "Synthesis of end-functionalized polymer by means of living anionic polymerization," Journal of Macromolecular Chemistry and Physics, 197, (1996), 3135-3148, describes the synthesis of "polystyrene-containing" and "polyisoprene-containing" living polymers with hydroxy (—OH) and mercapto (—SH) functional end caps, obtained by reaction of the living polymers with haloalkanes containing silyl ether and silyl thioether functions. The tertiary-butyldimethylsilyl (TB-DMS) group is preferred as a protecting group for the —OH and —SH functions in the termination reactions, because the corresponding silyl ethers and thioethers are found to be both stable and compatible with anionic living polymers.

WO2007/047943 describes the use of a silane-sulfide omega chain end modifier. A silane sulfide compound is reacted with anionically-initiated, living polymers to produce "chain end modified" polymers, which are subsequently blended with fillers, vulcanizing agents, accelerators or oil extenders, to produce a vulcanized elastomeric polymer composition having low hysteresis loss. To further control polymer molecular weight and polymer properties, a coupling agent (or linking agent) can be used as an optional component in the process of the preparation of elastomeric polymers. The modifier is added before, after or during the addition of a coupling agent, and the modification reaction is preferably completed after the addition of the coupling agent. In some embodiments, more than a third of the polymer chain ends are reacted with a coupling agent prior to addition of the modifier.

WO 2009/148932 describes an elastomeric polymer composition as the reaction product of a living anionic elastomeric polymer with two silane modifier compounds (A) and (B). The silane modifier compound (A) is reported to react with at least two polymer chains, forming branched modified polymer macromolecules, while silane modifier compound (B) is reported to react with only one polymer chain, forming chain-end modified polymer macromolecules. The resulting cured composition comprising branched-modified and chain-end modified polymer macromolecules is stated to result in lower "Tan δ at 60° C." values, without negatively impacting other physical properties, particularly "Tan δ at 0° C."

WO2007/047943 and WO 2009/148932 do not provide rheological information on filler-containing polymer compositions. Yet, it is reasonable to expect higher viscosities as a result of enhanced polymer-filler associations.

Two fillers, silica and carbon black, are typically used in the tire production. Standard formulations very often comprise both fillers in varying ratios. Therefore, it would be desirable to have a modified polymer (comprising one or both of branched modified polymer macromolecules and chain end modified polymer macromolecules) which exhibits reduced viscosity in (non-cured) polymer compositions, especially lower Mooney viscosity, and/or improved rolling resistance/grip balance characteristics of the cured compositions.

SUMMARY OF THE INVENTION

The present invention provides a silane sulfide modifier represented by the following Formula 1:

$$((R^1O)_x(R^2)_ySi-R^3-S)_sM(R^4)_t(X)_u \quad \text{Formula 1}$$

wherein:
M is silicon or tin;
x is an integer selected from 1, 2 and 3;
y is an integer selected from 0, 1, and 2; wherein x+y=3;
s is an integer selected from 2, 3 and 4;
t is an integer selected from 0, 1 and 2;
u is an integer selected from 0, 1 and 2; wherein s+t+u=4;
$R^1$ is independently selected from $(C_1-C_6)$ alkyl;
$R^2$ is independently selected from $(C_1-C_{16})$ alkyl, $(C_7-C_{16})$ alkylaryl and $(C_7-C_{16})$ arylalkyl;
$R^3$ is at least divalent and is independently selected from $(C_1-C_{16})$ alkyl, $(C_8-C_{16})$ alkylarylalkyl, $(C_7-C_{16})$ arylalkyl and $(C_7-C_{16})$ alkylaryl, and each group may be substituted with one or more of the following groups: tertiary amine group, silyl group, $(C_7-C_{18})$ aralkyl group and $(C_6-C_{18})$ aryl group;
$R^4$ is independently selected from $(C_1-C_{16})$ alkyl and $(C_7-C_{16})$ alkylaryl;
X is independently selected from chloride, bromide and $-OR^5$; wherein $R^5$ is selected from $(C_1-C_{16})$ alkyl and $(C_7-C_{16})$ arylalkyl.

The invention furthermore provides a method of making the silane sulfide modifier of Formula 1 as defined above, comprising the steps of
(i) combining
  (ia) a compound of the following Formula 2

$$(R^1O)_x(R^2)_ySi-R^3-SH \quad \text{Formula 2,}$$

wherein $R^1$, $R^2$, $R^3$, x and y are as defined above; and
  (ib) an amine compound selected from the following Formula 3a and Formula 3b $$R^5R^6R^7N \quad \text{Formula 3a}$$

$$R^8R^9N-(CR^{10}R^{11})_v-NR^8R^9 \quad \text{Formula 3b}$$

wherein $R^5$, $R^6$ $R^7$, $R^8$, $R^9$, $R^{10}$ and $R^{11}$ are each independently selected from hydrogen, $(C_1-C_{16})$ alkyl, $(C_7-C_{16})$ alkylaryl; $(C_7-C_{16})$ arylalkyl and $(C_6-C_{16})$ aryl; and v is an integer selected from 1 to 10;
(ii) reacting the mixture resulting from step (i) with a compound of the following Formula 4

$$M(R^4)_t(X)_u \quad \text{Formula 4,}$$

wherein M is silicon or tin, u is an integer selected from 2, 3 and 4; $R^4$, X and t are as defined above; and t+u=4;
in a solvent; and
(iii) optionally isolating the silane sulfide modifier of Formula 1 obtained in step (ii).

The invention provides a further method of making the silane sulfide modifier of Formula 1 as defined above, comprising the steps of
(i) reacting a compound of Formula 2 as defined above and an alkali metal hydride in a solvent,
(ii) reacting the reaction product resulting from step (i) with a compound of Formula 4 as defined above in a solvent; and
(iii) optionally isolating the silane sulfide modifier of Formula 1 obtained in step (ii).

The invention also provides a silane sulfide modified macromolecular compound (also referred to as a silane sulfide modified elastomeric macromolecular compound) obtainable by reacting
i) a living anionic elastomeric polymer and
ii) a silane sulfide modifier represented by Formula 1 as defined above.

The invention further provides a first polymer composition comprising at least one of said silane sulfide modified macromolecular compounds as defined above and one or more further components selected from non-modified elastomeric polymers and elastomeric polymers modified with non-inventive modifiers or coupling agents as described herein. In addition, the first polymer composition may comprise additives such as stabilizing agents or softeners, including oils, as described herein. Usually, the first polymer composition is the result of the polymerization process (reaction) employed to provide the silane sulfide modified macromolecular compound of the present invention and, thus, comprises the modified macromolecular compound and one or more further components selected from components which (i) are added to or formed as a result of the polymerization process and which (ii) remain after solvent removal.

The invention furthermore provides a second polymer composition comprising at least the following:
  (i) the first polymer composition as defined above; and
  (ii) at least one filler.

The invention also provides a vulcanized polymer composition comprising the reaction product of at least the following:
  1) at least one vulcanization agent; and
  2) the first or second polymer composition as defined above.

The vulcanized polymer composition can be produced by reacting the at least one vulcanization agent and the first or second polymer composition as described herein.

The invention also provides an article comprising at least one component formed from the vulcanized polymer composition as defined above.

DETAILED DESCRIPTION OF THE INVENTION

The invention provides a silane sulfide modifier of Formula 1 as defined above.

In a preferred embodiment, M is a silicon atom.

In a preferred embodiment, $R^3$ is divalent and is $(C_1-C_{16})$ alkyl.

In one embodiment, X is —$OR^5$; wherein $R^5$ is selected from $(C_1-C_{16})$ alkyl.

In another embodiment, X is chloride or bromide.

In one preferred embodiment, $R^2$ and $R^4$ are independently selected from $(C_1-C_{16})$ alkyl.

In one preferred embodiment, $R^1$, $R^2$, $R^4$ and $R^5$ are independently selected from $(C_1-C_4)$ alkyl.

In one embodiment, s and t are each 2 and u is 0.

In another embodiment, s is 3, t is 1 and u is 0.

In one embodiment, x is 2 and y is 1.

In another embodiment, x is 1 and y is 2.

The invention furthermore provides a method of making the silane sulfide modifier represented by Formula 1 as defined above, comprising the steps of (i) combining (ia) a compound of Formula 2 as defined above and (ib) an amine compound selected from Formula 3a and Formula 3b as defined above; (ii) reacting the mixture resulting from step (i) with a compound of Formula 4 as defined above in a solvent; and (iii) optionally isolating the silane sulfide modifier of Formula 1 obtained in step (ii).

In a preferred embodiment, $R^3$ is divalent and is $(C_1-C_{16})$ alkyl.

In one embodiment, X is —$OR^5$; wherein $R^5$ is selected from $(C_1-C_{16})$ alkyl.

In another embodiment, X is chloride or bromide.

In one preferred embodiment, $R^2$ and $R^4$ are independently selected from $(C_1-C_{16})$ alkyl.

In one preferred embodiment, $R^1$, $R^2$, $R^4$ and $R^5$ are independently selected from $(C_1-C_4)$ alkyl.

In one embodiment, s and t are each 2 and u is 0 in Formula 1, and u and t are each 2 in Formula 4.

In another embodiment, s is 3, t is 1 and u is 0.

In one embodiment, x is 2 and y is 1.

In another embodiment, x is 1 and y is 2.

In one preferred embodiment, v is selected from an integer of 2.

In one preferred embodiment, $R^5$, $R^6$, $R^7$, $R^8$, $R^9$, $R^{10}$ and $R^{11}$ are independently selected from $(C_1-C_4)$ alkyl.

The invention provides a further method of making the silane sulfide modifier represented by the Formula 1 as defined above, comprising the steps of (i) reacting a compound of Formula 2 as defined above and an alkali metal hydride in a solvent; (ii) reacting the reaction product resulting from step (i) with a compound of Formula 4 as defined above in a solvent; and optionally (iii) isolating the silane sulfide modifier of Formula 1 obtained in step (ii).

In one preferred embodiment, $R^3$ is divalent and is $(C_1-C_{16})$ alkyl.

In one embodiment, X is —$OR^5$; wherein $R^5$ is selected from $(C_1-C_{16})$ alkyl.

In another embodiment, X is chloride or bromide.

In one preferred embodiment, $R^2$ and $R^4$ are independently selected from $(C_1-C_{16})$ alkyl.

In one preferred embodiment, $R^1$, $R^2$, $R^4$ and $R^5$ are independently selected from $(C_1-C_4)$ alkyl.

In one embodiment, s and t are each 2 and u is 0 in Formula 1, and u and t are each 2 in Formula 4.

In another embodiment, s is 3, t is 1 and u is 0.

In one embodiment, x is 2 and y is 1.

In another embodiment, x is 1 and y is 2.

In one preferred embodiment, v is selected from an integer of 2.

In one preferred embodiment, $R^5$, $R^6$, $R^7$, $R^8$, $R^9$, $R^{10}$ and $R^{11}$ are independently selected from $(C_1-C_4)$ alkyl.

In the methods of the invention of making the silane sulfide modifier of Formula 1, the latter compound may be isolated in a respective step (iii) in a conventional manner, for example by separation from the reaction mixture through filtration, evaporation of the solvent or distillation.

The invention also provides a silane sulfide modified macromolecular compound obtainable by reacting:
 i) a living anionic elastomeric polymer and
 ii) a silane sulfide modifier of Formula 1 as defined above in general and preferred embodiments.

In the modification reaction, one or more living polymer chains are modified at their polymer chain end(s) by one silane sulfide modifier. The resulting modified macromolecular compound is not necessarily chain end modified. For example, the reaction of two polymer chains with one silane sulfide modifier may result in a structure of polymer-silane sulfide-polymer.

The invention further provides a first polymer composition comprising at least one of said silane sulfide modified macromolecular compounds as defined above and one or more further components selected from non-modified elastomeric polymers and elastomeric polymers modified with non-inventive modifiers or coupling agents as described herein.

The invention furthermore provides a second polymer composition comprising at least the following:
 (i) the first polymer composition as defined above; and
 (ii) at least one filler.

In one preferred embodiment, the at least one filler is silica.

In another preferred embodiment, the at least one filler is carbon black.

In one embodiment, the second polymer composition further comprises an oil.

In one further embodiment, the second polymer composition comprises a vulcanization agent.

In one embodiment, the second polymer composition is the result of a mechanical mixing process involving the first polymer composition and at least one filler. The second polymer composition typically includes components which are added to the (solvent-free) first polymer composition and which remain in the composition after completion of the mechanical mixing process. Therefore, the specified components contained in the second polymer composition include at least one filler and may, but do not have to include, and are not limited to alternative (solvent-free) modified or non-modified polymers, stabilizers and softeners.

The invention also provides a vulcanized polymer composition comprising the reaction product of at least the following:
 1) at least one vulcanization agent; and
 2) the first or second polymer composition as defined above.

In one preferred embodiment of the vulcanized polymer composition, component 2) is the second polymer composition as described herein.

The invention also provides a method for making a vulcanized polymer composition comprising reacting at least the following components:
 1) at least one vulcanization agent; and
 2) the first or second polymer composition as defined above.

In one preferred embodiment of the method for making the vulcanized polymer composition, component 2) is the second polymer composition as described herein.

The vulcanized polymer composition is the result of a reactive polymer-polymer crosslink forming process which is performed on the first or second polymer composition comprising at least one vulcanization agent. Therefore, the reactive process converts an essentially uncrosslinked elastomeric polymer composition into a crosslinked elastomeric polymer composition, i.e. the vulcanized polymer composition.

The invention also provides an article comprising at least one component formed from the vulcanized polymer composition as defined above. In one embodiment, the article is a tire or tire tread.

The following embodiments apply to all applicable aspects and embodiments described herein.

In one embodiment, the polymer portion of the silane sulfide modified macromolecular compound of the present invention is selected from the group consisting of modified styrene-butadiene copolymers, modified polybutadiene, modified butadiene-isoprene copolymers, modified polyisoprene and modified butadiene-styrene-isoprene terpolymers. In one embodiment, the first or second polymer composition in accordance with the present invention further comprises at least one polymer selected from the group consisting of styrene-butadiene copolymers, including but not limited to solution styrene-butadiene rubber (SSBR) and emulsion styrene-butadiene rubber (ESBR); polybutadiene, including polybutadiene with a 1,4-cis-polybutadiene concentration ranging from 90 to 99 percent, from 30 to 70 percent, or from 2 to 25 percent, based on weight; butadiene-isoprene copolymers; polyisoprene; butadiene-styrene-isoprene terpolymers; and combinations thereof.

The invention encompasses, within its scope, any combinations of two or more specific or preferred features as defined herein, unless such combination is technically or logically excluded.

Polymerization

The living anionic elastomeric polymer used in the present invention is obtained by polymerization of one or more monomers, as is conventionally known in the art. General information about applicable polymerization technologies including polymerization initiator compounds; randomizer agents (also called polar coordinator compounds) and accelerators, each to increase the reactivity of the initiator, to randomly arrange aromatic vinyl compounds, to randomly arrange 1,2-polybutadiene or 1,2-polyisoprene or 3,4-polyisoprene units introduced in the polymer; the amounts of each compound; monomer(s); and suitable process conditions are described in WO 2009/148932 fully incorporated herein by reference. Solution polymerizations normally take place at lower pressures, preferably below 10 MPa, preferably in a temperature range of from 0 to 120° C. The polymerization is generally conducted under batch, continuous or semi-continuous polymerization conditions. The polymerization process is preferably conducted as a solution polymerization, wherein the polymer formed is substantially soluble in the reaction mixture, or as a suspension/slurry polymerization, wherein the polymer formed is substantially insoluble in the reaction medium. Examples of preferred randomizer agents (also called polar coordinator compounds) and of accelerators are listed in WO 2009/148932.

Polymerization Initiator Compounds

The use of ionic initiators, such as lithium initiators, to polymerize conjugated diene, triene, and monovinyl aliphatic and aromatic monomers, and other monomers, is well known (anionic solution polymerization). Such polymerizations proceed according to an anionic polymerization mechanism, wherein the reaction of the monomers is by nucleophilic initiation to form and propagate a polymeric structure. In these polymerizations, the active center is typically a carbon ion with a partial or total negative charge. Throughout the polymerization, the polymer structure is ionic or "living". Thus, the polymer structure has at least one reactive or "living" end. This is the context of the term "living," as used herein, to describe those uncrosslinked elastomeric polymers prepared by an anionic solution polymerization technology. Thus, a living anionic elastomeric polymer is prepared by an anionic polymerization, as discussed herein.

Polymerization of the monomers, as described herein, is, in case of anionic living type polymerization reactions, typically initiated with an anionic initiator, such as, but not limited to, an organo metal compound having at least one lithium, sodium or potassium atom, and where the organo metal compounds contain from 1 to about 20 carbon atoms. Preferably, the organo metal compound has at least one lithium atom, such as ethyl lithium, propyl lithium, n-butyl lithium, sec-butyl lithium, tert-butyl lithium, phenyl lithium, hexyl lithium, 1,4-dilithio-n-butane, 1,3-di(2-lithio-2-hexyl) benzene, and preferably n-butyl lithium and sec-butyl lithium. These organo lithium initiators may be used alone or in combination as a mixture of two or more different kinds. The amount of organo lithium initiator used, varies, based upon the monomers being polymerized and on the target molecular weight of the produced polymer, however, the amount is typically from 0.05 to 5 mmol, preferably from 0.2 to 3 mmol per 100 grams of monomer.

Randomizer Agents

Lewis bases may optionally be added to the polymerization mixture to adjust the microstructure (the content of vinyl bonds) of the conjugated diolefin portion of diolefin-type homo-, co- or terpolymer, or to adjust the composition distribution of the aromatic vinyl compound in the conjugated diene monomer-containing co- or terpolymer, and thus for example to serve as a randomizer component. Lewis bases are, for example, but not limited to, ether compounds, such as diethyl ether, di-n-butyl ether, ethylene glycol diethyl ether, ethylene glycol dibutylether, diethylene glycol dimethyl ether, propylene glycol dimethyl ether, propylene glycol diethyl ether, propylene glycol dibutylether, alkyltetrahydroforylethers, such as, methyltetrahydrofurylether, ethyltetrahydrofurylether, propyltetrahydrofurylether, butyltetrahydrofurylether, hexyltetrahydrofurylether, octyltetrahydrofurylether, tetrahydrofuran, 2,2-(bistetrahydrofurfuryl)propane, bistetrahydrofurfurylformal, methyl ether of tetrahydrofurfuryl alcohol, ethyl ether of tetrahydrofurfuryl alcohol, butyl ether of tetrahydrofurfuryl alcohol, α-methoxytetrahydrofuran, dimethoxybenzene and dimethoxyethane, and tertiary amine compounds, such as butyl ether of triethylamine, pyridine, N,N,N',N'-tetramethyl ethylenediamine, dipiperidinoethane, methyl ether of N,N-diethylethanolamine, ethyl ether of N,N-diethylethanolamine and N,N-diethylethanolamine.

Coupling Agents

Coupling agents include tin tetrachloride, tin tetrabromide, tin tetrafluoride, tin tetraiodide, silicon tetrachloride, silicon tetrabromide, silicon tetrafluoride, silicon tetraiodide, alkyl tin and alkyl silicon trihalides or dialkyl tin and dialkyl silicon dihalides. Polymers coupled with tin or silicon tetrahalides have a maximum of four arms, polymers coupled with alkyl tin and alkyl silicon trihalides have a maximum of three arms, and polymers coupled with dialkyl tin and dialkyl silicon dihalides have a maximum of two arms. Hexahalo disilanes or hexahalo disiloxanes can also be used as coupling agents resulting in polymers with a maximum of six arms. Useful tin and silicon halides coupling agents include: $SnCl_4$, $(R_1)SnCl_2$, $R_1SnCl_3$, $SiCl_4$, $(R_1)_2SiCl_2$, $R_1SiCl_3$, $Cl_3Si—SiCl_3$, $Cl_3Si—O—SiCl_3$, $Cl_3Sn—SnCl_3$ and $Cl_3Sn-O-SnCl_3$ wherein $R_1$ is a hydrocarbyl group, preferably an alkyl group. Examples of tin and silicon alkoxides coupling agents further include: $Sn(OMe)_4$, $Si(OMe)_4$, $Sn(OEt)_4$ and $Si(OEt)_4$. The most preferred coupling agents are: $SnCl_4$, $SiCl_4$, $Sn(OMe)_4$ and $Si(OMe)_4$.

The coupling agents may be added intermittently (or at regular or irregular intervals) or continuously during the polymerization, but are preferably added at a conversion rate of the polymerization of more than 80 percent, and more preferably at a conversion rate of more than 90 percent.

For example, a coupling agent can be continuously added during the polymerization, in cases where asymmetrical coupling is desired. This continuous addition is normally done in a reaction zone separate from the zone where the bulk of the polymerization is occurring. The coupling agent can be added in a hydrocarbon solution, for example, in cyclohexane, to the polymerization admixture, with suitable mixing for distribution and reaction. The coupling agent will typically be added only after a high degree of conversion has already been attained. For instance, the coupling agent will normally be added only after a monomer conversion of greater than about 80 percent has been realized. It will typically be preferred for the monomer conversion to reach at least about 90 percent before the coupling agent is added. Polymers coupled with coupling agents have a minimum of two polymer chain arms.

In one embodiment, a substantial amount of the living polymer chain ends is not terminated with termination agents (i.e. water, alcohols, inorganic or organic acids, such as hydrochloric acid, sulfuric acid and carboxylic acids, preferably alcohols or water) or is not reacted with the silane sulfide modifier of the present invention prior to the reaction with the coupling agent. That is, living polymer chain ends are present and capable of reacting with the coupling agent in a polymer chain coupling reaction. The coupling agent mediated coupling reaction occurs before, after or during the addition of the silane sulfide modifier. Preferably, the coupling agent mediated coupling reaction is completed prior to the addition of the silane sulfide modifier. In one embodiment, as result of the coupling reaction, 80 percent or less of the living polymer chains, as determined by GPC, are reacted with the coupling agent. Preferably 65 percent or less of the polymer chains are reacted with the coupling agent, and more preferably 50 percent or less of the polymer chains are reacted with the coupling agent.

In some preferred embodiments, between 10 and 30 percent of the living polymer chain ends, as determined by GPC, are reacted with coupling agent(s), prior to the addition of the silane sulfide modification agent. In other embodiments, between 20 and 35 percent of the living polymer chain ends are reacted with coupling agent(s), prior to the addition of the silane sulfide modifier. In yet other embodiment, between 35 and 50 percent of the living polymer chain ends are reacted with coupling agent(s), prior to the addition of the silane sulfide modifier. The coupling agent may be directly added into the polymer solution without dilution; however, it may be beneficial to provide addition of the coupling agent in solution, such as in an inert solvent (for example, cyclohexane). For instance, if different types of coupling agents are used, from 0.01 to 2.0 mol, preferably from 0.02 to 1.5 mol, and more preferably from 0.04 to 0.6 mol, of the coupling agent is utilized for every 4.0 moles of living and thus anionic polymer chain ends.

A combination of a coupling agent comprising tin or silicon, as described before, can optionally be used to couple the polymer. A combination of different coupling agents, such as $Bu_2SnCl_2$ and $SnCl_4$; $Me_2SiCl_2$ and $Si(OMe)_4$; $Me_2SiCl_2$ and $SiCl_4$; $SnCl_4$ and $Si(OMe)_4$; $SnCl_4$ and $SiCl_4$ can also be used to couple polymer chains. It is particularly desirable to utilize a combination of tin and silicon coupling agents in tire tread compounds that contain both silica and carbon black. In such cases, the molar ratio of the tin to the silicon compound employed for coupling the elastomeric polymer will normally be within the range of from 20:80 to 95:5; more typically from 40:60 to 90:10, and preferably from 60:40 to 85:15. Most typically, a range of from about 0.001 to 4.5 mmol of coupling agent (tin and silicon compound, silicon coupling agents) is employed per 100 grams of the elastomeric polymer. It is normally preferred to utilize from about 0.05 to about 0.5 mmol of the coupling agent per 100 grams of polymer to obtain the desired Mooney viscosity and to enable subsequent chain-end functionalization of the remaining living polymer fraction. Larger quantities tend to produce polymers containing terminally reactive groups or insufficient coupling and only enable an insufficient chain end-modification.

In one embodiment, from 0.01 to less than 5.0 mol, preferably from 0.05 to 2.5 mol, and more preferably from 0.1 to 1.5 mol, of the coupling agent is utilized for every 10.0 moles of living lithium polymer chain ends. The coupling agent can be added in a hydrocarbon solution (e.g. in cyclohexane) to the polymerization admixture in the reactor, with suitable mixing for distribution and reaction.

The polymer coupling reaction may be carried out in a temperature range of from 0° C. to 150° C., preferably from 15° C. to 120° C., and even more preferably from 40° C. to 100° C. There is no limitation for the duration of the coupling reaction. However, with respect to an economical polymerization process, for example, in the case of a batch polymerization process, the coupling reaction is usually stopped at about 5 to 60 minutes after the addition of the coupling agent.

The coupling agent can be added in a hydrocarbon solution, for example in cyclohexane, to the polymerization admixture in the reactor with suitable mixing for distribution and reaction.

Silane Sulfide Modification Agents

For control of polymer properties, silane sulfide modification agents (also referred to as silane sulfide modifiers or modifier agents) are employed in accordance with the present invention. The term "silane sulfide modification agent" includes the silane sulfide modifiers of Formula 1 of the present invention, including compounds of Formula 5 and Formula 6 as further specified below.

The silane sulfide modification agent of the present invention encompasses compounds of the following Formula 5:

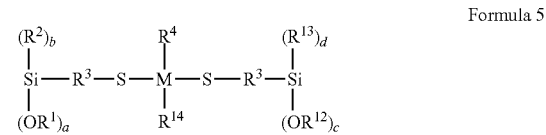

Formula 5

In Formula 5, M is a silicon atom or a tin atom;
$R^3$ is at least divalent and is $(C_8-C_{16})$ alkylarylalkyl, $(C_7-C_{16})$ arylalkyl, $(C_7-C_{16})$ alkylaryl, or $(C_1-C_{16})$ alkyl, and each group may be substituted with one or more of the following groups: tertiary amine group, silyl group, $(C_7-C_{18})$ aralkyl group and $(C_6-C_{18})$ aryl group;
$R^1$ and $R^{12}$ are each independently selected from $(C_1-C_4)$ alkyl;

$R^2$ and $R^{13}$ are each independently selected from ($C_1$-$C_{16}$) alkyl, ($C_7$-$C_{16}$) alkylaryl and ($C_7$-$C_{16}$) arylalkyl;

$R^4$ and $R^{14}$ are each independently selected from ($C_1$-$C_{16}$) alkyl and ($C_7$-$C_{16}$) alkylaryl;

b and d are each independently selected from an integer of 0, 1 and 2; a and c are each independently selected from an integer of 1, 2 and 3; and a+b=3; and c+d=3.

In one embodiment, $R^3$ is a ($C_1$-$C_{16}$) divalent alkyl group or ($C_8$-$C_{16}$) divalent alkylarylalkyl group.

In one embodiment, $R^3$ is alkylene. In a further embodiment, the alkylene is selected from —$CH_2$— (methylene), —$(CH_2)_2$— (ethylidene), —$(CH_2)_3$— (propylidene) and —$(CH_2)_4$— (butylidene).

In one embodiment, $R^3$ is a divalent aralkylene group. In a further embodiment, the aralkylene group is selected from —$CH_2$—$C_6H_4$—$CH_2$— (xylidene) and —$C_6H_4$—$C(CH_3)_2$—$C_6H_4$—.

In one embodiment, $R^2$, $R^4$, $R^{13}$ and $R^{14}$ are each independently a ($C_1$-$C_{16}$) alkyl. In a further embodiment, the alkyl is selected from $CH_3$— (methyl), $CH_3$—$CH_2$— (ethyl), $CH_3$—$(CH_2)_2$— (propyl), $CH_3$—$(CH_2)_3$ (n-butyl) and $CH_3$—$C(CH_3)_2$ (tert-butyl).

In one embodiment of Formula 5, $R^3$ is selected from the group consisting of linear $C_1$-$C_{10}$ alkyl (divalent), cyclic $C_6$-$C_{12}$ alkyl (divalent), $C_6$-$C_{15}$ aryl (divalent) and $C_7$-$C_{12}$ alkylaryl (divalent).

In one embodiment of Formula 5, b and d are each independently selected from an integer of 0 and 1; a and c are each independently selected from an integer of 2 and 3.

In one embodiment of the silane sulfide modification agent Formula 5, M is a silicon atom; a and c are each an integer selected from 2 and 3; and b and d are each an integer selected from 0 and 1.

While not explicitly shown in Formula 5, it will be understood that the silane sulfide modifiers of the present invention also encompass their corresponding Lewis base adducts (for example, with solvent molecules tetrahydrofuran, diethylether, dimethoxyethane coordinated with silicon atoms).

Specific preferred species of the silane sulfide modification agent of the present invention include the following compounds and their corresponding Lewis base adducts:

$(MeO)_3Si$—$(CH_2)_3$—S—$Si(Me)_2$-S—$(CH_2)_3$—$Si(OMe)_3$,
$(MeO)_3Si$—$(CH_2)_3$—S—$Si(Et)_2$-S—$(CH_2)_3$—$Si(OMe)_3$,
$(MeO)_3Si$—$(CH_2)_3$—S—$Si(Bu)_2$-S—$(CH_2)_3$—$Si(OMe)_3$,
$(EtO)_3Si$—$(CH_2)_3$—S—$Si(Me)_2$-S—$(CH_2)_3$—$Si(OEt)_3$,
$(EtO)_3Si$—$(CH_2)_3$—S—$Si(Et)_2$-S—$(CH_2)_3$—$Si(OEt)_3$,
$(EtO)_3Si$—$(CH_2)_3$—S—$Si(Bu)_2$-S—$(CH_2)_3$—$Si(OEt)_3$,
$(PrO)_3Si$—$(CH_2)_3$—S—$Si(Me)_2$-S—$(CH_2)_3$—$Si(OPr)_3$,
$(PrO)_3Si$—$(CH_2)_3$—S—$Si(Et)_2$-S—$(CH_2)_3$—$Si(OPr)_3$,
$(PrO)_3Si$—$(CH_2)_3$—S—$Si(Bu)_2$-S—$(CH_2)_3$—$Si(OPr)_3$,
$(MeO)_3Si$—$(CH_2)_2$—S—$Si(Me)_2$-S—$(CH_2)_2$—$Si(OMe)_3$,
$(MeO)_3Si$—$(CH_2)_2$—S—$Si(Et)_2S$—$(CH_2)_2$—$Si(OMe)_3$,
$(MeO)_3Si$—$(CH_2)_2$—S—$Si(Bu)_2$-S—$(CH_2)_2$—$Si(OMe)_3$,
$(EtO)_3Si$—$(CH_2)_2$—S—$Si(Me)_2$-S—$(CH_2)_2$—$Si(OEt)_3$,
$(EtO)_3Si$—$(CH_2)_2$—S—$Si(Et)_2$-S—$(CH_2)_2$—$Si(OEt)_3$,
$(EtO)_3Si$—$(CH_2)_2$—S—$Si(Bu)_2$-S—$(CH_2)_2$—$Si(OEt)_3$,
$(PrO)_3Si$—$(CH_2)_2$—S—$Si(Me)_2$-S—$(CH_2)_2$—$Si(OPr)_3$,
$(PrO)_3Si$—$(CH_2)_2$—S—$Si(Et)_2$-S—$(CH_2)_2$—$Si(OPr)_3$,
$(PrO)_3Si$—$(CH_2)_2$—S—$Si(Bu)_2$-S—$(CH_2)_2$—$Si(OPr)_3$,
$(MeO)_3Si$—$CH_2$—S—$Si(Me)_2$-S—$CH_2$—$Si(OMe)_3$,
$(MeO)_3Si$—$CH_2$—S—$Si(Et)_2$-S—$CH_2$—$Si(OMe)_3$,
$(MeO)_3Si$—$CH_2$—S—$Si(Bu)_2$-S—$CH_2$—$Si(OMe)_3$,
$(EtO)_3Si$—$CH_2$—S—$Si(Me)_2$-S—$CH_2$—$Si(OEt)_3$,
$(EtO)_3Si$—$CH_2$—S—$Si(Et)_2$-S—$CH_2$—$Si(OEt)_3$,
$(EtO)_3Si$—$CH_2$—S—$Si(Bu)_2$-S—$CH_2$—$Si(OEt)_3$,
$(PrO)_3Si$—$CH_2$—S—$Si(Me)_2$-S—$CH_2$—$Si(OPr)_3$,
$(PrO)_3Si$—$CH_2$—S—$Si(Et)_2$-S—$CH_2$—$Si(OPr)_3$,
$(PrO)_3Si$—$CH_2$—S—$Si(Bu)_2$-S—$CH_2$—$Si(OPr)_3$,
$(MeO)_3Si$—$CH_2$—$CMe_2$-$CH_2$—S—$Si(Me)_2$-S—$CH_2$—$CMe_2$-$CH_2$—$Si(OMe)_3$,
$(MeO)_3Si$—$CH_2$—$CMe_2$-$CH_2$—S—$Si(Et)_2$-S—$CH_2$—$CMe_2$-$CH_2$—$Si(OMe)_3$,
$(MeO)_3Si$—$CH_2$—$CMe_2$-$CH_2$—S—$Si(Bu)_2$-S—$CH_2$—$CMe_2$-$CH_2$—$Si(OMe)_3$,
$(EtO)_3Si$—$CH_2$—$CMe_2$-$CH_2$—S—$Si(Me)_2$-S—$CH_2$—$CMe_2$-$CH_2$—$Si(OEt)_3$,
$(EtO)_3Si$—$CH_2$—$CMe_2$-$CH_2$—S—$Si(Et)_2$-S—$CH_2$—$CMe_2$-$CH_2$—$Si(OEt)_3$,
$(EtO)_3Si$—$CH_2$—$CMe_2$-$CH_2$—S—$Si(Bu)_2$-S—$CH_2$—$CMe_2$-$CH_2$—$Si(OEt)_3$,
$(PrO)_3Si$—$CH_2$—$CMe_2$-$CH_2$—S—$Si(Me)_2$-S—$CH_2$—$CMe_2$-$CH_2$—$Si(OPr)_3$,
$(PrO)_3Si$—$CH_2$—$CMe_2$-$CH_2$—S—$Si(Et)_2$-S—$CH_2$—$CMe_2$-$CH_2$—$Si(OPr)_3$,
$(PrO)_3Si$—$CH_2$—$CMe_2$-$CH_2$—S—$Si(Bu)_2$-S—$CH_2$—$CMe_2$-$CH_2$—$Si(OPr)_3$,
$(MeO)_3Si$—$CH_2$—$C(H)Me$-$CH_2$—S—$Si(Me)_2$-S—$CH_2$—$C(H)Me$-$CH_2$—$Si(OMe)_3$,
$(MeO)_3Si$—$CH_2$—$C(H)Me$-$CH_2$—S—$Si(Et)_2$-S—$CH_2$—$C(H)Me$-$CH_2$—$Si(OMe)_3$,
$(MeO)_3Si$—$CH_2$—$C(H)Me$-$CH_2$—S—$Si(Bu)_2$-S—$CH_2$—$C(H)Me$-$CH_2$—$Si(OMe)_3$,
$(EtO)_3Si$—$CH_2$—$C(H)Me$-$CH_2$—S—$Si(Me)_2$-S—$CH_2$—$C(H)Me$-$CH_2$—$Si(OEt)_3$,
$(EtO)_3Si$—$CH_2$—$C(H)Me$-$CH_2$—S—$Si(Et)_2$-S—$CH_2$—$C(H)Me$-$CH_2$—$Si(OEt)_3$,
$(EtO)_3Si$—$CH_2$—$C(H)Me$-$CH_2$—S—$Si(Bu)_2$-S—$CH_2$—$C(H)Me$-$CH_2$—$Si(OEt)_3$,
$(PrO)_3Si$—$CH_2$—$C(H)Me$-$CH_2$—S—$Si(Me)_2$-S—$CH_2$—$C(H)Me$-$CH_2$—$Si(OPr)_3$,
$(PrO)_3Si$—$CH_2$—$C(H)Me$-$CH_2$—S—$Si(Et)_2$-S—$CH_2$—$C(H)Me$-$CH_2$—$Si(OPr)_3$,
$(PrO)_3Si$—$CH_2$—$C(H)Me$-$CH_$—S—$Si(Bu)_2$-S—$CH_2$—$C(H)Me$-$CH_2$—$Si(OPr)_3$,
$(MeO)_2(Me)Si$—$(CH_2)_3$—S—$Si(Me)_2$-S—$(CH_2)_3$—$Si(OMe)_2(Me)$,
$(MeO)_2(Me)Si$—$(CH_2)_3$—S—$Si(Et)_2$-S—$(CH_2)_3$—$Si(OMe)_2(Me)$,
$(MeO)_2(Me)Si$—$(CH_2)_3$—S—$Si(Bu)_2$-S—$(CH_2)_3$—$Si(OMe)_2(Me)$,
$(EtO)_2(Me)Si$—$(CH_2)_3$—S—$Si(Me)_2$-S—$(CH_2)_3$—$Si(OEt)_2(Me)$,
$(EtO)_2(Me)Si$—$(CH_2)_3$—S—$Si(Et)_2$-S—$(CH_2)_3$—$Si(OEt)_2(Me)$,
$(EtO)_2(Me)Si$—$(CH_2)_3$—S—$Si(Bu)_2$-S—$(CH_2)_3$—$Si(OEt)_2(Me)$,
$(PrO)_2(Me)Si$—$(CH_2)_3$—S—$Si(Me)_2$-S—$(CH_2)_3$—$Si(OPr)_2(Me)$,
$(PrO)_2(Me)Si$—$(CH_2)_3$—S—$Si(Et)_2$-S—$(CH_2)_3$—$Si(OPr)_2(Me)$,
$(PrO)_2(Me)Si$—$(CH_2)_3$—S—$Si(Bu)_2$-S—$(CH_2)_3$—$Si(OPr)_2(Me)$,
$(MeO)_2(Me)Si$—$(CH_2)_2$—S—$Si(Me)_2$-S—$(CH_2)_2$—$Si(OMe)_2(Me)$,
$(MeO)_2(Me)Si$—$(CH_2)_2$—S—$Si(Et)_2$-S—$(CH_2)_2$—$Si(OMe)_2(Me)$,
$(MeO)_2(Me)Si$—$(CH_2)_2$—S—$Si(Bu)_2$-S—$(CH_2)_2$—$Si(OMe)_2(Me)$,
$(EtO)_2(Me)Si$—$(CH_2)_2$—S—$Si(Me)_2$-S—$(CH_2)_2$—$Si(OEt)_2(Me)$,
$(EtO)_2(Me)Si$—$(CH_2)_2$—S—$Si(Et)_2$-S—$(CH_2)_2$—$Si(OEt)_2(Me)$, (EtO)$_2$(Me)Si—(CH$_2$)$_2$—S—Si(Bu)$_2$-S—(CH$_2$)$_2$—Si(OEt)$_2$(Me),
(PrO)$_2$(Me)Si—(CH$_2$)$_2$—S—Si(Me)$_2$-S—(CH$_2$)$_2$—Si(OPr)$_2$(Me),
(PrO)$_2$(Me)Si—(CH$_2$)$_2$—S—Si(Et)$_2$-S—(CH$_2$)$_2$—Si(OPr)$_2$(Me),
(PrO)$_2$(Me)Si—(CH$_2$)$_2$—S—Si(Bu)$_2$-S—(CH$_2$)$_2$—Si(OPr)$_2$(Me),
(MeO)$_2$(Me)Si—CH$_2$—S—Si(Me)$_2$-S—CH$_2$—Si(OMe)$_2$(Me),
(MeO)$_2$(Me)Si—CH$_2$—S—Si(Et)$_2$-S—CH$_2$—Si(OMe)$_2$(Me),
(MeO)$_2$(Me)Si—CH$_2$—S—Si(Bu)$_2$-S—CH$_2$—Si(OMe)$_2$(Me),
(EtO)$_2$(Me)Si—CH$_2$—S—Si(Me)$_2$-S—CH$_2$—Si(OEt)$_2$(Me),
(EtO)$_2$(Me)Si—CH$_2$—S—Si(Et)$_2$-S—CH$_2$—Si(OEt)$_2$(Me),
(EtO)$_2$(Me)Si—CH$_2$—S—Si(Bu)$_2$-S—CH$_2$—Si(OEt)$_2$(Me),
(PrO)$_2$(Me)Si—CH$_2$—S—Si(Me)$_2$-S—CH$_2$—Si(OPr)$_2$(Me),
(PrO)$_2$(Me)Si—CH$_2$—S—Si(Et)$_2$-S—CH$_2$—Si(OPr)$_2$(Me),
(PrO)$_2$(Me)Si—CH$_2$—S—Si(Bu)$_2$-S—CH$_2$—Si(OPr)$_2$(Me),
(MeO)$_2$(Me)Si—CH$_2$—CMe$_2$-CH$_2$—S—Si(Me)$_2$-S—CH$_2$—CMe$_2$-CH$_2$—Si(OMe)$_2$(Me),
(MeO)$_2$(Me)Si—CH$_2$—CMe$_2$-CH$_2$—S—Si(Et)$_2$-S—CH$_2$—CMe$_2$-CH$_2$—Si(OMe)$_2$(Me),
(MeO)$_2$(Me)Si—CH$_2$—CMe$_2$-CH$_2$—S—Si(Bu)$_2$-S—CH$_2$—CMe$_2$-CH$_2$—Si(OMe)$_2$(Me),
(EtO)$_2$(Me)Si—CH$_2$—CMe$_2$-CH$_2$—S—Si(Me)$_2$-S—CH$_2$—CMe$_2$-CH$_2$—Si(OEt)$_2$(Me),
(EtO)$_2$(Me)Si—CH$_2$—CMe$_2$-CH$_2$—S—Si(Et)$_2$-S—CH$_2$—CMe$_2$-CH$_2$—Si(OEt)$_2$(Me),
(EtO)$_2$(Me)Si—CH$_2$—CMe$_2$-CH$_2$—S—Si(Bu)$_2$-S—CH$_2$—CMe$_2$-CH$_2$—Si(OEt)$_2$(Me),
(PrO)$_2$(Me)Si—CH$_2$—CMe$_2$-CH$_2$—S—Si(Me)$_2$-S—CH$_2$—CMe$_2$-CH$_2$—Si(OPr)$_2$(Me),
(PrO)$_2$(Me)Si—CH$_2$—CMe$_2$-CH$_2$—S—Si(Et)$_2$-S—CH$_2$—CMe$_2$-CH$_2$—Si(OPr)$_2$(Me),
(PrO)$_2$(Me)Si—CH$_2$—CMe$_2$-CH$_2$—S—Si(Bu)$_2$-S—CH$_2$—CMe$_2$-CH$_2$—Si(OPr)$_2$(Me),
(MeO)$_2$(Me)Si—CH$_2$—C(H)Me-CH$_2$—S—Si(Me)$_2$-S—CH$_2$—C(H)Me-CH$_2$—Si(OMe)$_2$(Me),
(MeO)$_2$(Me)Si—CH$_2$—C(H)Me-CH$_2$—S—Si(Et)$_2$-S—CH$_2$—C(H)Me-CH$_2$—Si(OMe)$_2$(Me),
(MeO)$_2$(Me)Si—CH$_2$—C(H)Me-CH$_2$—S—Si(Bu)$_2$-S—CH$_2$—C(H)Me-CH$_2$—Si(OMe)$_2$(Me),
(EtO)$_2$(Me)Si—CH$_2$—C(H)Me-CH$_2$—S—Si(Me)$_2$-S—CH$_2$—C(H)Me-CH$_2$—Si(OEt)$_2$(Me),
(EtO)$_2$(Me)Si—CH$_2$—C(H)Me-CH$_2$—S—Si(Et)$_2$-S—CH$_2$—C(H)Me-CH$_2$—Si(OEt)$_2$(Me),
(EtO)$_2$(Me)Si—CH$_2$—C(H)Me-CH$_2$—S—Si(Bu)$_2$-S—CH$_2$—C(H)Me-CH$_2$—Si(OEt)$_2$(Me),
(PrO)$_2$(Me)Si—CH$_2$—C(H)Me-CH$_2$—S—Si(Me)$_2$-S—CH$_2$—C(H)Me-CH$_2$—Si(OPr)$_2$(M),
(PrO)$_2$(Me)Si—CH$_2$—C(H)Me-CH$_2$—S—Si(Et)$_2$-S—CH$_2$—C(H)Me-CH$_2$—Si(OPr)$_2$(Me),
(PrO)$_2$(Me)Si—CH$_2$—C(H)Me-CH$_2$—S—Si(Bu)$_2$-S—CH$_2$—C(H)Me-CH$_2$—Si(OPr)$_2$(Me),
(MeO)$_3$Si—(CH$_2$)$_3$—S—Sn(Me)$_2$-S—(CH$_2$)$_3$—Si(OMe)$_3$,
(MeO)$_3$Si—(CH$_2$)$_3$—S—Sn(Et)$_2$-S—(CH$_2$)$_3$—Si(OMe)$_3$,
(MeO)$_3$Si—(CH$_2$)$_3$—S—Sn(Bu)$_2$-S—(CH$_2$)$_3$—Si(OMe)$_3$,
(EtO)$_3$Si—(CH$_2$)$_3$—S—Sn(Me)$_2$-S—(CH$_2$)$_3$—Si(OEt)$_3$,
(EtO)$_3$Si—(CH$_2$)$_3$—S—Sn(Et)$_2$-S—(CH$_2$)$_3$—Si(OEt)$_3$,
(EtO)$_3$Si—(CH$_2$)$_3$—S—Sn(Bu)$_2$-S—(CH$_2$)$_3$—Si(OEt)$_3$,
(PrO)$_3$Si—(CH$_2$)$_3$—S—Sn(Me)$_2$-S—(CH$_2$)$_3$—Si(OPr),
(PrO)$_3$Si—(CH$_2$)$_3$—S—Sn(Et)$_2$-S—(CH$_2$)$_3$—Si(OPr)$_3$,
(PrO)$_3$Si—(CH$_2$)$_3$—S—Sn(Bu)$_2$-S—(CH$_2$)$_3$—Si(OPr)$_3$,
(MeO)$_3$Si—(CH$_2$)$_2$—S—Sn(Me)$_2$-S—(CH$_2$)$_2$—Si(OMe)$_3$,
(MeO)$_3$Si—(CH$_2$)$_2$—S—Sn(Et)$_2$-S—(CH$_2$)$_2$—Si(OMe)$_3$,
(MeO)$_3$Si—(CH$_2$)$_2$—S—Sn(Bu)$_2$-S—(CH$_2$)$_2$—Si(OMe)$_3$,
(EtO)$_3$Si—(CH$_2$)$_2$—S—Sn(Me)$_2$-S—(CH$_2$)$_2$—Si(OEt)$_3$,
(EtO)$_3$Si—(CH$_2$)$_2$—S—Sn(Et)$_2$-S—(CH$_2$)$_2$—Si(OEt)$_3$,
(EtO)$_3$Si—(CH$_2$)$_2$—S—Sn(Bu)$_2$-S—(CH$_2$)$_2$—Si(OEt)$_3$,
(PrO)$_3$Si—(CH$_2$)$_2$—S—Sn(Me)$_2$-S—(CH$_2$)$_2$—Si(OPr)$_3$,
(PrO)$_3$Si—(CH$_2$)$_2$S—Sn(Et)$_2$-S—(CH$_2$)$_2$Si(OPr)$_3$,
(PrO)$_3$Si—(CH$_2$)$_2$S—Sn(Bu)$_2$-S—(CH$_2$)$_2$Si(OPr)$_3$,
(MeO)$_3$Si—CH$_2$—S—Sn(Me)$_2$-S—CH$_2$—Si(OMe)$_3$,
(MeO)$_3$Si—CH$_2$—S—Sn(Et)$_2$-S—CH$_2$—Si(OMe)$_3$,
(MeO)$_3$Si—CH$_2$—S—Sn(Bu)$_2$-S—CH$_2$—Si(OMe)$_3$,
(EtO)$_3$Si—CH$_2$—S—Sn(Me)$_2$-S—CH$_2$—Si(OEt)$_3$,
(EtO)$_3$Si—CH$_2$—S—Sn(Et)$_2$-S—CH$_2$—Si(OEt)$_3$,
(EtO)$_3$Si—CH$_2$—S—Sn(Bu)$_2$-S—CH$_2$—Si(OEt)$_3$,
(PrO)$_3$Si—CH$_2$—S—Sn(Me)$_2$-S—CH$_2$—Si(OPr)$_3$,
(PrO)$_3$Si—CH$_2$—S—Sn(Et)$_2$-S—CH$_2$—Si(OPr)$_3$,
(PrO)$_3$Si—CH$_2$—S—Sn(Bu)$_2$-S—CH$_2$—Si(OPr)$_3$,
(MeO)$_3$Si—CH$_2$—CMe$_2$-CH$_2$—S—Sn(Me)$_2$-S—CH$_2$—CMe$_2$-CH$_2$—Si(OMe)$_3$,
(MeO)$_3$Si—CH$_2$—CMe$_2$-CH$_2$—S—Sn(Et)$_2$-S—CH$_2$—CMe$_2$-CH$_2$—Si(OMe)$_3$,
(MeO)$_3$Si—CH$_2$—CMe$_2$-CH$_2$—S—Sn(Bu)$_2$-S—CH$_2$—CMe$_2$-CH$_2$—Si(OMe)$_3$,
(EtO)$_3$Si—CH$_2$—CMe$_2$-CH$_2$—S—Sn(Me)$_2$-S—CH$_2$—CMe$_2$-CH$_2$—Si(OEt)$_3$,
(EtO)$_3$Si—CH$_2$—CMe$_2$-CH$_2$—S—Sn(Et)$_2$-S—CH$_2$—CMe$_2$-CH$_2$—Si(OEt)$_3$,
(EtO)$_3$Si—CH$_2$—CMe$_2$-CH$_2$—S—Sn(Bu)$_2$-S—CH$_2$—CMe$_2$-CH$_2$—Si(OEt)$_3$,
(PrO)$_3$Si—CH$_2$—CMe$_2$-CH$_2$—S—Sn(Me)$_2$-S—CH$_2$—CMe$_2$-CH$_2$—Si(OPr)$_3$,
(PrO)$_3$Si—CH$_2$—CMe$_2$-CH$_2$—S—Sn(Et)$_2$-S—CH$_2$—CMe$_2$-CH$_2$—Si(OPr)$_3$,
(PrO)$_3$Si—CH$_2$—CMe$_2$-CH$_2$—S—Sn(Bu)$_2$-S—CH$_2$—CMe$_2$-CH$_2$—Si(OPr)$_3$,
(MeO)$_3$Si—CH$_2$—C(H)Me-CH$_2$—S—Sn(Me)$_2$-S—CH$_2$—C(H)Me-CH$_2$—Si(OMe)$_3$,
(MeO)$_3$Si—CH$_2$—C(H)Me-CH$_2$—S—Sn(Et)$_2$-S—CH$_2$—C(H)Me-CH$_2$—Si(OMe)$_3$,
(MeO)$_3$Si—CH$_2$—C(H)Me-CH$_2$—S—Sn(Bu)$_2$-S—CH$_2$—C(H)Me-CH$_2$—Si(OMe)$_3$,
(EtO)$_3$Si—CH$_2$—C(H)Me-CH$_2$—S—Sn(Me)$_2$-S—CH$_2$—C(H)Me-CH$_2$—Si(OEt)$_3$,
(EtO)$_3$Si—CH$_2$—C(H)Me-CH$_2$—S—Sn(Et)$_2$-S—CH$_2$—C(H)Me-CH$_2$—Si(OEt)$_3$,
(EtO)$_3$Si—CH$_2$—C(H)Me-CH$_2$—S—Sn(Bu)$_2$-S—CH$_2$—C(H)Me-CH$_2$—Si(OEt)$_3$,
(PrO)$_3$Si—CH$_2$—C(H)Me-CH$_2$—S—Sn(Me)$_2$-S—CH$_2$—C(H)Me-CH$_2$—Si(OPr)$_3$,
(PrO)$_3$Si—CH$_2$—C(H)Me-CH$_2$—S—Sn(Et)$_2$-S—CH$_2$—C(H)Me-CH$_2$—Si(OPr)$_3$,
(PrO)$_3$Si—CH$_2$—C(H)Me-CH$_2$—S—Sn(Bu)$_2$-S—CH$_2$—C(H)Me-CH$_2$—Si(OPr)$_3$,
(MeO)$_2$(Me)Si—(CH$_2$)$_3$—S—Sn(Me)$_2$-S—(CH$_2$)$_3$—Si(OMe)$_2$(Me),
(MeO)$_2$(Me)Si—(CH$_2$)$_3$—S—Sn(Et)$_2$-S—(CH$_2$)$_3$—Si(OMe)$_2$(Me),
(MeO)$_2$(Me)Si—(CH$_2$)$_3$—S—Sn(Bu)$_2$-S—(CH$_2$)$_3$—Si(OMe)$_2$(Me),
(EtO)$_2$(Me)Si—(CH$_2$)$_3$—S—Sn(Me)$_2$-S—(CH$_2$)$_3$—Si(OEt)$_2$(Me), (EtO)₂(Me)Si—(CH₂)₃—S—Sn(Et)₂-S—(CH₂)₃—Si(OEt)₂(Me),
(EtO)₂(Me)Si—(CH₂)₃—S—Sn(Bu)₂-S—(CH₂)₃—Si(OEt)₂(Me),
(PrO)₂(Me)Si—(CH₂)₃—S—Sn(Me)₂-S—(CH₂)₃—Si(OPr)₂(Me),
(PrO)₂(Me)Si—(CH₂)₃—S—Sn(Et)₂-S—(CH₂)₃—Si(OPr)₂(Me),
(PrO)₂(Me)Si—(CH₂)₃—S—Sn(Bu)₂-S—(CH₂)₃—Si(OPr)₂(Me),
(MeO)₂(Me)Si—(CH₂)₂—S—Sn(Me)₂-S—(CH₂)₂—Si(OMe)₂(Me),
(MeO)₂(Me)Si—(CH₂)₂—S—Sn(Et)₂-S—(CH₂)₂—Si(OMe)₂(Me),
(MeO)₂(Me)Si—(CH₂)₂—S—Sn(Bu)₂-S—(CH₂)₂—Si(OMe)₂(Me),
(EtO)₂(Me)Si—(CH₂)₂—S—Sn(Me)₂-S—(CH₂)₂—Si(OEt)₂(Me),
(EtO)₂(Me)Si—(CH₂)₂—S—Sn(Et)₂-S—(CH₂)₂—Si(OEt)₂(Me),
(EtO)₂(Me)Si—(CH₂)₂—S—Sn(Bu)₂-S—(CH₂)₂—Si(OEt)₂(Me),
(PrO)₂(Me)Si—(CH₂)₂—S—Sn(Me)₂-S—(CH₂)₂—Si(OPr)₂(Me),
(PrO)₂(Me)Si—(CH₂)₂—S—Sn(Et)₂-S—(CH₂)₂—Si(OPr)₂(Me),
(PrO)₂(Me)Si—(CH₂)₂—S—Sn(Bu)₂-S—(CH₂)₂—Si(OPr)₂(Me),
(MeO)₂(Me)Si—CH₂—S—Sn(Me)₂-S—CH₂—Si(OMe)₂(Me),
(MeO)₂(Me)Si—CH₂—S—Sn(Et)₂-S—CH₂—Si(OMe)₂(Me),
(MeO)₂(Me)Si—CH₂—S—Sn(Bu)₂-S—CH₂—Si(OMe)₂(Me),
(EtO)₂(Me)Si—CH₂—S—Sn(Me)₂-S—CH₂—Si(OEt)₂(Me),
(EtO)₂(Me)Si—CH₂—S—Sn(Et)₂-S—CH₂—Si(OEt)₂(Me),
(EtO)₂(Me)Si—CH₂—S—Sn(Bu)₂-S—CH₂—Si(OEt)₂(Me),
(PrO)₂(Me)Si—CH₂—S—Sn(Me)₂-S—CH₂—Si(OPr)₂(Me),
(PrO)₂(Me)Si—CH₂—S—Sn(Et)₂-S—CH₂—Si(OPr)₂(Me),
(PrO)₂(Me)Si—CH₂—S—Sn(Bu)₂-S—CH₂—Si(OPr)₂(Me),
(MeO)₂(Me)Si—CH₂—CMe₂-CH₂—S—Sn(Me)₂-S—CH₂—CMe₂-CH₂—Si(OMe)₂(Me),
(MeO)₂(Me)Si—CH₂—CMe₂-CH₂—S—Sn(Et)₂-S—CH₂—CMe₂-CH₂—Si(OMe)₂(Me),
(MeO)₂(Me)Si—CH₂—CMe₂-CH₂—S—Sn(Bu)₂-S—CH₂—CMe₂-CH₂—Si(OMe)₂(Me),
(EtO)₂(Me)Si—CH₂—CMe₂-CH₂—S—Sn(Me)₂-S—CH₂—CMe₂-CH₂—Si(OEt)₂(Me),
(EtO)₂(Me)Si—CH₂—CMe₂-CH₂—S—Sn(Et)₂-S—CH₂—CMe₂-CH₂—Si(OEt)₂(Me),
(EtO)₂(Me)Si—CH₂—CMe₂-CH₂—S—Sn(Bu)₂-S—CH₂—CMe₂-CH₂—Si(OEt)₂(Me),
(PrO)₂(Me)Si—CH₂—CMe₂-CH₂—S—Sn(Me)₂-S—CH₂—CMe₂-CH₂—Si(OPr)₂(Me),
(PrO)₂(Me)Si—CH₂—CMe₂-CH₂—S—Sn(Et)₂-S—CH₂—CMe₂-CH₂—Si(OPr)₂(Me),
(PrO)₂(Me)Si—CH₂—CMe₂-CH₂—S—Sn(Bu)₂-S—CH₂—CMe₂-CH₂—Si(OPr)₂(Me),
(MeO)₂(Me)Si—CH₂—C(H)Me-CH₂—S—Sn(Me)₂-S—CH₂—C(H)Me-CH₂—Si(OMe)₂(Me),
(MeO)₂(Me)Si—CH₂—CH—C(H)Me-CH₂—S—Sn(Et)₂-S—CH₂—C(H)Me-CH₂—Si(OMe)₂(Me),
(MeO)₂(Me)Si—CH₂—C(H)Me-CH₂—S—Sn(Bu)₂-S—CH₂—C(H)Me-CH₂—Si(OMe)₂(Me),
(EtO)₂(Me)Si—CH₂—C(H)Me-CH₂—S—Sn(Me)₂-S—CH₂—C(H)Me-CH₂—Si(OEt)₂(Me),
(EtO)₂(Me)Si—CH₂—C(H)Me-CH₂—S—Sn(Et)₂-S—CH₂—C(H)Me-CH₂—Si(OEt)₂(Me),
(EtO)₂(Me)Si—CH₂—C(H)Me-CH₂—S—Sn(Bu)₂-S—CH₂—C(H)Me-CH₂—Si(OEt)₂(Me),
(PrO)₂(Me)Si—CH₂—C(H)Me-CH₂—S—Sn(Me)₂-S—CH₂—C(H)Me-CH₂—Si(OPr)₂(Me),
(PrO)₂(Me)Si—CH₂—C(H)Me-CH₂—S—Sn(Et)₂-S—CH₂—C(H)Me-CH₂—Si(OPr)₂(Me),
(PrO)₂(Me)Si—CH₂—C(H)Me-CH₂—S—Sn(Bu)₂-S—CH₂—C(H)Me-CH₂—Si(OPr)₂(Me).

The silane sulfide modification agent of the present invention furthermore includes compounds of the following Formula 6:

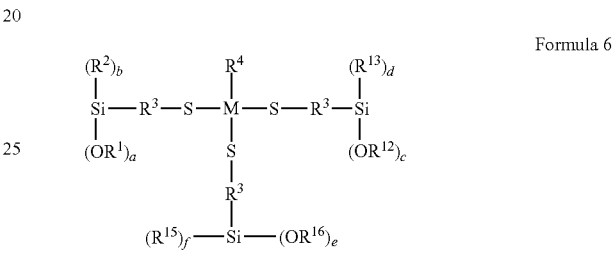

Formula 6

Formula 6, M is a silicon atom or a tin atom;
$R^3$ is at least divalent and is $(C_8$-$C_{16})$ alkylarylalkyl, $(C_7$-$C_{16})$ arylalkyl, $(C_7$-$C_{16})$ alkylaryl, or $(C_1$-$C_{16})$ alkyl, and each group may be substituted with one or more of the following groups: tertiary amine group, silyl group, $(C_7$-$C_{18})$ aralkyl group and $(C_6$-$C_{18})$ aryl group;
$R^1$, $R^{12}$ and $R^{16}$ are each independently selected from $(C_1$-$C_4)$ alkyl;
$R^2$, $R^{13}$ and $R^{15}$ are each independently selected from $(C_1$-$C_{16})$ alkyl, $(C_7$-$C_{16})$ alkylaryl and $(C_7$-$C_{16})$ arylalkyl;
$R^4$ is selected from $(C_1$-$C_{16})$ alkyl and $(C_7$-$C_{16})$ alkylaryl; b, d and f are each independently selected from an integer of 0, 1 and 2; a, c and e are each independently selected from an integer of 1, 2 and 3; a+b=3; c+d=3; and e+f=3.

In one embodiment, $R^3$ is a $(C_1$-$C_{16})$ divalent alkyl group or $(C_8$-$C_{16})$ divalent alylaralalkyl group.

In one embodiment, $R^3$ is alkylene. In a further embodiment, the alkylene is selected from —CH₂— (methylene), —(CH₂)₂— (ethylidene), —(CH₂)₃— (propylidene) and —(CH₂)₄— (butylidene).

In one embodiment, $R^3$ is a divalent aralkylene group. In a further embodiment, the aralkylene group is selected from —CH₂—C₆H₄—CH₂— (xylidene) and —C₆H₄—C(CH₃)₂—C₆H₄—.

In one embodiment, $R^2$, $R^4$, $R^{13}$ and $R^{15}$ are each independently a $(C_1$-$C_{16})$ alkyl. In a further embodiment, the alkyl is selected from CH₃— (methyl), CH₃—CH₂— (ethyl), CH₃—(CH₂)₂— (propyl), CH₃—(CH₂)₃ (n-butyl) and CH₃—C(CH₃)₂ (tert-butyl).

In one embodiment of Formula 6, $R^3$ is selected from the group consisting of linear $C_1$-$C_{10}$ alkyl (divalent), cyclic $C_6$-$C_{12}$ alkyl (divalent), $C_6$-$C_{15}$ aryl (divalent) and $C_7$-$C_{12}$ alkylaryl (divalent).

In one embodiment of Formula 6, b, d and f are each independently selected from an integer of 0 and 1; a, c and e are each independently selected from an integer of 2 and 3.

In one embodiment of the silane sulfide modification agent of Formula 6, M is a silicon atom; a, c and e are each an integer selected from 2 and 3; and b, d and f are each an integer selected from 0 and 1.

While not explicitly shown in Formula 6, it will be understood that the silane sulfide modifiers of the present invention may also include their corresponding Lewis base adducts (for example, with solvent molecules tetrahydrofuran, diethylether, dimethoxyethane coordinated with silicon atoms).

Specific preferred species of the silane sulfide modifier of the present invention include the following compounds and their corresponding Lewis base adducts:

{(MeO)$_3$Si—(CH$_2$)$_3$—S}$_3$Si(Me), {(MeO)$_3$Si—(CH$_2$)$_3$—S}$_3$Si(Et),
{(MeO)$_3$Si—(CH$_2$)$_3$—S}$_3$Si(Bu), {(EtO)$_3$Si—(CH$_2$)$_3$—S}$_3$Si(Me),
{(EtO)$_3$Si—(CH$_2$)$_3$—S}$_3$Si(Et), {(EtO)$_3$Si—(CH$_2$)$_3$—S}$_3$Si(Bu),
{(PrO)$_3$Si—(CH$_2$)$_3$—S}$_3$Si(Me), {(PrO)$_3$Si—(CH$_2$)$_3$—S}$_3$Si(Et),
{(PrO)$_3$Si—(CH$_2$)$_3$—S}$_3$Si(Bu), {(MeO)$_3$Si—(CH$_2$)$_2$—S}$_3$Si(Me),
{(MeO)$_3$Si—(CH$_2$)$_2$—S}$_3$Si(Et), {(MeO)$_3$Si—(CH$_2$)$_2$—S}$_3$Si(Bu),
{(EtO)$_3$Si—(CH$_2$)$_2$—S}$_3$Si(Me), {(EtO)$_3$Si—(CH$_2$)$_2$—S}$_3$Si(Et),
{(EtO)$_3$Si—(CH$_2$)$_2$—S}$_3$Si(Bu), {(PrO)$_3$Si—(CH$_2$)$_2$—S}$_3$Si(Me),
{(PrO)$_3$Si—(CH$_2$)$_2$—S}$_3$Si(Et), {(PrO)$_3$Si—(CH$_2$)$_2$—S}$_3$Si(Bu),
{(MeO)$_3$Si—CH$_2$—S}$_3$Si(Me), {(MeO)$_3$Si—CH$_2$—S}$_3$Si(Et), {(MeO)$_3$Si—CH$_2$—S}$_3$Si(Bu),
{(EtO)$_3$Si—CH$_2$—S}$_3$Si(Me), {(EtO)$_3$Si—CH$_2$—S}$_3$Si(Et), {(EtO)$_3$Si—CH$_2$—S}$_3$Si(Bu), {(PrO)$_3$Si—CH$_2$—S}$_3$Si(Me), {(PrO)$_3$Si—CH$_2$—S}$_3$Si(Et), {(PrO)$_3$Si—CH$_2$—S}$_3$Si(Bu),
(PrO)$_3$Si—CH$_2$—S}$_3$Si(Bu), {(MeO)$_3$Si—CH$_2$—CMe$_2$-CH$_2$—S}$_3$Si(Me),
{(MeO)$_3$Si—CH$_2$—CMe$_2$-CH$_2$—S}$_3$Si(Et), {(MeO)$_3$Si—CH$_2$—CMe$_2$-CH$_2$—S}$_3$Si(Bu), {(EtO)$_3$Si—CH$_2$—CMe$_2$-CH$_2$—S}$_3$Si(Me), {(EtO)$_3$Si—CH$_2$—CMe$_2$-CH$_2$—S}$_3$Si(Et), {(EtO)$_3$Si—CH$_2$—CMe$_2$-CH$_2$—S}$_3$Si(Bu), {(PrO)$_3$Si—CH$_2$—CMe$_2$-CH$_2$—S}$_3$Si(Me), {(PrO)$_3$Si—CH$_2$—CMe$_2$-CH$_2$—S}$_3$Si(Et),
{(MeO)$_3$Si—CH$_2$—C(H)Me-CH$_2$—S}$_3$Si(Me),
{(MeO)$_3$Si—CH$_2$—C(H)Me-CH$_2$—S}$_3$Si(Et), {(MeO)$_3$Si—CH$_2$—C(H)Me-CH$_2$—S}$_3$Si(Bu),
{(EtO)$_3$Si—CH$_2$—C(H)Me-CH$_2$—S}$_3$Si(Me), {(EtO)$_3$Si—CH$_2$—C(H)Me-CH$_2$—S}$_3$Si(Et), {(EtO)$_3$Si—CH$_2$—C(H)Me-CH$_2$—S}$_3$Si(Bu), {(PrO)$_3$Si—CH$_2$—C(H)Me-CH$_2$—S}$_3$Si(Me), {(PrO)$_3$Si—CH$_2$—C(H)Me-CH$_2$—S}$_3$Si(Et), {(MeO)$_2$(Me)Si—(CH$_2$)$_3$—S}$_3$Si(Me),
{(MeO)$_2$(Me)Si—(CH$_2$)$_3$—S}$_3$Si(Et), {(MeO)$_2$(Me)Si—(CH$_2$)$_3$—S}$_3$Si(Bu), {(EtO)$_2$(Me)Si—(CH$_2$)$_3$—S}$_3$Si(Me),
{(EtO)$_2$(Me)Si—(CH$_2$)$_3$—S}$_3$Si(Et),
{(EtO)$_2$(Me)Si—(CH$_2$)$_3$—S}$_3$Si(Bu), {(PrO)$_2$(Me)Si—(CH$_2$)$_3$—S}$_3$Si(Me), {(PrO)$_2$(Me)Si—(CH$_2$)$_3$—S}$_3$Si(Et), {(PrO)$_2$(Me)Si—(CH$_2$)$_3$—S}$_3$Si(Bu), {(MeO)$_2$(Me)Si—(CH$_2$)$_2$—S}$_3$Si(Me),
{(MeO)$_2$(Me)Si—(CH$_2$)$_2$—S}$_3$Si(Et), {(MeO)$_2$(Me)Si—(CH$_2$)$_2$—S}$_3$Si(Bu), {(MeO)$_2$(Me)Si—(CH$_2$)$_2$—S}$_3$Si(Me), {(EtO)$_2$(Me)Si—(CH$_2$)$_2$—S}$_3$Si(Et), {(EtO)$_2$(Me)Si—(CH$_2$)$_2$—S}$_3$Si(Bu),
{(PrO)$_2$(Me)Si—(CH$_2$)$_2$—S}$_3$Si(Me), {(PrO)$_2$(Me)Si—(CH$_2$)$_2$—S}$_3$Si(Et),
{(PrO)$_2$(Me)Si—(CH$_2$)$_2$—S}$_3$Si(Bu), {(MeO)$_2$(Me)Si—CH$_2$—S}$_3$Si(Me),
{(MeO)$_2$(Me)Si—CH$_2$—S}$_3$Si(Et), {(MeO)$_2$(Me)Si—CH$_2$—S}$_3$Si(Bu),
{(EtO)$_2$(Me)Si—CH$_2$—S}$_3$Si(Me), {(EtO)$_2$(Me)Si—CH$_2$—S}$_3$Si(Et),
{(EtO)$_2$(Me)Si—CH$_2$—S}$_3$Si(Bu), {(PrO)$_2$(Me)Si—CH$_2$—S}$_3$Si(Me),
{(PrO)$_2$(Me)Si—CH$_2$—S}$_3$Si(Et), {(PrO)$_2$(Me)Si—CH$_2$—S}$_3$Si(Bu),
(PrO)$_2$(Me)$_3$Si—CH$_2$—S}$_3$Si(Bu), {(MeO)$_2$(Me)Si—CH$_2$—CMe$_2$-CH$_2$—S}$_3$Si(Me),
{(MeO)$_2$(Me)Si—CH$_2$—CMe$_2$-CH$_2$—S}$_3$Si(Et),
{(MeO)$_2$(Me) Si—CH$_2$—CMe$_2$-CH$_2$—S}$_3$Si(Bu),
{(EtO)$_2$(Me)Si—CH$_2$—CMe$_2$-CH$_2$—S}$_3$Si(Me),
{(EtO)$_2$(Me)Si—CH$_2$—CMe$_2$-CH$_2$—S}$_3$Si(Et),
{(EtO)$_2$(Me)Si—CH$_2$—CMe$_2$-CH$_2$—S}$_3$Si(Bu),
{(PrO)$_2$(Me)Si—CH$_2$—CMe$_2$-CH$_2$—S}$_3$Si(Me),
{(PrO)$_2$(Me)Si—CH$_2$—CMe$_2$-CH$_2$—S}$_3$Si(Et),
{(MeO)$_2$(Me)Si—CH$_2$—C(H)Me-CH$_2$—S}$_3$Si(Me),
{(MeO)$_2$(Me)Si—CH$_2$—C(H)Me-CH$_2$—S}$_3$Si(Et),
{(MeO)$_2$(Me)Si—CH$_2$—C(H)Me-CH$_2$—S}$_3$Si(Bu),
{(EtO)$_2$(Me)Si—CH$_2$—C(H)Me-CH$_2$—S}$_3$Si(Me),
{(EtO)$_2$(Me)Si—CH$_2$—C(H)Me-CH$_2$—S}$_3$Si(Et),
{(EtO)$_2$(Me)Si—CH$_2$—C(H)Me-CH$_2$—S}$_3$Si(Bu),
{(PrO)$_2$(Me)Si—CH$_2$—C(H)Me-CH$_2$—S}$_3$Si(Me),
{(PrO)$_2$(Me) Si—CH$_2$—C(H)Me-CH$_2$—S}$_3$Si(Et),
{(MeO)$_3$Si—(CH$_2$)$_3$—S}$_3$Sn(Me), {(MeO)$_3$Si—(CH$_2$)$_3$—S}$_3$Sn(Et),
{(MeO)$_3$Si—(CH$_2$)$_3$—S}$_3$Sn(Bu), {(EtO)$_3$Si—(CH$_2$)$_3$—S}$_3$Sn(Me),
{(EtO)$_3$Si—(CH$_2$)$_3$—S}$_3$Sn(Et), {(EtO)$_3$Si—(CH$_2$)$_3$—S}$_3$Sn(Bu),
{(PrO)$_3$Si—(CH$_2$)$_3$—S}$_3$Sn(Me), {(PrO)$_3$Si—(CH$_2$)$_3$—S}$_3$Sn(Et),
{(PrO)$_3$Si—(CH$_2$)$_3$—S}$_3$Sn(Bu), {(MeO)$_3$Si—(CH$_2$)$_2$—S}$_3$Sn(Me),
{(MeO)$_3$Si—(CH$_2$)$_2$—S}$_3$Sn(Et), {(MeO)$_3$Si—(CH$_2$)$_2$—S}$_3$Sn(Bu),
{(EtO)$_3$Si—(CH$_2$)$_2$—S}$_3$Sn(Me), {(EtO)$_3$Si—(CH$_2$)$_2$—S}$_3$Sn(Et),
{(EtO)$_3$Si—(CH$_2$)$_2$—S}$_3$Sn(Bu), {(PrO)$_3$Si—(CH$_2$)$_2$—S}$_3$Sn(Me),
{(PrO)$_3$Si—(CH$_2$)$_2$—S}$_3$Sn(Et), {(PrO)$_3$Si—(CH$_2$)$_2$—S}$_3$Sn(Bu),
{(MeO)$_3$Si—CH$_2$—S}$_3$Sn(Me), {(MeO)$_3$Si—CH$_2$—S}$_3$Sn(Et),
{(MeO)$_3$Si—CH$_2$—S}$_3$Sn(Bu), {(EtO)$_3$Si—CH$_2$—S}$_3$Sn(Me), {(EtO)$_3$Si—CH$_2$—S}$_3$Sn(Et),
{(EtO)$_3$Si—CH$_2$—S}$_3$Sn(Bu), {(PrO)$_3$Si—CH$_2$—S}$_3$Sn(Me), {(PrO)$_3$Si—CH$_2$—S}$_3$Sn(Et), {(PrO)$_3$Si—CH$_2$—S$_3$Sn(Bu), (PrO)$_3$Si—CH$_2$—S}$_3$Sn(Bu),
{(MeO)$_3$Si—CH$_2$—CMe$_2$-CH$_2$—S}$_3$Sn(Me), {(MeO)$_3$Si—CH$_2$—CMe$_2$-CH$_2$—S}$_3$Sn(Et), {(MeO)$_3$Si—CH$_2$—CMe$_2$-CH$_2$—S}$_3$Sn(Bu), {(EtO)$_3$Si—CH$_2$—CMe$_2$-CH$_2$—S}$_3$Sn(Me), {(EtO)$_3$Si—CH$_2$—CMe$_2$-CH$_2$—S}$_3$Sn(Et), {(EtO)$_3$Si—CH$_2$—CMe$_2$-CH$_2$—S}$_3$Sn(Bu), {(PrO)$_3$Si—CH$_2$—CMe$_2$-CH$_2$—S}$_3$Sn(Me), {(PrO)$_3$Si—CH$_2$—CMe$_2$-CH$_2$—S}$_3$Sn(Et), {(MeO)$_3$Si—CH$_2$—C(H)Me-CH$_2$—S}$_3$Sn(Me),
{(MeO)$_3$Si—CH$_2$—C(H)Me-CH$_2$—S}$_3$Sn(Et),
{(MeO)$_3$Si—CH$_2$—C(H)Me-CH$_2$—S}$_3$Sn(Bu),
{(EtO)$_3$Si—CH$_2$—C(H)Me-CH$_2$—S}$_3$Sn(Me), {(EtO)$_3$Si—CH$_2$—C(H)Me-CH$_2$—S}$_3$Sn(Et),
{(EtO)$_3$Si—CH$_2$—C(H)Me-CH$_2$—S}$_3$Sn(Bu), {(PrO)$_3$Si—CH$_2$—C(H)Me-CH$_2$—S}$_3$Sn(Me),

{(PrO)$_3$Si—CH$_2$—C(H)Me-CH$_2$—S}$_3$Sn(Et), {(MeO)$_2$(Me)Si—(CH$_2$)$_3$—S}$_3$Sn(Me),
{(MeO)$_2$(Me)Si—(CH$_2$)$_3$—S}$_3$Sn(Et), {(MeO)$_2$(Me)Si—(CH$_2$)$_3$—S}$_3$Sn(Bu), {(EtO)$_2$(Me)Si—(CH$_2$)$_3$—S}$_3$Sn(Me), {(EtO)$_2$(Me)Si—(CH$_2$)$_3$—S}$_3$Sn(Et),
{(EtO)$_2$(Me)Si—(CH$_2$)$_3$—S}$_3$Sn(Bu), {(PrO)$_2$(Me)Si—(CH$_2$)$_3$—S}$_3$Sn(Me), {(PrO)$_2$(Me)Si—(CH$_2$)$_3$—S}$_3$Sn(Et), {(PrO)$_2$(Me)Si—(CH$_2$)$_3$—S}$_3$Sn(Bu), {(MeO)$_2$(Me)Si—(CH$_2$)$_2$—S}$_3$Sn(Me),
{(MeO)$_2$(Me)Si—(CH$_2$)$_2$—S}$_3$Sn(Et), {(MeO)$_2$(Me)Si—(CH$_2$)$_2$—S}$_3$Sn(Bu), {(EtO)$_2$(Me)Si—(CH$_2$)$_2$—S}$_3$Sn(Me), {(EtO)$_2$(Me)Si—(CH$_2$)$_2$—S}$_3$Sn(Et), {(EtO)$_2$(Me)Si—(CH$_2$)$_2$—S}$_3$Sn(Bu),
{(PrO)$_2$(Me)Si—(CH$_2$)$_2$—S}$_3$Sn(Me), {(PrO)$_2$(Me)Si—(CH$_2$)$_2$—S}$_3$Sn(Et),
{(PrO)$_2$(Me)Si—(CH$_2$)$_2$—S}$_3$Si(Bu), {(MeO)$_2$(Me)Si—CH$_2$—S}$_3$Si(Me),
{(MeO)$_2$(Me)Si—CH$_2$—S}$_3$Si(Et), {(MeO)$_2$(Me)Si—CH$_2$—S}$_3$Si(Bu),
{(EtO)$_2$(Me)Si—CH$_2$—S}$_3$Si(Me), {(EtO)$_2$(Me)Si—CH$_2$—S}$_3$Si(Et),
{(EtO)(Me)Si—CH$_2$—S}$_3$Si(Bu), {(PrO)$_2$(Me)Si—CH$_2$—S}$_3$Si(Me),
{(PrO)$_2$(Me)Si—CH$_2$—S}$_3$Si(Et), {(PrO)$_2$(Me)Si—CH$_2$—S}$_3$Si(Bu),
(PrO)$_2$(Me)$_3$Si—CH$_2$—S}$_3$Si(Bu), {(MeO)$_2$(Me)Si—CH$_2$—CMe$_2$-CH$_2$—S}$_3$Si(Me),
{(MeO)$_2$(Me)Si—CH$_2$—CMe$_2$-CH$_2$—S}$_3$Si(Et),
{(MeO)$_2$(Me)Si—CH$_2$—CMe$_2$-CH$_2$—S}$_3$Si(Bu),
{(EtO)$_2$(Me)Si—CH$_2$—CMe$_2$-CH$_2$—S}$_3$Si(Me),
{(EtO)$_2$(Me)Si—CH$_2$—CMe$_2$-CH$_2$—S}$_3$Si(Et),
{(EtO)$_2$(Me)Si—CH$_2$—CMe$_2$-CH$_2$—S}$_3$Si(Bu),
{(PrO)$_2$(Me)Si—CH$_2$—CMe$_2$-CH$_2$—S})$_3$Si(Me),
{(PrO)$_2$(Me)Si—CH$_2$—CMe$_2$-CH$_2$—S})$_3$Si(Et),
{(MeO)$_2$(Me)Si—CH$_2$—C(H)Me-CH$_2$—S}$_3$Si(Me),
{(MeO)$_2$(Me)Si—CH$_2$—C(H)Me-CH$_2$—S}$_3$Si(Et),
{(MeO)$_2$(Me)Si—CH$_2$—C(H)Me-CH$_2$—S}$_3$Si(Bu),
{(EtO)$_2$(Me)Si—CH$_2$—C(H)Me-CH$_2$—S}$_3$Si(Me),
{(EtO)$_2$(Me)Si—CH$_2$—(H)Me-C(H)Me-CH$_2$—}S$_3$Si(Et),
{(EtO)$_2$(Me)Si—CH$_2$—C(H)Me-CH$_2$—}S$_3$Si(Bu),
{(PrO)$_2$(Me)Si—CH$_2$—C(H)Me-CH$_2$—S}$_3$Si(Me),
{(PrO)$_2$(Me)Si—CH$_2$—C(H)Me-CH$_2$—S}$_3$Si(Et).

The silane sulfide modification agents may be added intermittently (or at regular or irregular intervals) or continuously during the polymerization, but are preferably added at a conversion rate of the polymerization of more than 80 percent, and more preferably at a conversion rate of more than 90 percent. Preferably, a substantial amount of the polymer chain ends is not terminated prior to the reaction with the silane sulfide modification agent; that is, the living polymer chain ends are present and capable of reacting with the silane sulfide end modification agent. The silane sulfide modification reaction may occur before, after or during the addition of the coupling agent (if used) or any other further modification agent (if used). Preferably, in case the optional coupling agent is employed, the silane sulfide modification reaction is completed after the addition of the coupling agent. See, for example, WO 2009/148932, incorporated herein by reference. Preferably, in case a further modification agent, which is not a silane sulfide modification agent of Formula 1, including Formula 5 or Formula 6, is used in addition to the silane sulfide modification agent of the invention, the reaction with the silane sulfide modifier of the invention is preferably completed prior to the addition of the further modification agent. The preferred order of addition causes the silane sulfide modification agents of the invention to react with more than one of the living polymer chains forming modified coupled macromolecular compounds (provided the ratio of the number of living polymer chains to the number of silane sulfide modification agents is significantly larger than 1, preferably larger than 2), while the further modification agents form essentially linear modified macromolecular compounds (provided the ratio of the number of living polymer chains still available after completion of the reaction with the silane sulfide modification agent of the invention to the number of further modification agents is relatively close to 1, such as lower than 1.4 or more preferably lower than 1.0).

In one embodiment, more than 20 percent, preferably more than 35 percent, and even more preferably more than 50 percent of the living polymer chains, as determined by GPC, formed in the course of the polymerization process, are linked with a silane sulfide modification agent in the process of polymer silane sulfide modification.

In one embodiment, more than 20 percent of the living polymer chain ends, as determined by GPC, are reacted with coupling agent(s), prior to the addition of the silane sulfide modification agent(s). In yet other embodiments, more than 35 percent of the living polymer chain ends are reacted with coupling agent(s), prior to the addition of the silane sulfide modification agent(s).

In one embodiment, between 20 and 35 percent of the living polymer chain ends, as determined by GPC, are reacted with coupling agent(s), prior to the addition of silane sulfide modification agent(s). In other embodiments, between 35 and 50 percent of the living polymer chain ends, as determined by GPC, are reacted with coupling agent(s), prior to the addition of silane sulfide modification agent(s). In yet other embodiment, between 50 and 80 percent of the living polymer chain ends are reacted with coupling agent(s), prior to the addition of silane sulfide modification agent(s).

In one embodiment, more than 20 percent, preferably between 20 and 35 percent, of the living polymer chain ends, as determined by GPC, are reacted with silane sulfide modification agent(s) of the invention, prior to the addition of the further modification agent(s). In yet other embodiments, more than 35 percent, preferably between 50 and 80 percent, of the living polymer chain ends are reacted with silane sulfide modification agent(s) of the invention, prior to the addition of the further modification agent(s).

In one embodiment, more than 50 percent, preferably more than 60 percent, and more preferably more than 75 percent, as determined by GPC, of the living polymer macromolecules (still remaining after the coupling reaction) react with a silane sulfide modification agent. Silane sulfide modified polymer macromolecules, according to the invention, comprise a functionality derived from the silane sulfide modification agent.

The nature of the optional further modification agent(s) preferably corresponds to the following Formula 7

  Formula 7, wherein
$M^1$ is silicon or tin; x is an integer selected from 1, 2 and 3; y is an integer selected from 0, 1, and 2; x+y=3; R is independently selected from ($C_1$-$C_{16}$) alkyl; and R' is ($C_1$-$C_{16}$) alkyl, ($C_8$-$C_{16}$) alkylarylalkyl, ($C_7$-$C_{16}$) arylalkyl or ($C_7$-$C_{16}$) alkylaryl.
Specific examples of the further modification agent(s) are listed in WO 2007/047943, incorporated herein by reference.

Preparation of Silane Sulfide Modifier Agents

The silane sulfide modifier of Formula 1 of the present invention may be prepared by reacting a sulfur containing compound of Formula 2:

$(R^1O)_x(R^2)_y Si—R^3—S—H$ (Formula 2), wherein H is hydrogen and the other symbols have the same meaning as defined with respect to Formula 1, with a compound of Formula 4:

$M(R^4)_t(X)_u$ (Formula 4), wherein M is silicon or tin, u is an integer selected from 2, 3 and 4; $R^4$, X and t are as defined above; and t+u=4, optionally in the presence of a strong Lewis base, such as for example but not limited to a compound of Formula 3a and Formula 3b, $R^5R^6R^7N$ (Formula 3a)

$R^8R^9N—(CR^{10}R^{11})_v—NR^8R^9$ (Formula 3b)

wherein $R^5$, $R^6$, $R^7$, $R^8$, $R^9$, $R^{10}$ and $R^{11}$ are each independently selected from hydrogen, ($C_1$-$C_{16}$) alkyl, ($C_7$-$C_{16}$) alkylaryl; ($C_7$-$C_{16}$) arylalkyl and ($C_6$-$C_{16}$) aryl; and v is an integer selected from 1 to 10.

In one preferred embodiment the Lewis base is selected from a compound of Formula 3a.

In one preferred embodiment the Lewis base is selected from a compound of Formula 3a and $R^5$, $R^6$ and $R^7$ are each independently selected from methyl (Me), ethyl (Et), propyl (Pr) and butyl (Bu).

In one preferred embodiment, u in Formula 4 is 2.

The silane sulfide modifier of Formula 1 of the present invention may be also prepared by reacting a sulfur containing compound of Formula 11:

$(R^1O)_x(R^2)_y Si—R^3—S-M^2$ (Formula 11), wherein $M^2$ is lithium, sodium or potassium and the other symbols have the same meaning as defined with respect to Formula 1, with a compound of Formula 4:

$M(R^4)_t(X)_u$ (Formula 4), wherein M is silicon or tin, u is an integer selected from 2, 3 and 4; $R^4$, X and t are as defined above; and t+u=4.

In one preferred embodiment u in Formula 4 is 2.

Process of Silane Sulfide Modification

The silane sulfide end-modification agent may be directly added to a solution of the living anionic elastomeric polymer, however, it may be beneficial to add the agent in dissolved form, such as in an inert solvent (e.g. cyclohexane). The amount of silane sulfide modification agent added to the living anionic elastomeric polymer may vary depending on the kind of monomer species, kind and amount of optional coupling agent, kind and amount of further modification agent, reaction conditions, and desired end properties, but is generally from 0.05 to 5 mol-equivalent, preferably from 0.1 to 2.0 mol-equivalent, and most preferably from 0.2 to 1.5 mol-equivalent, per mol equivalent of alkali metal in the initiator compound. In one embodiment, the silane sulfide modification agent is used to form a branched modified macromolecular compound and is employed in an amount from 0.1 to 0.5 mol-equivalent per mol equivalent of alkali metal in the initiator compound. In another embodiment, the silane sulfide modification agent is used to form a linear modified macromolecular compound and is employed in an amount from 0.6 to 1.5 mol-equivalent per mol equivalent of alkali metal in the initiator compound. The polymer silane sulfide modification reaction may be carried out in a temperature range of from 0° C. to 150° C., preferably of from 15° C. to 120° C., and even more preferably of from 40° C. to 100° C. There is no limitation for the duration of the silane sulfide modification reaction. However, with respect to an economical polymerization process, for example, in the case of a batchwise polymerization process, the silane sulfide modification reaction is usually stopped at about 5 to 60 minutes after the addition of the modifier.

The invention also provides a method for making the silane sulfide modified elastomeric macromolecular compound comprising the following steps A through D. Step A: reacting the polymerization initiator, as described herein, with one or more monomer types, and preferably monomers selected from butadiene, styrene, isoprene, alpha methylstyrene and combinations thereof, in a polymerization solvent to form a reaction mixture A. Suitable polymerization solvents include non-polar aliphatic and non-polar aromatic solvents, preferably hexane, heptane, butane, pentane, isopar, cyclohexane, toluene and benzene. Step B: optionally reacting reaction mixture A with at least one coupling agent, preferably selected from the group consisting of $SnCl_4$, $(R^1)_3SnCl$, $(R^1)_2SnCl_2$, $R^1SnCl_3$, $SiCl_4$, $(R^1)_3SiCl$, $(R^1)_2SiCl_2$, $R^1SiCl_3$, $Cl_3Si—SiCl_3$, $Cl_3Si—O—SiCl_3$, $Cl_3Sn—SnCl_3$, $Cl_3Sn—O—SnCl_3$, wherein $R^1$ is as defined above, $Sn(OMe)_4$, $Si(OMe)_4$, $Sn(OEt)_4$ and $Si(OEt)_4$ to form a reaction mixture B. Step C: reacting the reaction mixture A or B with at least one silane sulfide modification agent of Formula 1 as defined above, including Formula 5 and Formula 6, to produce a silane sulfide modified macromolecular compound of the invention, usually in the form of a polymer composition C. Step D: optionally reacting the silane sulfide modified macromolecular compound or polymer composition C obtained in Step C with a further modification agent, preferably with a compound of Formula 7.

In a preferred embodiment, the polymerization initiator compound is reacted first with monomers to form a living polymer (step A). Some of these polymer molecules are optionally reacted with coupling agent to form branched polymer molecules (optional step B). In step C, some of the living polymer molecules are reacted with the silane sulfide chain-end modification agent to form linear silane sulfide modified macromolecular compound(s). Linear silane sulfide modified macromolecular compounds are formed when one equivalent of living polymer chains are modified (or reacted) with one equivalent of silane sulfide modification agent.

In another preferred embodiment, the polymerization initiator compound is reacted first with monomers to form a living polymer (step A). Some of the polymer molecules are reacted with silane sulfide modification agent to form branched modified polymer molecules (step C). Branched silane sulfide modified macromolecular compounds are formed when two or more equivalents of living polymer chains are modified (or reacted) with one equivalent of silane sulfide modification agent. For example, if three (equivalents of) living polymer chains are modified with one (equivalent of) silane sulfide modification agent, a silane sulfide modified macromolecular compound is formed, which comprises three polymer chain arms. In optional step D, some of the living polymer molecules are reacted with the further modification agent to form linear modified macromolecular compound(s).

In another embodiment, the optional coupling agent is selected from the following: $SnCl_4$, $Bu_3SnCl$, $Bu_2SnCl_2$, BuSnCl$_3$, Me$_3$SiCl, Me$_2$SiCl$_2$, Cl$_3$Si—SiCl$_3$, Cl$_3$Si—O—SiCl$_3$, Sn(OMe)$_4$, Si(OMe)$_4$, Sn(OEt)$_4$, Si(OEt)$_4$ and combinations thereof.

In a preferred embodiment, the silane sulfide modification agent is the compound of Formula 5. In a another preferred embodiment, the silane sulfide modification agent is the compound of Formula 6.

Monomers

Monomers useful for preparing living anionic elastomeric polymers and, thus, the silane sulfide modified macromolecular compounds of the present invention and the polymer compositions comprising said macromolecular compound(s) include conjugated olefins and olefins selected from α-olefins, internal olefins, cyclic olefins, polar olefins and nonconjugated diolefins. Suitable conjugated unsaturated monomers are preferably conjugated dienes, such as 1,3-butadiene, 2-alkyl-1,3-butadiene, preferably, isoprene (2-methyl-1,3-butadiene), 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene, 1,3-cyclooctadiene. Preferred olefins are C$_{2-20}$ α-olefins, including, but not limited to, long chain macromolecular α-olefins, more especially an aromatic vinyl compound. Preferred aromatic vinyl compounds are styrene, including C$_{1-4}$ alkyl substituted styrene, such as 2-methylstyrene, 3-methylstyrene, 4-methylstyrene, 2,4-dimethylstyrene, 2,4,6-trimethylstyrene, α-methylstyrene and stilbene, 2,4-diisopropylstyrene, 4-tert-butylstyrene, vinyl benzyl dimethylamine, (4-vinylbenzyl)dimethyl aminoethyl ether, N,N-dimethylaminoethyl styrene, tert-butoxystyrene, vinylpyridine, and mixtures thereof. Suitable polar olefins included acrylonitrile, methacrylates, methylmethacrylate. Suitable nonconjugated olefins include C$_{4-20}$ diolefins, especially norbornadiene, ethylidenenorbornene, 1,4-hexadiene, 1,5-hexadiene, 1,7-octadiene, 4-vinylcyclohexene, divinylbenzene including 1,2-divinylbenzene, 1,3-divinylbenzene and 1,4-divinylbenzene and mixtures thereof. Preferred conjugated dienes include butadiene, isoprene and cyclopentadiene, and preferred aromatic α-olefins include: styrene and 4-methylstyrene.

Silane Sulfide Modified Polymer Macromolecules

The term "silane sulfide modified macromolecular compound" is intended to mean the reaction product of one or more living polymer chain(s) with the silane sulfide modifier agents of the present invention. Silane sulfide modified macromolecular compounds may be represented by the following Formula P1

((P)(R$^1$O)$_{x-r}$(R$^2$)$_y$Si—R$^3$—S)$_s$M(R$^4$)$_t$(X)$_u$     (Formula P1), wherein P is a polymer chain comprising monomer units derived from at least one of the following monomer groups: butadiene, isoprene, styrene and alpha-methylstyrene, the number of monomer units per macromolecule ranging from 10 to 50.000, preferably from 20 to 40.000;

M is a silicon atom or a tin atom;

x is an integer selected from 1, 2 and 3; y is an integer selected from 0, 1, and 2; r is an integer selected from 1, 2 and 3; wherein x+y+r=3;

s is an integer selected from 2, 3 and 4; t is an integer selected from 0, 1 and 2; u is an integer selected from 0, 1 and 2; wherein s+t+u=4;

R$^1$ is independently selected from a hydrogen atom and (C$_1$-C$_6$) alkyl;

R$^2$ is independently selected from (C$_1$-C$_{16}$) alkyl, (C$_7$-C$_{16}$) alkylaryl and (C$_7$-C$_{16}$) arylalkyl;

R$^3$ is at least divalent and is independently selected from (C$_1$-C$_{16}$) alkyl, (C$_8$-C$_{16}$) alkylarylalkyl, (C$_7$-C$_{16}$) arylalkyl and (C$_7$-C$_{16}$) alkylaryl, and each group may be substituted with one or more of the following groups: tertiary amine group, silyl group, (C$_7$-C$_{18}$) aralkyl group and (C$_6$-C$_{18}$) aryl group;

R$^4$ is independently selected from (C$_1$-C$_{16}$) alkyl and (C$_7$-C$_{16}$) alkylaryl; and X is independently selected from chloride, bromide and —OR$^5$; wherein R$^5$ is selected from (C$_1$-C$_{16}$) alkyl and (C$_7$-C$_{16}$) arylalkyl.

In a preferred embodiment, R$^3$ is divalent and is (C$_1$-C$_6$) alkyl.

In one embodiment, X is —OR$^5$; wherein R$^5$ is selected from (C$_1$-C$_{16}$) alkyl.

In another embodiment, X is chloride or bromide.

In one preferred embodiment, R$^2$ and R$^4$ are independently selected from (C$_1$-C$_{16}$) alkyl.

In one preferred embodiment, R$^1$, R$^2$, R$^4$ and R$^5$ are independently selected from (C$_1$-C$_4$) alkyl.

In one embodiment, s and t are each 2 and u is 0.

In another embodiment, s is 3, t is 1 and u is 0.

In one embodiment, r is 1, x is 1 and y is 1.

In one embodiment, r is 1, x is 0 and y is 2.

Silane sulfide modified macromolecular compounds may be exemplified by the following Formulas P2 to P6:

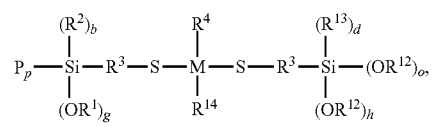
(Formula P2)

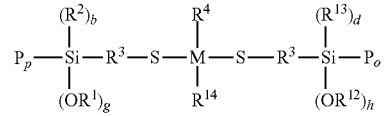
(Formula P3)

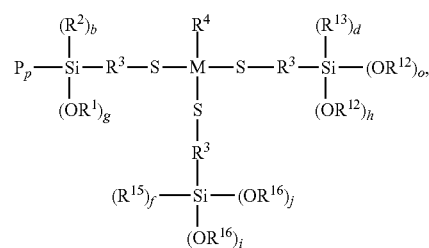
(Formula P4)

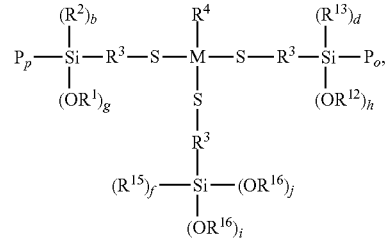
(Formula P5)

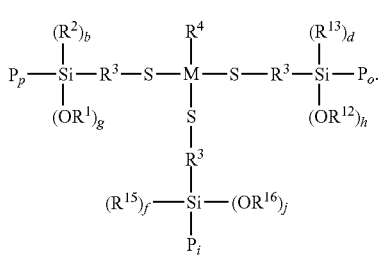
(Formula P6)

In the above formulas, P is a polymer chain comprising monomer units derived from at least one of the following monomer groups: butadiene, isoprene, styrene and alpha-methylstyrene, the number of monomer units per polymer macromolecule ranging from 10 to 50.000, preferably from 20 to 40.000; $R^3$ is at least divalent and is ($C_8$-$C_{16}$) alkylarylalkyl, ($C_7$-$C_{16}$) arylalkyl, ($C_7$-$C_{16}$) alkylaryl, or ($C_1$-$C_{16}$) alkyl, and each group may be substituted with one or more of the following groups: tertiary amine group, silyl group, ($C_7$-$C_{18}$) aralkyl group and ($C_6$-$C_{18}$) aryl group;
M is a silicon atom or a tin atom;
$R^1$, $R^{12}$ and $R^{16}$ are each independently selected from a hydrogen atom and ($C_1$-$C_4$) alkyl;
$R^4$ is selected from ($C_1$-$C_{16}$) alkyl and ($C_7$-$C_{16}$) alkylaryl;
$R^2$, $R^{13}$ and $R^{15}$ are each independently selected from ($C_1$-$C_{16}$) alkyl, ($C_7$-$C_{16}$) alkylaryl and ($C_7$-$C_{16}$) arylalkyl;
p, o and i are each independently selected from an integer of 1, 2 and 3; g, h and j are each independently selected from an integer of 0, 1 and 2; b, d and f are each independently selected from an integer of 0, 1 and 2; and
p+b+g=3, o+d+h=3 and i+f+j=3.
In one embodiment in Formula P2 and P3, $R^3$ is divalent and is ($C_1$-$C_{16}$) alkyl; and $R^2$, $R^4$, $R^{13}$ and $R^{14}$ are each independently selected from ($C_1$-$C_{16}$) alkyl; and $R^1$ and $R^{12}$ are each independently selected from ($C_1$-$C_4$) alkyl; and p and o are each independently selected from an integer of 1 and 2; g and h are each independently selected from an integer of 1 and 2; b and d are each independently selected from an integer of 0 and 1.
In one embodiment in Formula P4, P5 and P6, $R^3$ is divalent and is ($C_1$-$C_{16}$) alkyl; and $R^2$, $R^4$, $R^{13}$ and $R^{15}$ are each independently selected from ($C_1$-$C_{16}$) alkyl; and $R^1$, $R^{12}$ and $R^{16}$ are each independently selected from ($C_1$-$C_4$) alkyl; and p, o and i are each independently selected from an integer of 1 and 2; g, h and j are each independently selected from an integer of 1 and 2; b, d and f are each independently selected from an integer of 0 and 1.
While not explicitly shown in Formula P1 to Formula P6, it will be understood that the compounds include their corresponding Lewis base adducts.
From the above listed Formulas P1 to P6, the Formulas P1 and P2 are preferred.
Specific preferred modified macromolecular compounds include the following polymers (and their corresponding Lewis base adducts):

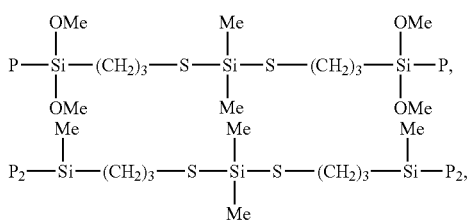

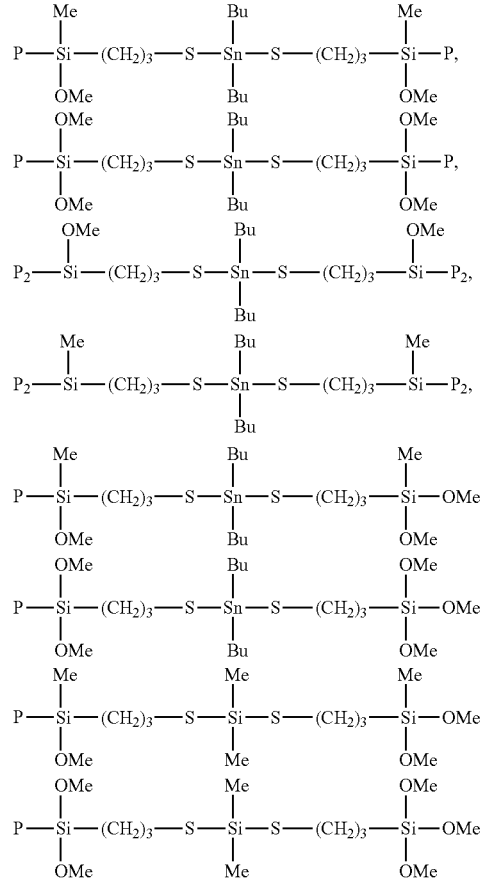

While not wishing to be bound by theory, dihydrocarbylsilendiyl, including dialkylsilendiyl, diaralkylsilendiyl and diarylsilendiyl; dihydrocarbylstannendiyl, including dialkylstannendiyl, diaralkylstannendiyl and diarylstannendiyl groups and hydrocarbylsilentriyl, including alkylsilentriyl, aralkylsilentriyl and arylsilentriyl; hydrocarbylstannentriyl, including alkylstannentriyl, aralkylstannentriyl and arylstannentriyl groups of Formulas P1, P2, P3, P4, P5 and P6 are each believed to function as a protective group, which prevents unintended subsequent reaction. These "protective" groups, (—$SiR^4R^8$—), (—$SnR^4R^8$—), (—$SiR^4$=) and (—$SnR^4$=), may be removed by exposure to a compound containing —OH groups, such as water, alcohols, anionic acids or organic acids (for example hydrochloric acid, sulfuric acid or carboxylic acids), thus forming an "unprotected" thiol (—SH) group. Such conditions are typically present during vulcanization. Depending on the polymer "work up" conditions, either one or both of unprotected and protected modified macromolecular compounds may be obtained. For example, steam stripping of a polymer solution containing the modified macromolecular compounds of Formula P1, P2, P3, P4, P5 and P6 will remove a certain percentage of the protecting trihydrocarbyl groups, including trialkyl, triaralkyl, or triarylsilyl groups, resulting in the unprotected thiol (—SH) group and forming a certain percentage of compounds of Formula P7 (corresponding to Formula P1), Formula P8, Formula P9 or Formula P10.

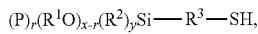
(Formula P7)

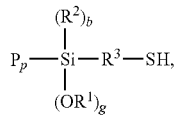
(Formula P8)

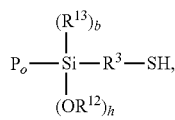
(Formula P9)

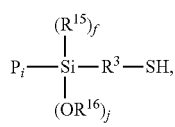
(Formula P10)

wherein in Formula P7:
P, x, y, r, $R^1$; $R^2$ and $R^3$ are as defined in Formula P1, and wherein x+y+r=3;
and wherein in Formula P8, Formula P9 and Formula P10:
P is a polymer chain comprising monomer units derived from at least one of the following monomer groups: butadiene, isoprene, styrene and alpha-methylstyrene, the number of monomer units per macromolecule ranging from 10 to 50,000 g/mol, preferably from 20 to 40,000 g/mol; O is an oxygen atom; Si is a silicon atom; S is a sulfur atom; H is a hydrogen atom; $R^3$ is at least divalent and is ($C_1$-$C_{18}$) alkyl, which may be substituted with one or more of the following groups: tertiary amine group, silyl group, ($C_7$-$C_{18}$) aralkyl group and ($C_6$-$C_{18}$) aryl group;
$R^1$, $R^{12}$ and $R^{16}$ are independently selected from a hydrogen atom and ($C_1$-$C_4$) alkyl;
$R^2$, $R^{13}$ and $R^{15}$ are each independently selected from ($C_1$-$C_{18}$) alkyl, g, h and j are each independently selected from an integer of 0, 1 and 2; b, d and f are each independently selected from an integer of 0, 1 and 2; and wherein
the sum of the letters p, b and g is 3 (p+b+g=3), the sum of the letters o, d and h is 3 (o+d+h=3) and the sum of the letters i, f and j is 3 (i+f+j=3).
In one preferred embodiment, $R^3$ is divalent and is ($C_1$-$C_{18}$) alkyl; $R^1$, $R^6$ or $R^{10}$ are independently selected from hydrogen and ($C_1$-$C_{18}$) alkyl; p, o or i are selected from an integer of 1 and 2; g, h or j are selected from an integer of 1 and 2; b, d or f are selected from an integer of 0 and 1.
While not explicitly shown in Formula P1 to P6, it will be understood that the silane sulfide modified macromolecular compounds of the present invention include their corresponding Lewis base adducts.
The proportion of thiol group-containing macromolecular compounds of Formula P7, Formula P8, Formula P9 and Formula P10 obtained in the process may vary considerably, depending on to the structure of the R-group in the (—($R^2$)$_y$Si—), (—Si$R^4R^8$—), (—Sn$R^4R^8$—), (—Si$R^4$=) and (—Sn$R^4$=) moieties of the macromolecular compound of Formula P1, Formula P2, Formula P3, Formula P4, Formula P5 and Formula P6. Alternatively, a water-free work up procedure can be used for the preparation of the silane sulfide modified macromolecular compounds of Formula P1, Formula P2, Formula P3, Formula P4, Formula P5 and Formula P6.

It is believed that the hydrocarbyloxysilyl (—SiOR) group of the modified macromolecular compound is reactive with fillers, such as silica and/or carbon black, preferably with silica, present. This interaction is believed to result in the formation of bonds with fillers, or in the case of some fillers, in electrostatic interactions, which result in more homogeneous distributions of filler within the polymer compositions.

Specific preferred modified macromolecular compounds based on Formula P1 to Formula P6 include the following polymers (and their corresponding Lewis base adducts):

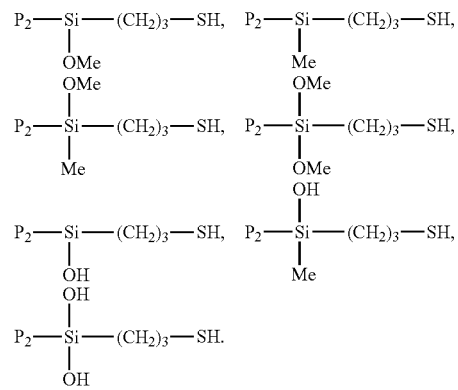

The reaction product, i.e. the polymer composition comprising silane sulfide modified macromolecular compound(s) of the present invention, typically comprises one or more alkoxysilyl or silanol group-containing compounds as represented by Formula P7, Formula P8, Formula P9 and Formula P10, typically in a total amount from 0.0001 to 1.50 mmol/gram of polymer, preferably from 0.0005 to 0.9 mmol/gram, and more preferably from 0.0010 to 0.5 mmol/gram, and even more preferably from 0.0020 to 0.1 mmol/gram of polymer.

The polymer composition comprising silane sulfide modified macromolecular compound(s) of the invention preferably comprises sulfide group-containing compounds, and the sulfide groups, in the form of hydrocarbylsilyl or hydrocarbylstannyl protective groups and/or thiol groups (sulfide and thiol groups), are typically present in a total amount of from 0.0001 to 0.50 mmol/gram of polymer, preferably from 0.0005 to 0.30 mmol/gram, and more preferably from 0.0010 to 0.20 mmol/gram, and even more preferably from 0.0020 to 0.10 mmol/gram of polymer. In another embodiment, the sulfide groups are present in an amount ranging from 0.0001 to 0.50 mmol/gram of polymer, preferably ranging from 0.0005 to 0.30 mmol/gram, and more preferably ranging from 0.0010 to 0.20 mmol/gram, and even more preferably from ranging from 0.0020 to 0.10 mmol/gram of polymer. In another embodiment, the thiol groups are present in an amount ranging from 0.0001 to 0.50 mmol/gram of polymer, preferably ranging from 0.0005 to 0.30 mmol/gram, and more preferably ranging from 0.0010 to 0.20 mmol/gram, and even more preferably from ranging from 0.0020 to 0.10 mmol/gram of polymer.

For most applications, the silane sulfide modified macromolecular compound is preferably a homopolymer derived from a conjugated diolefin, a copolymer derived from a conjugated diolefin monomer with an aromatic vinyl monomer, and/or a terpolymer of one or two types of conjugated diolefins with one or two types of aromatic vinyl compounds.

Although there are no specific limitations regarding the content of 1,2-bonds and/or 3,4-bonds (hereinafter called "vinyl bonds") of the conjugated diolefin portion in the polymer composition comprising the silane sulfide modified macromolecular compound(s) of the invention, for most applications the vinyl bond content is preferably from 10 to 90% by weight and particularly preferably from 15 to 80% by weight (based on the total weight of the polymer). If the vinyl bond content in a polymer composition is less than 10% by weight, the resulting product may have inferior wet skid resistance. If the vinyl content in the elastomeric polymer exceeds 90% by weight, the product may exhibit compromised tensile strength and abrasion resistance and a relatively large hysteresis loss.

Although there are no specific limitations regarding the amount of aromatic vinyl monomer used in the preparation of the modified macromolecular compounds of the present invention, in most applications the aromatic vinyl monomers constitute from 5 to 60% by weight of the total monomer content, and more preferably from 10 to 50% by weight (based on the total weight of the polymer). Values of less than 5% by weight may lead to reduced wet skid properties, abrasion resistance, and tensile strength; whereas values of more than 60% by weight may lead to increased hysteresis loss. The silane sulfide modified macromolecular compound may be a block or random copolymer, and preferably 40% by weight or more of the aromatic vinyl compound units are linked singly, and 10% by weight or less are "blocks" in which eight or more aromatic vinyl compounds are linked successively. Copolymers falling outside this range often exhibit increased hysteresis. The length of successively linked aromatic vinyl units can be measured by an ozonolysis-gel permeation chromatography method developed by Tanaka et al. (Polymer, Vol. 22, Pages 1721-1723 (1981)).

Depending on the specific polymer and desired end use application, the first polymer composition comprising at least one silane sulfide modified macromolecular compound of the resent invention, such as the polymer product obtained in the method of making said silane sulfide modified macromolecular compound, preferably has a Mooney viscosity (ML 1+4, 100° C., as measured in accordance with ASTM D 1646 (2004), in the range of from 0 to 150, preferably from 0 to 100, and more preferably in the range of from 20 to 100, as determined using a Monsanto MV2000 instrument. If the Mooney viscosity (ML 1+4, 100° C.) of the polymer is more than 150 MU, the processability (filler incorporation and heat build-up in the internal mixer, banding on the roll mill, extrusion rate, extrudate die swell, smoothness, etc.) is likely to be negatively affected because the compounding machinery used by the tire manufacturers are not designed to handle such high Mooney rubber grades, and the cost of processing increases. In some cases a Mooney viscosity (ML 1+4, 100° C.) of less than 20 may not be preferred due to increased tack and cold flow of the uncrosslinked elastomeric polymer, resulting in difficult handling, poor green strength and poor dimensional stability during storage. In some further cases, when the first polymer compositions comprising at least one silane sulfide modified macromolecular compound are used as a softener, compatibilizer or processing aid in polymer formulations, a Mooney viscosity (ML 1+4, 100° C.) of less than 20 may be preferred.

The preferred molecular weight distribution of the total polymer contained in the first polymer composition comprising at least one silane sulfide modified macromolecular compound, represented by the ratio of the weight average molecular weight to the number average molecular weight ($M_w/M_n$), ranges from 1.0 to 10.0, preferably from 1.1 to 8.0 and more preferably from 1.2 to 4.5.

Reactive Compounding

In a preferred embodiment, the first polymer composition, comprising at least one silane sulfide modified macromolecular compound, is combined and reacted with filler(s) selected from silica, carbon-silica dual phase filler, carbon black, carbon nano-tube filler, lignin, glass filler, layered silicates, such as magadiite, in some preferred embodiments comprising silica as main filler component, and vulcanization agent and, optionally, additional constituents, including, but not limited to, processing aids, oils, vulcanization agents, silane coupling agents and unmodified uncrosslinked elastomeric polymers, thus forming a second polymer composition comprising filler.

The first polymer composition comprises at least one silane sulfide modified macromolecular compound and optionally one or both of (i) oil (often referred to as oil extended polymer) and (ii) polymer which is not identical with the modified macromolecular compounds according to the invention. Polymers which are not identical with the modified macromolecular compounds of the invention may be by-produced in the process of preparation of the modified macromolecular compound (see above) and may result from blending modified macromolecular compound(s) (for example in the form as obtained after polymerization) in solution with another polymer solution, followed by solvent removal. The first polymer composition preferably contains at least 25% by weight of the silane sulfide modified macromolecular compound, based on the total polymer contained in the composition, more preferably at least 35% by weight and even more preferably at least 45% by weight. The remaining portion of the polymer contained in the polymer composition is unmodified elastomeric polymer or polymer modified in a manner other than according to the invention. Examples of preferred unmodified elastomeric polymers are listed in WO 2009/148932 and preferably include styrene-butadiene copolymer, natural rubbers, polyisoprene and polybutadiene. It is desirable that the unmodified polymers have a Mooney viscosity (ML 1+4, 100° C. as measured in accordance with ASTM D 1646 (2004)) in the range of from 20 to 200, preferably from 25 to 150.

Oils

Oils may be used in combination with the uncrosslinked elastomeric polymers to reduce viscosity or Mooney values, or to improve processability of the first and the second polymer compositions and various performance properties of (vulcanized) second polymer compositions.

Oil(s) can be added to the modified macromolecular compound prior to the end of the preparation process, or as a separate component of the first or second polymer composition preparation process. For representative examples and classification of the oils see WO 2009/148932 and U.S. 2005/0159513, each of which is incorporated herein by reference in its entirety.

Representative oils include but are not limited to MES (Mild Extraction Solvate), TDAE (Treated Distillate Aromatic Extract), RAE (Residual Aromatic Extract) including but not limited to T-RAE and S-RAE, DAE including T-DAE and NAP (light and heavy naphthenic oils), including but not limited to Nytex 4700, Nytex 8450, Nytex 5450, Nytex 832, Tufflo 2000, and Tufflo 1200. In addition, native oils, including but not limited to vegetable oils, can be used as extender oils. Representative oils also include functionalized variations of the aforementioned oils, particularly epoxidized or hydroxylated oils. The aforementioned oils comprise varying concentrations of polycyclic aromatic compounds, paraffinics, naphthenics and aromatics and have different glass transition temperatures. The above mentioned types of oils have been characterized (*Kautschuk Gummi Kunststoffe*, vol. 52, pages 799-805). In some embodiments, the MES, RAE and TDAE are extender oils for rubber.

Processing Aids

Processing aids can optionally be added to the first and to the second polymer compositions, but preferably to the second polymer composition of the present invention. Processing aids are usually added to reduce the first and/or second polymer composition viscosity. As a result, the mixing period is decreased and/or the number of mixing steps is reduced and, consequently, less energy is consumed and/or a higher throughput in the course of the rubber compound extrusion process is achieved. Representative processing aids which can optionally be used as a component in the first polymer compositions of the present invention are described in *Rubber Handbook, SGF, The Swedish Institution of Rubber Technology* 2000 and in Werner Kleemann, Kurt Weber, *Elastverarbeitung-Kennwerte und Berechnungsmethoden*, Deutscher Verlag fir Grundstoffindustrie (Leipzig, 1990), each of which is incorporated herein by reference in its entirety. Examples of representative possessing aids which can optionally be used as component in the first polymer compositions of the present invention can be classified as follows:

(A) fatty acids including but not limited to oleic acid, priolene, pristerene and stearic acid;

(B) fatty acid salts including but not limited to Aktiplast GT, PP, ST, T, T-60, 8, F; Deoflow S; Kettlitz Dispergator FL, FL Plus; Dispergum 18, C, E, K, L, N, T, R; Polyplastol 6, 15, 19, 21, 23; Struktol A50P, A60, EF44, EF66, EM16, EM50, WA48, WB16, WB42, WS180, WS280 and ZEHDL;

(C) dispersing agents and processing aids including but not limited to Aflux 12, 16, 42, 54, 25; Deoflow A, D; Deogum 80; Deosol H; Kettlitz Dispergator DS, KB, OX; Kettlitz-Mediaplast 40, 50, Pertac/GR; Kettlitz-Dispergator SI; Struktol FL and WB 212; and (D) dispersing agents for highly active white fillers including but not limited to Struktol W33 and WB42.

Bifunctionalized silanes and monofunctional silanes (herein also called "silane coupling agents") are also occasionally referred to as processing aids but are separately described below.

Silane Coupling Agents

In some embodiments, a silane coupling agent (used for compatibilization of polymer and fillers) is added to the polymer composition which contains at least one silane sulfide modified macromolecular compound as described herein and silica, layered silicate (such as but not limited to magadiite) or carbon-silica dual-phase filler, which may be used as filler component. The typical amount of a silane coupling agent added is from about 1 to about 20 parts by weight and, in some embodiments, from about 5 to about 15 parts by weight for 100 parts by weight of the total amount of silica and/or carbon-silica dual-phase filler.

Silane coupling agents can be classified according to Fritz Röthemeyer, Franz Sommer: *Kautschuk Technologie*, (Carl Hanser Verlag 2006):

(A) bifunctionalized silanes including but not limited to Si 230 $(EtO)_3Si(CH_2)_3Cl$, Si 225 $(EtO)_3SiCH=CH_2$, A189 $(EtO)_3Si(CH_2)_3SH$, Si 69 $[(EtO)_3Si(CH_2)_3S_2]_2$, Si 264 $(EtO)_3Si-(CH_2)_3SCN$ and Si 363 $(EtO)Si((CH_2-CH_2-O)_5(CH_2)_{12}CH_3)_2(CH_2)_3SH)$ (Evonic Industries AG); and (B) monofunctional silanes including but not limited to Si 203 $(EtO)_3-Si-C_3H_7$, and Si 208 $(EtO)_3-Si-C_8H_{17}$.

Further examples of silane coupling agents are given in WO 2009/148932 and include but are not limited to bis-(3-hydroxy-dimethylsilyl-propyl)tetrasulfide, bis-(3-hydroxy-dimethylsilyl-propyl)-disulfide, bis-(2-hydroxy-dimethylsilyl-ethyl)tetrasulfide, bis-(2-hydroxy-dimethylsilyl-ethyl) disulfide, 3-hydroxy-dimethylsilyl-propyl-N,N-dimethyl-thiocarbamoyltetrasulfide and 3-hydroxy-dimethylsilyl-propylbenzothiazole tetrasulfide.

Vulcanization Agents

Vulcanization agents, as described herein, are added to the first or second polymer composition, as described herein. The addition of the vulcanization agents to the first or second polymer composition represents the key criteria for the of the formation of the vulcanized polymer composition.

Sulfur, sulfur-containing compounds acting as sulfur-donors, sulfur-accelerator systems and peroxides are the most common vulcanizing agents. Examples of sulfur-containing compounds acting as sulfur-donors include but are not limited to dithiodimorpholine (DTDM), tetramethylthiuramdisulphide (TMTD), tetraethylthiuramdisulphide (TETD), and dipentamethylenthiuramtetrasulphide (DPTT). Examples of sulfur accelerators include but are not limited to amine derivates, guanidine derivates, aldehydeamine condensation products, thiazoles, thiuram sulphides, dithiocarbamates and thiophosphates. Examples of peroxides used as vulcanizing agents include but are not limited to di-tert.-butyl-peroxides, di-(tert.-butyl-peroxy-trimethyl-cyclohexane), di-(tert.-butyl-peroxy-isopropyl-)benzene, dichloro-benzoylperoxide, dicumylperoxides, tert.-butyl-cumyl-peroxide, dimethyl-di(tert.-butyl-peroxy)hexane, dimethyl-di(tert.-butyl-peroxy)hexine and butyl-di(tert.-butyl-peroxy)valerate (*Rubber Handbook, SGF, The Swedish Institution of Rubber Technology* 2000).

Further examples and additional information regarding vulcanizing agents can be found in Kirk-Othmer, *Encyclopedia of Chemical technology* $3^{rd}$, Ed., (Wiley Interscience, N.Y. 1982), volume 20, pp. 365-468, (specifically "Vulcanizing Agents and Auxiliary Materials" pp. 390-402).

A vulcanizing accelerator of the sulfene amide-type, guanidine-type, or thiuram-type can be used together with a vulcanizing agent as required. Other additives such as zinc white, vulcanization auxiliaries, aging preventives, processing adjuvants and the like may optionally be added. A vulcanizing agent is typically added to the polymer composition in an amount of from 0.5 to 10 parts by weight and, in some embodiments, from 1 to 6 parts by weight per 100 parts by weight of the total elastomeric polymer. Examples of vulcanizing accelerators and the amount of accelerator added with respect to the total polymer are given in WO 2009/148932. The expression "total polymer" refers to the sum of all individual amounts of different polymer types, including the silane sulfide modified (elastomeric) macromolecular compound.

Sulfur-accelerator systems may or may not comprise zinc oxide. Preferably zinc oxide is used as a component of the sulfur-accelerator system.

Fillers

Fillers are added to first polymer compositions for forming second polymer compositions. Second polymer compositions, once cured, form filler-containing vulcanized polymer compositions. Thus, second polymer compositions and products made therefrom as well as vulcanized polymer compositions made from second polymer compositions and products containing such vulcanized polymer compositions include filler which serves as a reinforcement agent. Carbon black, silica, carbon-silica dual-phase filler, clay (layered silicates), calcium carbonate, magnesium carbonate, lignin, carbon-nano-tubes, amorphous fillers, such as glass based fillers, starch based fillers and the like and combinations thereof are examples of suitable fillers. Examples of fillers are described in WO 2009/148932 fully incorporated herein by reference. Carbon black is manufactured by a furnace method, and in some embodiments a nitrogen adsorption specific surface area of 50-200 $m^2/g$ and DBP oil absorption of 80-200 ml/100 grams, for example, FEF; HAF, ISAF, or SAF class carbon black, is used. In some embodiments, high agglomeration type carbon black is used. Carbon black is typically added in an amount of from 2 to 100 parts by weight, in some embodiments from 5 to 100 parts by weight, in some embodiments from 10 to 100 parts by weight, and in some embodiments from 10 to 95 parts by weight per 100 parts by weight of the total elastomeric polymer.

Examples of silica fillers include but are not limited to wet process silica, dry process silica, synthetic silicate-type silica and combinations thereof. Silica with a small particle diameter and high surface area exhibits a high reinforcing effect. Small diameter, high agglomeration-type silica (i.e., having a large surface area and high oil absorptivity) exhibits excellent dispersibility in the elastomeric polymer composition, representing desirable properties and superior processability. An average particle diameter of silica, in terms of a primary particle diameter, is in some embodiments from 5 to 60 nm, and in some embodiments from 10 to 35 nm. Moreover, the specific surface area of the silica particles (measured by the BET method) is in some embodiments from 35 to 300 $m^2/g$. For examples of silica filler diameters, particle sizes and BET surfaces, see WO 2009/148932. Silica is added in an amount of from 10 to 100 parts by weight, in some embodiments from 30 to 100 parts by weight, and in some embodiments from 30 to 95 parts by weight for 100 parts by weight of the total elastomeric polymer. Silica fillers can be used in combinations with other fillers including but not limited to carbon black, carbon-silica dual-phase-filler, clay, calcium carbonate, carbon-nano-tubes, magnesium carbonate and combinations thereof.

Carbon black and silica may be added together; in which case the total amount of carbon black and silica added is from 30 to 100 parts by weight and, in some embodiments, from 30 to 95 parts by weight per 100 parts by weight of the total elastomeric polymer. As long as such fillers are homogeneously dispersed in the elastomeric composition, increasing quantities (within the above ranges) result in compositions having excellent rolling and extruding processability and vulcanized products (products comprising vulcanized polymer compositions) exhibiting favorable hysteresis loss properties, rolling resistance, improved wet skid resistance, abrasion resistance and tensile strength.

Carbon-silica dual-phase-filler may be used either independently or in combination with carbon black and/or silica in accordance with the present teachings. Carbon-silica dual-phase-filler can exhibit the same effects as those obtained by the combined use of carbon black and silica, even in the case where it is added alone. Carbon-silica dual-phase-filler is so called silica-coated-carbon black made by coating silica over the surface of carbon black, and is commercially available under the trademark CRX2000, CRX2002 or CRX2006 (products of Cabot Co.). Carbon-silica dual-phase-filler is added in the same amounts as described above with respect to silica. Carbon-silica dual-phase-filler can be used in combinations with other fillers including but not limited to carbon black, silica, clay, calcium carbonate, carbon-nano-tubes, magnesium carbonate and combinations thereof. In some embodiments, carbon black and silica, either individually or in combination, are used.

Silica, carbon black or carbon black-silica dual-phase-fillers or combinations thereof can be used in combination with natural fillers including but not limited to starch or lignin.

In some embodiments, the silica incorporated in second polymer compositions, in products and vulcanized polymer compositions made from second polymer compositions, and in products comprising such vulcanized polymer compositions has a surface area determined by nitrogen adsorption (hereinafter referred to as "N2A") of from 150 to 300 $m^2/g$. A silica having an N2A of less than 150 $m^2/g$ may lead to an unfavorably low reinforcing effect. A silica having an N2A of more than 300 $m^2/g$ may provide a rubber compound with an increased viscosity and a deteriorated processability. In case of carbon black incorporated into the second polymer composition, into products and vulcanized polymer compositions made from second polymer compositions and into products comprising such vulcanized polymer compositions, an N2A from 60 to 150 $m^2/g$ is suitable. Carbon black having an N2A of less than 60 $m^2/g$ leads to a low reinforcing effect. Carbon black having an N2A of more than 150 $m^2/g$ provides products and vulcanized polymer compositions made from second polymer compositions and products comprising such vulcanized polymer compositions with an increased hysteresis loss and a deteriorated processability.

Polymer Composition

The second polymer composition comprising filler in accordance with the present invention can be prepared by kneading the above-described first polymer composition (containing at least one modified macromolecular compound according to the invention as defined above and including oil-containing first polymer composition varieties), unmodified polymers or polymers modified in a manner other than according to the invention (including oil extended varieties) and filler(s) (carbon black, silica, carbon-silica dual-phase filler, etc.) and optionally processing aids, oils, silane coupling agents and other additives, in a kneader at 140° C. to 180° C., to form a "first stage" second composition containing filler.

Alternatively, second polymer compositions in accordance with the present invention can be prepared by kneading a polymer composition already containing at least one of the fillers (for example, carbon black, silica, carbon-silica dual-phase filler, etc.), formed as result of the modified macromolecular compound manufacturing process, and optionally processing aids, oils, silane coupling agents, fillers (for example, carbon black, silica, carbon-silica dual-phase filler, etc.) and other additives in a kneader at 140° C. to 180° C. to form a "first stage" second polymer composition containing filler. The formation of the "first stage" second polymer composition may comprise one or more mixing steps, preferably 2 to 7 mixing steps.

Since the silane sulfide modified macromolecular compound contained in the second polymer composition allows mixing at the given process conditions at a relatively low Mooney viscosity compared with a corresponding polymer composition not containing the silane sulfide modified macromolecular compound, the mixing throughput can be increased and/or the energy consumption per time unit can be decreased.

After cooling, vulcanizing agents such as sulfur, vulcanizing accelerators, optionally zinc oxide and the like are added to the "first stage" second composition, and the resulting mixture, also referred to as "second stage" second composition, is blended using a Brabender mixer, Banbury mixer or open roll mill to form the desired shape. The "second stage" second composition is then vulcanized at 140° C. to 180° C. to obtain a vulcanized article, also referred to as "vulcanized polymer composition" or "vulcanized elastomeric polymer composition".

Alternatively, vulcanizing agents such as sulfur, vulcanizing accelerators, optionally zinc oxide and the like can be added to the aforementioned first polymer composition, and the resulting mixture is blended using a Brabender mixer, Banbury mixer or open roll mill to form the desired shape, and the mixture is vulcanized at 140° C. to 180° C., to obtain a vulcanized article, also referred to as "vulcanized polymer composition" or as "vulcanized elastomeric polymer composition".

INDUSTRIAL APPLICATIONS

Since the "vulcanized elastomeric polymer compositions" of the present invention exhibit low rolling resistance, low dynamic heat build-up and superior wet skid performance, they are well suited for use in preparing tires, tire treads, side walls, and tire carcasses as well as other industrial products such as belts, hoses, vibration dampers and footwear components.

Silane Sulfide Modified Macromolecular Compound and Further Polymers

When the modified macromolecular compound of the present invention is prepared in a polymerization reaction, the living anionic elastomeric polymer is produced ("living polymer"). A portion, or all, of the living polymer is modified with the silane sulfide modifier of the present invention to produce the modified macromolecular compound of the invention. Non-modified polymer may be produced as well in the reaction. In addition, if the modification reaction is conducted by using a combination of the silane sulfide modifier of the invention and a further chain end-modifying compound or a coupling agent such as alkoxysilane, e.g., tetraethoxysilane, the resulting polymer composition comprises both the modified macromolecular compound(s) of the invention and further modified or non-modified polymers ("further polymer").

Examples of the living anionic elastomeric polymer to be modified in accordance with the present invention and of the further polymers include homopolymers of conjugated dienes, especially butadiene or isoprene, and random or block co- and terpolymers of at least one conjugated diene, especially butadiene or isoprene, with at least one conjugated diene or with at least one aromatic α-olefin, and especially styrene and 4-methylstyrene, aromatic diolefin, especially divinylbenzene. Especially preferred is the random copolymerization, optionally terpolymerization, of at least one conjugated diene with at least one aromatic α-olefin, and optionally at least one aromatic diolefin or aliphatic α-olefin, and especially butadiene or isoprene with styrene, 4-methylstyrene and/or divinylbenzene. Additionally, especially preferred is the random copolymerization of butadiene with isoprene.

Examples of the living anionic elastomeric polymer to be modified and of the further polymers include the following: BR—polybutadiene; butadiene/C1-C4-alkyl acrylate copolymers; IR—polyisoprene; SBR—styrene/butadiene copolymers with styrene contents of 1 to 60, preferably 10 to 50 weight percent, including SSBR wherein the polymer is prepared in solution; SIR—styrene/isoprene copolymers with styrene contents of 1 to 60, preferably 10 to 50 weight percent including SSIR wherein the polymer is prepared in solution; BRIR—butadiene/isoprene copolymers with isoprene contents of 1 to 60, preferably 10 to 50 weight percent including BRIR wherein the polymer is prepared in solution; IIR—isobutylene/isoprene copolymers; IBR—isoprene/butadiene copolymers; NBR—butadiene/acrylonitrile copolymers; HNBR—partially hydrogenated or fully hydrogenated NBR rubber, and mixtures of theses rubbers; modified EPDM. The acronym "EPDM" represents an ethylene/propylene/diene copolymer.

In one embodiment, the living polymer or further polymer is a polybutadiene.

In another embodiment, the living polymer or further polymer is a butadiene/styrene copolymer (SSBR) prepared in solution.

In another embodiment, the living polymer or further polymer is a isoprene/styrene copolymer (SSIR) prepared in solution.

In another embodiment, the living polymer or further polymer is a butadiene/isoprene copolymer (BRIR) prepared in solution.

In another embodiment, the living polymer or further polymer is a polyisoprene, including synthetic polyisoprene.

In another embodiment, the living polymer or further polymer is a styrene/butadiene copolymer with a styrene unit content from 1 to 60 weight percent, preferably from 10 to 50 weight percent, based on the total weight of the copolymer.

In another embodiment, the living polymer or further polymer is a styrene/butadiene copolymer with a 1,2-polybutadiene unit content from 5 to 70 weight percent, preferably from 50 to 70, or 5 to 25 weight percent, based on the total weight of polybutadiene unit fraction of the copolymer.

In another embodiment, the living polymer or further polymer is a styrene/isoprene copolymer with a styrene unit content from 1 to 60 weight percent, preferably from 10 to 50 weight percent, based on the total weight of the copolymer.

In another embodiment, the living polymer or further polymer is a styrene/isoprene copolymer with a 1,2-polyisoprene unit content from 5 to 70 weight percent, preferably from 50 to 70, or 5 to 25 weight percent, based on the total weight of polybutadiene unit fraction of the copolymer.

In another embodiment, the living polymer or further polymer is a butadiene/isoprene copolymer with an isoprene unit content from 0.1 to 70 weight percent, preferably from 5 to 50 weight percent, based on the total weight of the copolymer.

In another embodiment, the living polymer or further polymer is a isobutylene/isoprene copolymer. In another embodiment, the living polymer or further polymer is a partially hydrogenated butadiene.

In another embodiment, the living polymer or further polymer is a partially hydrogenated styrene-butadiene copolymer.

DEFINITIONS

As used herein, the term "alkyl" refers to an aliphatic group. The alkyl group may be linear, branched, cyclic or contain a combination of linear, branched and/or cyclic parts, and may be saturated or unsaturated. Examples of straight chain aliphatic hydrocarbon groups include methyl (Me), ethyl (Et), n-propyl (Pr), n-butyl (Bu), n-pentyl and n-hexyl, and examples of branched aliphatic hydrocarbon groups include isopropyl and tert-butyl.

The term "aryl" as used herein refers to an aromatic group which may contain two or more aromatic rings. Examples include phenyls, biphenyls and other benzenoid compounds, each optionally substituted with alkyl, alkoxy or other heteroatoms, such as oxygen-, nitrogen-, sulfur- and/or phosphorous-containing moieties.

The term "alkoxy" is understood to include methoxy (MeO), ethoxy (EtO), propoxy (PrO), butoxy (BuO), iso-propoxy (iPrO), isobutoxy (iBuO), pentoxy, and the like.

As used herein, the term "aralkyl" refers to a group containing at least one aromatic ring to an alkyl group.

The designation of $(C_a-C_b)$, for example $(C_1-C_{12})$, as used herein is intended to mean a range of the number of carbon atoms of from a to b and includes all individual values and subranges from a to b.

The term "hydrocarbon groups" is understood to include any group, including saturated, unsaturated, linear, branched, cyclic and aromatic groups, which only consists of the elements hydrogen and carbon.

EXAMPLES

The following Examples are provided in order to further illustrate the invention, and are not to be construed as limiting. The examples describe the preparation of silane sulfide modifiers; the preparation and testing of modified (elastomeric) polymers (i.e. polymer compositions containing a silane sulfide modified macromolecular compound of the present invention); and the preparation and testing of uncrosslinked polymer compositions, including the first polymer composition and second polymer composition, as well as of crosslinked or cured polymer compositions, also referred to as vulcanized polymer compositions. Unless stated otherwise, all parts and percentages are expressed on a weight basis. The term "overnight" refers to a time of approximately 16-18 hours, and "room temperature" refers to a temperature of about 20-25° C. The polymerizations were performed under exclusion of moisture and oxygen, in a nitrogen atmosphere.

The vinyl content in the conjugated diolefin part was additionally determined by IR absorption spectrum (Morello method, IFS 66 FT-IR spectrometer of Bruker Analytic GmbH). The IR samples were prepared using $CS_2$ as swelling agent.

Bonded styrene content: A calibration curve was prepared by IR absorption spectrum (IR (IFS 66 FT-IR spectrometer of Bruker Analytik GmbH). The IR samples were prepared using $CS_2$ as swelling agent.). For the IR determination of the bound styrene in styrene-butadiene copolymers, four bands are assessed: a) band for trans-1,4-polybutadiene units at 966 $cm^{-1}$, b) band for cis-1,4-polybutadiene units at 730 $cm^{-1}$, c) band for 1,2-polybutadiene units at 910 $cm^{-1}$ and band for bound styrene (styrene aromatic bond) at 700 $cm^{-1}$. The band heights are normalized according to the appropriate extinction coefficients and summarized to a total of 100%. The normalization is done via $^1$H- and $^{13}$C-NMR. The styrene content was alternatively determined by NMR (NMR (Avance 400 device ($^1$H=400 MHz; $^{13}$C=100 MHz) of Bruker Analytik GmbH)).

The 1D NMR spectra were collected on a BRUKER Avance 200 NMR spectrometer (BRUKER BioSpin GmbH), using a "5 mm Dual detection probe." The field homogeneity was optimized by maximizing the deuterium lock signal. The samples were shimmed by optimizing the deuterium lock signal. The samples were run at room temperature (298 K). The following deuterated solvents were used: C6D6 (7.16 ppm for 1H; 128.06 ppm for 13C), CDCl3 (7.24 ppm for 1H; 77.03 ppm for 13C), d8-THF (1.73, 3.58 ppm for 1H; 25.35 ppm for 13C), the signals of the remaining protons of deuterated solvents were each used as an internal reference.

For spectral processing, the BRUKER 1D WINNMR software (version 6.0) was used. Phasing, base line correction and spectral integration of the resulting spectra was done in the manual mode. For acquisition parameters see Table 1.

TABLE 1

1D-NMR acquisition parameters using BRUKER standard pulse sequences

| | 1H-NMR | 13C-NMR | 29Si-NMR |
|---|---|---|---|
| Observe frequency | 400.130 MHz | 100.613 MHz | 74.495 |
| Spectral width | 8278.146 Hz | 23980.814 Hz | 31847.133 Hz |
| BRUKER Pulse program | Zg30 | Zgpg30 | Zgig |
| Pulse angle | 30° | 30° | 30° |
| Relaxation delay | 1.0 s | 2.0 s | 60 s |
| Number of Data points for FT | 32K | 32K | 32K |
| Line broadening | 0.3 Hz | 1 Hz | 1 Hz |
| Number of accumulated scans | 64 | >1000 | >1000 |

GPC-Method: SEC calibrated with narrow distributed polystyrene standard.

Sample Preparation:
a1) Oil free polymer samples:
About "9-11 mg" dried polymer sample (moisture content <0.6%) was dissolved in 10 mL tetrahydrofuran, using a brown vial of 10 mL size. The polymer was dissolved by shaking the vial for 20 min at 200 u/min.
a2) Oil containing polymer samples:
About "12-14 mg" dried polymer sample (moisture content <0.6%) was dissolved in 10 mL tetrahydrofuran, using a brown vial of 10 mL size. The polymer was dissolved by shaking the vial for 20 min at 200 u/min.
b) Polymer solution was transferred into a 2 ml vial using a 0.45 µm disposable filter.
c) The 2 ml vial was placed on a sampler for GPC-analysis.
Elution rate: 1.00 mL/min
Injection volume: 100.00 µm (GPC-method B 50.00 µm)
The measurement was performed in THF at 40° C. Instrument: Agilent Serie 1100/1200;
Module setup: Iso pump, autosampler, thermostat, VW—Detector, RI—Detector, Degasser; Columns PL Mixed B/HP Mixed B.

In each GPC-device 3 columns were used in an connected mode. The length of each of the columns: 300 mm; Column Type: 79911 GP-MXB, Plgel 10 µm MIXED-B GPC/SEC Columns, Fa. Agilent Technologies (eigentlicher Hersteller ist auch Polymer Laboratories)
GPC Standards: EasiCal PS-1 Polystyrene Standards, Spatula A+B
Styrene Standard Manufacturer:
Polymer Laboratories Polymer Laboratories
Now entity of Varian, Inc. Varian Deutschland GmbH
Website: http://www.polymerlabs.com Polydispersity (Mw/Mn) was used as a measure for the width of molecular weight distribution. The calculation of Mw and Mn (weight average molecular weight (Mw) and number average molecular weight (Mn)) was based on one of two procedures.

The Mp1, Mp2, Mp3 correspond to the (maximum peak) molecular weight measured at the first, second or third peaks of the GPC curve [the first peak Mp1 (lowest molecular weight) is located on the right side of the curve, and the last peak (highest molecular weight) is located on the left side of the curve], respectively. Maximum peak molecular weight means the molecular weight of the peak at the position of maximum peak intensity. The Mp2 and Mp3 are two or three polymer chains coupled to one macromolecule. Mp1 is one polymer chain (base molecular weight—no coupling of two or more polymer chains to one macromolecule).

The total coupling rate represents the sum of the weight fractions of coupled polymers relative to the total polymer weight, including the sum of the weight fractions of all coupled polymers and the uncoupled polymer. The total coupling rate is calculated as shown below.

CR(total)=(ΣArea fraction of all coupled peaks [Peak with maximum Mp2 to peak with highest indexed peak maximum])/(ΣArea fraction of all peaks [Peak with peak maximum Mp1 to peak with highest indexed peak maximum]).

The individual coupling rate (e.g. two polymer arms coupled corresponding to the peak with peak maximum Mp2) is calculated as depicted below:

CR(2arms)=(Area fraction of peak with peak maximum Mp2)/(ΣArea fraction of all peaks [Peak with peak maximum Mp1 to peak with highest indexed peak maximum]).

Modification efficiency with sulfanylsilanes was determined via (—SiMe$_3$) group and (—Si—OMe) group concentration by NMR technique (NMR (Avance 400 device ($^1$H=400 MHz; $^{13}$C=100 MHz) of Bruker Analytic GmbH). (—Si—OMe) signal at 3.3-3.5. ppm and (—SiMe$_3$) signal at 0.1-0.2 ppm. To determine the modification efficiency with an alkoxy group containing sulfanylsilane compound in percent, the value was divided by the number average molecular weight (Mn) measured by GPC, as the measured value is the amount of the Si—C bond per unit weight.

Modification efficiency with sulfanylsilanes was also determined via sulfur content as sulfate. The procedure required combustion of the sample in an automatic oven (Combustor 02 of the company GAMAB, Germany, Bad Dürrenberg) followed by absorption of the flue gas in water with 0.1% hydrazinium hydroxide and subsequent determination of the sulfate concentration with ion chromatography (Metrohm, column: Dionex IonPac AS12A.

Rubber compounds were prepared by combining the constituents listed below in Tables 4, 8 and 12 in a "380 cc Banbury mixer (Labstation 350S from Brabender GmbH&Co KG)," following a two-stage mixing process. Stage 1—mixed all components together, except the components of the vulcanization package, to form a stage 1 formulation. Stage 2—components of vulcanization package were mixed into stage 1 formulation to form a stage 2 formulation.

Mooney viscosity was measured according to ASTM D 1646 (2004), with a preheating time of one minute and a rotor operation time of 4 minutes, at a temperature of 100° C. [ML1+4(100° C.)], on a MV 2000E from Alpha Technologies UK. The rubber Mooney viscosity measurement is performed on dry (solvent free) raw polymer (unvulcanized rubber). The Mooney values of the raw polymers are listed in Table 3. The Compound Moony viscosity is measured on an uncured (unvulcanized) second state polymer compound sample prepared according to Tables 4, 8 and 12. The Compound Mooney values are listed in Tables 7, 11 and 15.

Measurement of unvulcanized rheological properties was performed according to ASTM D 5289-95 (reapproved 2001), using a rotor-less shear rheometer (MDR 2000 E from Alpha Technologies UK) to measure Scorch Time (TS) and Time to Cure (TC). The rheometer measurement was performed at a constant temperature of 160° C. on a non-vulcanized second stage polymer formulation, according to Tables 5, 9 and 13. The amount of polymer sample is about 4.5 g. Sample shape and shape preparation are standardized and defined by the measurement device (MDR 2000 E from Alpha Technologies UK).

The "TC 50" and "TC 90" values are the respective times required to achieve 50% and 90% conversion of the vulcanization reaction. The torque is measured as a function of time of reaction. The vulcanization conversion is automatically calculated from the generated torque versus time curve. The "TS 1" and "TS 2" values are the respective times required to increase the torque by 1 dNm and 2 dNm above the respective torque minimum (ML) during vulcanization. Preferably TS 1 is >1.5 minute, TS 2 is >2.5 minute, TC 50 is from 3 to 8 minutes, and TC 90 is from 8 to 19 minutes.

Tensile Strength, Elongation at Break and Modulus at 300% Elongation (Modulus 300) were measured according to ASTM D 412-98A (reapproved 2002), using a dumbbell die C test piece on a Zwick Z010. Of the standardized dumbbell die C test pieces, those of "2 mm thickness" were used. The tensile strength measurement was performed at room temperature, on a cured (vulcanized) second stage polymer sample, prepared according to Tables 6, 10 and 14. Stage 2 formulations were vulcanized within 16-25 minutes at 160° C. to TC 95 (95% vulcanization conversion) (see cure data in Tables 5, 9 and 13).

Heat build-up was measured according to ASTM D 623, method A, on a Doli 'Goodrich'-Flexometer. The heat build-up measurement was performed on a vulcanized second stage polymer samples according to Tables 5, 9 and 13. Stage 2 formulations were vulcanized at 160° C. to TC 95 (95% vulcanization conversion) (see cure data in Tables 5, 9 and 13).

Tan δ at 60° C. and tan δ at 0° C. as well as tan δ at −10° C. measurements were performed on cylindrical specimen, using a dynamic mechanical thermal spectrometer "Eplexor 150N," manufactured by Gabo Qualimeter Testanlagen GmbH (Germany), by applying a compression dynamic strain of 0.2%, at a frequency of 2 Hz, at the respective temperatures. The smaller the index at a temperature of 60° C., the lower the rolling resistance (lower=better). Tan δ (0° C.) was measured using the same equipment and load conditions at 0° C. The larger the index at this temperature, the better the wet skid resistance (higher=better). Tan δ at 60° C. and tan δ at 0° C. as well as tan δ at −10° C. were determined (see Tables 6, 10 and 14). Stage 2 formulations were vulcanized at 160° C. to TC 95 (95% vulcanization conversion) (see cure data in Tables 5, 9 and 13). The process leads to the formation of visually "bubble free," homogeneous cured rubber disc of "60 mm diameter" and "10 mm height." A specimen was drilled out of the aforementioned dish and has a size of "10 mm diameter" and "10 mm height."

DIN abrasion was measured according to DIN 53516 (1987-06-01). The larger the index, the lower the wear resistance (lower=better). The abrasion measurement was performed on a vulcanized, second stage polymer formulation according to Tables 5, 9 and 13.

In general, the higher the values for Elongation at Break, Tensile Strength, Modulus 300, and tan δ at 0° C., the better the sample performance; whereas the lower the Tan δ at 60°

C., Heat Build Up and Abrasion, the better the sample performance. Preferably TS 1 is >1.5 minute, TS 2 is >2.5 minute, TC 50 is from 3 to 8 minutes, and TC 90 is from 8 to 19 minutes.

Modifier Preparation: Six Modifiers and one Coupling Agent were used in the Examples. The structural formula and method of preparation (or source for obtaining) are provided below. Modifiers 3, 4, 5 and 6 are representative of those of the present invention, whereas modifiers 1 and 2 are for comparative purposes.

Coupling Agent

Coupling Agent C1 is represented by Formula C1. Tin tetrachloride (C1) was purchased from Aldrich. SnCl$_4$ (Formula C1)

Further Modifier Agents

Modifier 1 is represented by Formula M1 below and was prepared as follows:

(Formula M1)

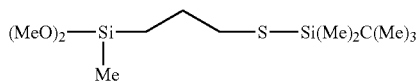

Preparation Pathway 1 (M1):

To a 100 mL Schlenk flask was charged 25 ml tetrahydrofuran (THF), 79.5 mg (10 mmol) lithium hydride, and subsequently, 1.18 g (10 mmol) gamma-mercaptopropyl (methyl) dimethoxysilane P1 from the ABCR GmbH. The reaction mixture was stirred for 24 hours at room temperature, and another two hours at 50° C. Than tert-butyl dimethyl chloro silane (1.51 g (10 mmol)) was dissolved in 10 g THF, and the resulting solution was then added drop wise to the Schlenk flask. Lithium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 99% pure per GC, and therefore no further purification was necessary. A yield of 3.1 g (9.3 mmol) of modifier M1 was obtained.

Preparation Pathway 2 (M1):

To a 100 mL Schlenk flask was charged 1.18 g (10 mmol) gamma-mercaptopropyl (methyl) dimethoxysilane P1 from the ABCR GmbH, 25 ml tetrahydrofuran (THF), and subsequently, 0.594 g (11 mmol) sodium methanolate (NaOMe) dissolved in 10 mL THF. The reaction mixture was stirred for 18 hours at room temperature. Then tert-butyl dimethyl chloro silane (1.51 g (10 mmol)) was dissolved in 10 g THF, and the resulting solution was then added drop wise to the Schlenk flask. Sodium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 89% pure per GC. Further purification consisted in a fractionated distillation, and a yield of 2.6 g (7.9 mmol) of modifier M1 was obtained.

Modifier 2 is represented by Formula M2 below and was prepared as follows:

(Formula M2)

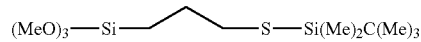

Preparation Pathway 1 (M2):

To a 100 mL Schlenk flask was charged 25 ml tetrahydrofuran (THF), 79.5 mg (10 mmol) lithium hydride, and subsequently, 1.96 g (10 mmol) gamma-mercaptopropyl trimethoxy silane P2 [Silquest A-189] from the Cromton GmbH. The reaction mixture was stirred for 24 hours at room temperature, and another two hours at 50° C. Than tert-butyl dimethyl chloro silane (1.51 g (10 mmol)) was dissolved in 10 g THF, and the resulting solution was then added drop wise to the Schlenk flask. Lithium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 99% pure per GC, and therefore no further purification was necessary. A yield of 2.9 g (9.2 mmol) of modifier M2 was obtained.

Alternative Preparation Pathway 2 (M2):

To a 100 mL Schlenk flask was charged 1.96 g (10 mmol) gamma-mercaptopropyl trimethoxy silane P2 [Silquest A-189] from the Cromton GmbH, 25 ml tetrahydrofuran (THF), and subsequently, 0.594 g (11 mmol) sodium methanolate (NaOMe) dissolved in 10 mL THF. The reaction mixture was stirred for 18 hours at room temperature. Then tert-butyl dimethyl chloro silane (1.51 g (10 mmol)) was dissolved in 10 g THF, and the resulting solution was then added drop wise to the Schlenk flask. Sodium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 89% pure per GC. Further purification consisted in a fractionated distillation, and a yield of 2.2 g (7.2 mmol) of modifier M2 was obtained.

Alternative Preparation Pathway 3 (M2):

A 500 mL Schlenk flask was charged with 100 g cyclohexane, 8.6 g (85 mmol) triethylamine and 13.12 g (80 mmol) gamma-mercaptopropyl trimethoxy silane [Silquest A-189] from the Cromton GmbH. 24.91 g (165 mmol) tert-butyl dimethyl chloro silane were diluted with 170 g cyclohexane and the resulting solution is then added drop wise to the Schlenk flask. Immediately a white triethylammonium chloride precipitated. The suspension was stirred for about 24 hours at room temperature and for another three hours at 60° C. The white precipitate was subsequently separated by filtration. The resulting colorless solution was distilled in the vacuum to yield 20.7 g (67.7 mmol) of modifier M2.

Silane Sulfide Modification Agents

Modifier 3 is represented by Formula M3 below and was prepared as follows:

(Formula M3)

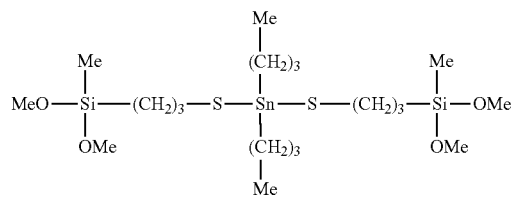

Preparation Pathway 1:

To a 100 mL Schlenk flask was charged 50 ml tetrahydrofuran (THF), 159 mg (20 mmol) lithium hydride, and subsequently, 3.6 g (20 mmol) gamma-mercaptopropyl (methyl) dimethoxysilane P1 from the ABCR GmbH. The reaction mixture was stirred for 2 hours at 65° C. The reaction mixture was allowed to cool down to room temperature. Then a solution of di-n-butyl dichloro stannane (3.3 g (10 mmol)) in 10 g THF was then added drop wise to the Schlenk flask. The reaction mixture was warmed up to 65° C. and kept at this temperature for 2 hours. Subsequently the THF solvent was removed under vacuum (reduced pressure) from the resulting mixture at room temperature and the residue was dissolved in 50 mL cyclohexane. Precipitated lithium chloride was separated from the reaction product dissolved in the cyclohexane by filtration. The cyclohexane solvent was removed under vacuum (under reduced pressure). The resulting colorless liquid solution proved to be 89% pure per GC, and therefore no further purification was necessary. A yield of 5.5 g (8.9 mmol) of modifier M3 was obtained.

Preparation Pathway 2:

To a 100 mL Schlenk flask was charged 100 ml cyclohexane, 2.02 g (20 mmol) triethyl amine, and 3.6 g (20 mmol) gamma-mercaptopropyl (methyl) dimethoxysilane P1 from the ABCR GmbH. The reaction mixture was stirred for 5 min at room temperature. Then a solution of di-n-butyl dichloro stannane (3.30 g (10 mmol)) in 20 g cyclohexane was then added drop wise to the Schlenk flask. The reaction mixture was warmed up to 65° C. and kept at this temperature for 2 hours. Precipitated triethyl ammonium chloride was separated from the reaction product dissolved in the cyclohexane by filtration. Then cyclohexane solvent was removed under vacuum (under reduced pressure). The resulting colorless liquid solution proved to be 95% pure per GC, and therefore no further purification was necessary. A yield of 5.9 g (9.5 mmol) of modifier M3 was obtained.

$^1$H-NMR (400 MHz, 23° C., $C_6D_6$): δ=3.35 (s, 12H, $SiOCH_3$), 2.82 (t, 4H, $S—CH_2CH_2CH_2—Si$), 1.87 (m, 4H, $CH_2CH_2CH_2—Si$), 1.61 (m, 4H, $SnCH_2CH_2CH_2CH_3$), 1.30 (m, 8H, $SnCH_2CH_2CH_2CH_3$), 0.83 (t, 6H, $SnCH_2CH_2CH_2CH_3$), 0.78 (t, 4H, $S—CH_2CH_2CH_2—Si$), 0.06 (s, 6H, $Si(OMe)_2CH_3$) ppm;

$^{13}$C (101 MHz, 23° C., $C_6D_6$): δ=49.95 ($OCH_3$), 31.01 ($S—CH_2CH_2CH_2—Si$), 28.70 ($SCH_2CH_2CH_2$) & ($SnCH_2CH_2CH_2CH_3$), 27.06 ($SnCH_2CH_2CH_2CH_3$), 17.90 ($SnCH_2CH_2CH_2CH_3$), 13.76 ($SnCH_2CH_2CH_2CH_3$), 13.21 ($S—CH_2CH_2CH_2—Si$), −5.47 ($SiCH_3$) ppm.

Modifier 4 is represented by Formula M4 below and was prepared as follows:

(Formula M4)

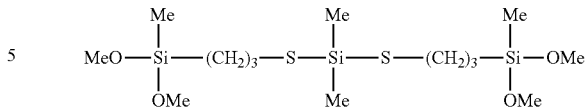

Preparation Pathway 1:

To a 100 mL Schlenk flask was charged 50 ml tetrahydrofuran (THF), 159 mg (20 mmol) lithium hydride, and subsequently, 3.6 g (20 mmol) gamma-mercaptopropyl (methyl) dimethoxysilane P1 from the ABCR GmbH. The reaction mixture was stirred for 2 hours at 65° C. The reaction mixture was allowed to cool down to room temperature. Then a solution of dimethyl dichloro silane (1.30 g (10 mmol)) in 10 g THF was then added drop wise to the Schlenk flask. The reaction mixture was warmed up to 65° C. and kept at this temperature for 2 hours. Subsequently the THF solvent was removed under vacuum (reduced pressure) from the resulting mixture at room temperature and the residue was dissolved in 50 mL cyclohexane. Precipitated lithium chloride was separated from the reaction product dissolved in the cyclohexane by filtration. The cyclohexane solvent was removed under vacuum (under reduced pressure). The resulting colorless liquid solution proved to be 95% pure per GC, and therefore no further purification was necessary. A yield of 3.9 g (9.3 mmol) of modifier M4 was obtained.

Preparation Pathway 2:

To a 250 mL Schlenk flask was charged 150 mL cyclohexane, 5.05 g (50 mmol) triethyl amine, 9.02 g (50 mmol) gamma-mercaptopropyl (methyl) dimethoxysilane P1 from the ABCR GmbH, and subsequently, 3.23 g (25 mmol) dimethyl dichloro silane from Sigma-Aldrich. The reaction mixture was stirred overnight at 65° C. The reaction mixture was allowed to cool down to room temperature. The mixture was filtered and all volatiles were removed under reduced pressure to yield 9.20 g (88%) of compound M4. The resulting colorless liquid solution of modifier M4 proved to be 95% pure per NMR, and therefore no further purification was necessary.

$^1$H-NMR (400 MHz, 23° C., $C_6D_6$): δ=3.32 (s, 12H, $SiOCH_3$), 2.57 (t, 4H, $S—CH_2$), 1.70 (m, 4H, $CH_2CH_2CH_2$), 0.66 (m, 4H, $CH_2SiMe(OMe)_2$), 0.43 (s, 6H, $Si(OMe)CH_3$), 0.01 (s, 6H, $Si(OCH_3)_2CH_3$) ppm; $^{13}$C (101 MHz, 23° C., $C_6D_6$): δ=49.96 ($OCH_3$), 30.90 ($S—CH_2$), 26.67 ($CH_2CH_2CH_2$), 13.15 ($CH_2SiMe(OMe)_2$), 2.06 ($SiCH_3$), −5.48 ($SiCH_3$) ppm.

Modifier 5 is represented by Formula M5 below and was prepared as follows:

(Formula M5)

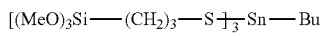

Preparation Pathway:

To a 100 mL Schlenk flask was charged 50 ml tetrahydrofuran (THF), 360 mg (45.25 mmol) lithium hydride, and subsequently, 4.0 g (20.37 mmol) gamma-mercaptopropyl (methyl) dimethoxysilane P1 from the ABCR GmbH. The reaction mixture was stirred for 1.5 hours at 25° C. Then a solution of n-butyl trichloro stannane (1.915 g (6.79 mmol)) in 10 g THF was then added drop wise to the Schlenk flask. The reaction mixture was warmed up to 65° C. and kept at this temperature for 1.5 hours. Subsequently the THF solvent was removed under vacuum (reduced pressure) from the resulting mixture at room temperature and the residue was dissolved in 50 mL pentane. Precipitated lithium chloride was separated from the reaction product dissolved in the pentane by filtration. The pentane solvent was removed under vacuum (under reduced pressure). The resulting colorless liquid solution proved to be pure per NMR, and therefore no further purification was necessary. A yield of 4.3 g (5.5 mmol) of modifier M5 was obtained.

$^1$H-NMR (400 MHz, 23° C., $C_6D_6$): δ=3.42 (s, 27H, SiOCH$_3$), 2.93 (t, 6H, S—CH$_2$CH$_2$CH$_2$—Si), 1.93 (m, 6H, CH$_2$CH$_2$CH$_2$—Si), 1.47 (m, 2H, SnCH$_2$CH$_2$CH$_2$CH$_3$), 1.44 (m, 2H, SnCH$_2$CH$_2$CH$_2$CH$_3$), 1.18 (m, 2H, SnCH$_2$CH$_2$CH$_3$), 0.80 (t, 3H, SnCH$_2$CH$_2$CH$_2$CH$_3$), 0.77 (t, 6H, S—CH$_2$CH$_2$CH$_2$—Si) ppm;

$^{13}$C (101 MHz, 23° C., $C_6D_6$): δ=50.34 (OCH$_3$), 31.56 (S—CH$_2$CH$_2$CH$_2$—Si), 28.28 (SCH$_2$CH$_2$CH$_2$—Si), 27.58 (SnCH$_2$CH$_2$CH$_2$CH$_3$), 26.16 (SnCH$_2$CH$_2$CH$_2$CH$_3$), 13.48 (SnCH$_2$CH$_2$CH$_2$CH$_3$), 9.08 (S—CH$_2$CH$_2$CH$_2$—Si) ppm.

Modifier 6 is represented by Formula M6 below and was prepared as follows:

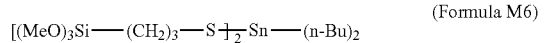

(Formula M6)

Preparation Pathway:

To a 250 mL Schlenk flask was charged 100 ml tetrahydrofuran (THF), 716 mg (90.0 mmol) lithium hydride, and subsequently, 8.835 g (45 mmol) gamma-mercaptopropyl trimethoxy silane P2 [Silquest A-189] from the Cromton GmbH. The reaction mixture was stirred for 2 hours at 25° C. Then a solution of di-n-butyl dichloro stannane (6.84 g (22.5 mmol)) in 50 g THF was then added drop wise to the Schlenk flask. The reaction mixture was warmed up to 65° C. and kept at this temperature for 1.25 hours. Subsequently the THF solvent was removed under vacuum (reduced pressure) from the resulting mixture at room temperature and the residue was dissolved in 100 mL pentane. Precipitated lithium chloride was separated from the reaction product dissolved in the pentane by filtration. The pentane solvent was removed under vacuum (under reduced pressure). The resulting colorless liquid solution proved to be 83% pure per NMR. A yield of 10.4 g (16.7 mmol) of modifier agent M6 was obtained, when calculated for isolated pure modifier M6.

$^1$H-NMR (400 MHz, 23° C., $C_6D_6$): δ=3.43 (s, 18H, SiOCH$_3$), 2.87 (t, 4H, S—CH$_2$CH$_2$CH$_2$—Si), 1.98 (m, 4H, CH$_2$CH$_2$CH$_2$—Si), 1.64 (m, 4H, SnCH$_2$CH$_2$CH$_2$CH$_3$), 1.30 (m, 8H, SnCH$_2$CH$_2$CH$_2$CH$_3$), 0.88 (t, 6H, SnCH$_2$CH$_2$CH$_2$CH$_3$), 0.78 (t, 4H, S—CH$_2$CH$_2$CH$_2$—Si) ppm;

$^{13}$C (101 MHz, 23° C., $C_6D_6$): δ=50.34 (OCH$_3$), 28.59 (S—CH$_2$CH$_2$CH$_2$—Si), 28.68 (SCH$_2$CH$_2$CH$_2$—Si), 30.79 (SnCH$_2$CH$_2$CH$_2$CH$_3$), 27.04 (SnCH$_2$CH$_2$CH$_2$CH$_3$), 17.88 (SnCH$_2$CH$_2$CH$_2$CH$_3$), 13.73 (SnCH$_2$CH$_2$CH$_2$CH$_3$), 9.25 (S—CH$_2$CH$_2$CH$_2$—Si) ppm.

Modifier Precursor Compounds

Gamma-mercaptopropyl (methyl) dimethoxysilane represented by Formula PR1 below, and was purchased from the ABCR GmbH.

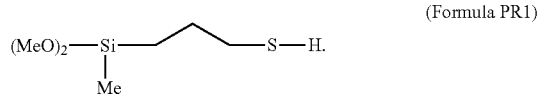

(Formula PR1)

Gamma-mercaptopropyl trimethoxy silane represented by Formula PR2 below, and was purchased from Cromton GmbH.

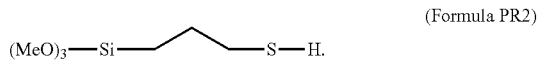

(Formula PR2)

Copolymerization of 1,3-Butadiene with Styrene (Examples 3-28)

The co-polymerizations were performed in a double wall 20 liter steel reactor which was first purged with nitrogen before the addition of organic solvent, monomers, polar coordinator compound, initiator compound or other components. The polymerization reactor was tempered to 40° C. unless stated otherwise. The following components were then added in the following order: cyclohexane solvent (9000 grams); butadiene monomer, styrene monomer, tetramethylethylene diamine (TMEDA), and the mixture was stirred for one hour followed by titration with n-butyl lithium to remove traces of moisture or other impurities. Additional n-butyl lithium was added as to start the polymerization reaction. The polymerization was performed for 80 minutes not allowing the polymerization temperature to exceed 60° C. Afterwards, 0.5% of the total butadiene monomer amount was added followed by the addition of either the coupling agent or the modifier (1, 2, 3, 4, 5 or 6) unless stated otherwise. For the termination of the polymerization process, the polymer solution was transferred after 45 minutes into a separate double wall steel reactor containing 100 mL ethanol and 1.4 g of concentrated HCl (concentration 36%) and 5 g Irganox 1520 as stabilizer for the polymer. This mixture was stirred for 15 minutes. The resulting polymer solution was than stripped with steam for 1 hour to remove solvent and other volatiles and dried in an oven at 70° C. for 30 minutes and another one to three days at room temperature.

The polymerization components are summarized in Table 2, the resulting polymer characteristics in Table 3, the components of the polymer composition are summarized in Tables 4, 8 and 12 below. Unless otherwise stated, quantities in Table 2 are expressed in mmols. Quantities in Tables 4, 8 and 12 are expressed in phr (parts per hundred parts of the total rubber component of the composition). Examples of polymers applied to the preparation of polymer compositions according to the recipes shown in Tables 4, 8 and 12 under identical process conditions (in the same Banbury mixer, under identical process temperatures and timelines, on the same day by the same operator) are designated with identical letters adjacent to the Example number (e.g. 3A, 4A).

The use of a dash "-" in the tables below indicates that no constituent was added. The abbreviation "N.M." is intended to mean that no measurement was taken or that corresponding data was unavailable.

TABLE 2

Composition of Examples

| Example | Modifier Used as Chain-End Modification Agent | Modifier Used as Modifying Coupling Agent | Coupling Agent | butadiene (moles) | styrene (moles) | TMEDA | n-butyl lithium |
|---|---|---|---|---|---|---|---|
| 1 [Ref] | (M1) 3.63 | — | (C1) 0.31 | 13.10 | 1.74 | 8.66 | 4.33 |
| 2 | (M1) 3.94 | (M2) 0.50 | — | 12.99 | 1.79 | 8.94 | 4.48 |
| 3 | — | (M3) 2.19 | — | 13.12 | 1.82 | 8.76 | 4.33 |
| 4 [Ref] | (M1) 3.63 | — | (C1) 0.31 | 13.10 | 1.74 | 8.66 | 4.33 |
| 5 [Ref] | (M1) 3.94 | (M2) 0.50 | — | 12.97 | 1.79 | 8.94 | 4.48 |
| 6 | (M1) 3.90 | (M3) 2.45 | — | 13.09 | 1.82 | 8.94 | 4.48 |
| 7 [Ref.] | (M1) 3.81 | (M2) 0.48 | — | 13.04 | 1.82 | 8.67 | 4.30 |
| 8 | (M1) 4.01 | (M4) 0.32 | — | 13.00 | 1.81 | 8.96 | 4.46 |
| 9 [Ref] | (M1) 3.96 | — | (C1) 0.31 | 12.90 | 1.80 | 8.84 | 4.44 |
| 10 [Ref] | (M1) 3.89 | (M2) 0.54 | — | 13.00 | 1.81 | 8.92 | 4.45 |
| 11 | (M1) 4.03 | (M3) 0.48 | — | 12.99 | 1.81 | 8.86 | 4.45 |
| 12 [Ref] | (M1) 3.94 | (M2) 0.50 | — | 12.97 | 1.79 | 8.94 | 4.48 |
| 13 | (M1) 3.95 | (M4) 0.48 | — | 13.00 | 1.80 | 9.17 | 4.55 |
| 14 [Ref] | (M1) 3.63 | — | (C1) 0.31 | 13.14 | 1.74 | 8.66 | 4.32 |
| 15 [Ref] | (M1) 3.94 | (M2) 0.50 | — | 12.97 | 1.79 | 8.94 | 4.48 |
| 16 | — | (M3) 2.19 | — | 13.12 | 1.82 | 8.76 | 4.33 |
| 17 [Ref] | (M1) 4.08 | — | (C1) 0.94 | 13.03 | 1.80 | 9.42 | 4.69 |
| 18 | (M1) 6.11 | (M5) 0.698 | — | 12.99 | 1.80 | 14.78 | 7.67 |
| 19 [Ref] | (M1) 3.78 | — | (C1) 0.31 | 13.60 | 1.80 | 7.78 | 4.55 |
| 20 | (M1) 3.94 | (M2) 0.50 | — | 12.97 | 1.79 | 8.94 | 4.48 |
| 21 | (M6) 5.06 | — | — | 12.72 | 1.82 | 8.59 | 4.69 |

TABLE 3

Polymer Attributes

| Example | Modifiers | Mw | Mn | Mp1 | CR (total) | Mooney Viscosity | Vinyl content | Styrene content |
|---|---|---|---|---|---|---|---|---|
| 1 [Ref] | (M1) | 484,829 | 318,559 | 312,273 | 25.9 | 67.8 | 62.0 | 21.4 |
| 2 [Ref] | (M1)/(M2) | 380,210 | 287,911 | 302,433 | 19.6 | 64.2 | 61.7 | 21.2 |
| 3 | (M3) | 462,267 | 356,796 | 295,559 | 55.9 | 90.6 | 62.4 | 21.6 |
| 4 [Ref] | (M1) | 484,829 | 318,559 | 312,273 | 25.9 | 67.8 | 62.0 | 21.4 |
| 5 [Ref] | (M1)/(M2) | 380,210 | 287911 | 302,433 | 19.6 | 64.2 | 61.7 | 21.2 |
| 6 | (M1)/(M3) | 381,320 | 306,514 | 305,267 | 23.0 | 68.2 | 61.7 | 21.9 |
| 7 [Ref] | (M1)/(M2) | 389,222 | 309,180 | 302,431 | 20.8 | 80.5 | 61.9 | 21.4 |
| 8 | (M1)/(M4) | 408,406 | 310,930 | 300,653 | 28.4 | 76.6 | 62.4 | 21.9 |
| 9 [Ref] | (M1) | 451,220 | 320,806 | 302,482 | 24.7 | 66.2 | 62.4 | 21.6 |
| 10 [Ref] | (M1)/(M2) | 389,652 | 315,780 | 301,575 | 22.8 | 68.2 | 62.6 | 21.7 |
| 11 | (M1)/(M3) | 460,255 | 358,101 | 303,391 | 49.4 | 97.0 | 62.6 | 21.5 |
| 12 [Ref] | (M1)/(M2) | 380,210 | 287,911 | 302433 | 19.6 | 65.7 | 61.7 | 21.2 |
| 13 | (M1)/(M4) | 417,860 | 324,620 | 295,767 | 36.8 | 79.5 | 62.2 | 21.9 |
| 14 [Ref] | (M1) | 515,847 | 343,195 | 325,852 | 28.5 | 75.2 | 62.0 | 21.3 |
| 15 [Ref] | (M1)/(M2) | 380,210 | 287,911 | 302,433 | 19.6 | 65.7 | 61.7 | 21.2 |
| 16 | (M3) | 462,567 | 356,796 | 295,559 | 55.9 | 96.0 | 62.4 | 21.6 |
| 17 [Ref] | (M1) | 343,607 | 276,855 | 276,609 | 22.63 | 63.6 | 62.9 | 21.3 |
| 18 | (M1)/(M5) | 476,621 | 379,142 | 178,314 | 86.9 | 63.9 | 64.4 | 21.2 |
| 19 [Ref] | (M1) | 474,591 | 314,376 | 312,886 | 26.22 | 68.5 | 62.6 | 21.1 |
| 20 [Ref] | (M1)/(M2) | 380,210 | 287911 | 302,433 | 19.6 | 65.7 | 61.7 | 21.2 |
| 21 | (M6) | 522,629 | 387,826 | 308,185 | 64.0 | 103.2 | 61.7 | 21.5 |

*NM = Not Measured

Polymer compositions were prepared by combining and compounding the constituents listed below Table 4, in a 350 cc Banbury mixer and vulcanized at 160° C. for 20 minutes. Vulcanization process data and physical properties for the each elastomeric composition example are provided in Tables 5, 6 and 7.

TABLE 4

Polymer Composition using polymers 9, 10, 11, 12, 13, 14, 15, 16, 19, 20 and 21.

| Constituent | Amount (phr) |
|---|---|
| Elastomeric polymer Example (styrene butadiene copolymer) | 100 |
| IRB 7 (international ref. carbon black, Sid Richardson) | 50 |
| Stearic acid | 1.5 |
| Zinc oxide | 3.0 |
| Softner (Enerdex 65) | 5.0 |
| Vulcanization Package: | |
| Sulfur | 1.75 |
| CBS (N-cyclohexyl-2-benzothiazylsulfenamid; Vulcacit CZ/EG, Bayer AG) | 1.0 |

TABLE 5

Vulcanization Process Data

| Example | Modifier | TS 1 [min] | TS 2 [min] | TC 50 [min] | TC 90 [min] | TC 95 [min] | Heat build up [° C.] |
|---|---|---|---|---|---|---|---|
| 14G [Ref] | (1) | 3.9 | 5.6 | 7.8 | 15.0 | 18.7 | 83.7 |
| 15G [Ref] | (1)/(2) | 4.2 | 5.6 | 7.3 | 13.4 | 16.9 | 82.6 |
| 16G | (1)/(3) | 4.8 | 6.1 | 7.8 | 14.3 | 17.8 | 85.5 |
| 9E [Ref] | (1) | 4.9 | 6.2 | 8.2 | 15.3 | 19.2 | NM |
| 10E [Ref] | (1)/(2) | 5.4 | 6.4 | 8.6 | 15.6 | 19.5 | NM |
| 11E | (3) | 5.2 | 6.8 | 9.0 | 16.1 | 20.0 | NM |
| 12F [Ref] | (1)/(2) | 4.2 | 5.6 | 7.4 | 14.0 | 17.6 | 86.1 |
| 13F | (1)/(4) | 4.2 | 5.7 | 7.5 | 13.8 | 17.5 | 85.5 |
| 19I | (1) | 4.8 | 6.5 | 8.7 | 15.6 | 19.2 | NM |
| 20I [Ref] | (1)/(2) | 4.3 | 5.9 | 7.9 | 15.1 | 18.9 | NM |
| 21I | (6) | 4.8 | 5.7 | 7.4 | 14.1 | 17.9 | NM |

*NM = Not Measured

TABLE 6

Carbon Black Containing Polymer Vulcanizate Composition Properties

| Ex. | Modifier | Elongation at break [%] | Tensile Strength [MPa] | Modulus 300 [MPa] | Tan δ at −10° C. | Tan δ at 0° C. | Tan δ at 60° C. |
|---|---|---|---|---|---|---|---|
| 14G [Ref] | (1) | 396 | 21.2 | 15.0 | 1.143 | 0.594 | 0.095 |
| 15G [Ref] | (1)/(2) | 367 | 19.9 | 16.2 | 1.147 | 0.650 | 0.086 |
| 16G | (1)/(3) | 377 | 20.1 | 15.0 | 1.199 | 0.653 | 0.085 |
| 9E [Ref] | (1) | 424 | 21.5 | 13.9 | 1.155 | 0.651 | 0.097 |
| 10E [Ref] | (1)/(2) | 384 | 19.1 | 13.5 | 1.244 | 0.655 | 0.090 |
| 11E | (3) | 324 | 15.2 | 14.1 | 1.258 | 0.650 | 0.086 |
| 12F [Ref] | (1)/(2) | 377 | 20.3 | 14.7 | 1.151 | 0.667 | 0.086 |
| 13F | (1)/(4) | 367 | 20.1 | 15.4 | 1.187 | 0.730 | 0.079 |
| 29I [Ref] | (1) | 336 | 18.0 | 15.6 | 1.284 | 0.646 | 0.080 |
| 20I [Ref] | (1)/(2) | 367 | 19.1 | 14.5 | 1.178 | 0.636 | 0.087 |
| 21I | (6) | 431 | 22.0 | 13.4 | 1.310 | 0.695 | 0.085 |

TABLE 7

Polymer and Carbon Black Containing Polymer Composition Mooney Viscosities

| Ex. | Modifier | Polymer Mooney [MU] | Compound Mooney [MU] | Compound Mooney − Mooney [MU] |
|---|---|---|---|---|
| 14G [Ref] | (1) | 75.2 | 96.2 | 46.0 |
| 15G [Ref] | (1)/(2) | 65.7 | 95.5 | 57.9 |
| 16G | (1)/(3) | 96.0 | 95.9 | 20.4 |
| 9E [Ref] | (1) | 66.2 | 115.9 | 49.6 |
| 10E [Ref] | (1)/(2) | 68.2 | 121.4 | 52.2 |
| 11E | (3) | 97.0 | 121.9 | 24.9 |
| 12F [Ref] | (1)/(2) | 65.7 | 122.9 | 57.2 |
| 13F | (1)/(4) | 79.5 | 129.3 | 49.8 |
| 19I [Ref] | (1) | 68.5 | 119.5 | 51.0 |
| 20I [Ref] | (1)/(2) | 65.7 | 123.0 | 58.8 |
| 21I | (6) | 103.2 | 112.3 | 9.1 |

Additional polymer compositions were prepared by combining and compounding the constituents listed below Table 8, in a 350 cc Banbury mixer and vulcanized at 160° C. for 20 minutes. Vulcanization process data and physical properties for the each elastomeric composition example are provided in Tables 9, 10 and 11.

TABLE 8

Polymer Composition using polymers 1, 2, 3, 4, 5, 6, 7 and 8.

| Constituent | Amount (phr) |
|---|---|
| Elastomeric polymer Example (styrene butadiene copolymer) | 80 |
| High cis 1,4-polybutadiene (Buna cis 132 - BSL GmbH) | 20 |
| Precipitated silica (Ultrasil 7000 GR, Degussa-Hüls AG) | 80 |
| Silane (NXT silane, Degussa AG) | 9.7 |
| Stearic acid | 1.0 |
| Antiozonant (Dusantox 6 PPD (N-(1,3-dimethyl-butyl)-N'-phenyl-p-phenyllendiamin) Duslo) | 2.0 |
| Zinc oxide | 2.5 |
| Ozone protecting wax (Anitlux 654, Rhein Chemie Rheinau GmbH) | 1.5 |
| Softener (aromatic oil, VivaTec 500) | 20 |

TABLE 8-continued

Polymer Composition using polymers 1, 2, 3, 4, 5, 6, 7 and 8.

| Constituent | Amount (phr) |
|---|---|
| Vulcanization Package: | |
| Sulfur | 1.4 |
| TBBS (N-tert.-butyl-2-benzothiazyl-sulfenamide, Lanxess, Rhein Chemie Rheinau GmbH) | 1.5 |
| DPG (diphenylguanidin, Vulkacit D, Lanxess Deutschland GmbH) | 1.5 |

TABLE 9

Vulcanization Process Data

| Example | Modifier | TS 1 [min] | TS 2 [min] | TC 50 [min] | TC 90 [min] | TC 95 [min] | Heat build up [° C.] |
|---|---|---|---|---|---|---|---|
| 1A [Ref] | (1) | 4.5 | 5.3 | 7.2 | 15.4 | 20.1 | 90.6 |
| 2A [Ref] | (1)/(2) | 4.5 | 5.3 | 7.1 | 15.5 | 20.1 | 95.5 |
| 3A | (3) | 4.0 | 4.9 | 6.7 | 14.7 | 19.6 | 88.4 |
| 4B [Ref] | (1) | 4.6 | 5.4 | 7.1 | 14.6 | 19.1 | 90.1 |
| 5B [Ref] | (1)/(2) | 4.0 | 5.0 | 6.7 | 14.2 | 18.9 | 84.5 |
| 6B | (1)/(3) | 4.5 | 5.3 | 6.9 | 14.5 | 19.2 | 87.7 |
| 7C [Ref] | (1)/(2) | 4.1 | 5.2 | 7.0 | 14.1 | 18.9 | 82.5 |
| 8C | (1)/(4) | 4.6 | 5.6 | 7.3 | 14.0 | 18.5 | 85.5 |

*NM = Not Measured

TABLE 10

Silica Containing Polymer Vulcanizate Composition Properties

| Ex. | Modifier | Elongation at break [%] | Tensile Strength [MPa] | Modulus 300 [MPa] | Tan δ at −10° C. | Tan δ at 0° C. | Tan δ at 60° C. |
|---|---|---|---|---|---|---|---|
| 1A [Ref] | (1) | 444 | 19.6 | 10.5 | 0.564 | 0.260 | 0.086 |
| 2A [Ref] | (1)/(2) | 457 | 18.8 | 9.9 | 0.548 | 0.276 | 0.098 |
| 3A | (3) | 418 | 18.7 | 11.0 | 0.571 | 0.252 | 0.083 |
| 4B [Ref] | (1) | 464 | 20.3 | 10.1 | 0.578 | 0.269 | 0.076 |
| 5B [Ref] | (1)/(2) | 411 | 19.7 | 12.4 | 0.569 | 0.255 | 0.074 |
| 6B | (1)/(3) | 481 | 21.0 | 10.0 | 0.607 | 0.281 | 0.082 |
| 7C [Ref] | (1)/(2) | 443 | 20.6 | 11.2 | 0.572 | 0.263 | 0.070 |
| 8C | (1)/(4) | 431 | 18.6 | 10.7 | 0.600 | 0.292 | 0.075 |

TABLE 11

Polymer and Silica Containing Polymer Composition Mooney Viscosities

| Ex. | Modifier | Polymer Mooney [MU] | Compound Mooney [MU] | Compound Mooney − Mooney [MU] |
|---|---|---|---|---|
| 1A [Ref] | (1) | 67.8 | 74.2 | 6.6 |
| 2A [Ref] | (1)/(2) | 64.2 | 69.8 | 5.6 |
| 3A | (3) | 90.6 | 80.1 | −10.5 |
| 4B [Ref] | (1) | 67.8 | 70.0 | 2.2 |
| 5B [Ref] | (1)/(2) | 64.2 | 78.8 | 14.6 |
| 6B | (1)/(3) | 74.1 | 73.8 | −0.3 |
| 7C [Ref] | (1)/(2) | 66.1 | 78.2 | 12.1 |
| 8C | (1)/(4) | 76.6 | 80.6 | 4.0 |

Additional polymer compositions were prepared by combining and compounding the constituents listed below Table 12, in a 350 cc Banbury mixer and vulcanized at 160° C. for 20 minutes. Vulcanization process data and physical properties for the each elastomeric composition example are provided in Tables 13, 14 and 15.

TABLE 12

Polymer Composition using 17 and 18.

| Constituent | Amount (phr) |
|---|---|
| Elastomeric polymer Example (styrene butadiene copolymer) | 80 |
| High cis 1,4-polybutadiene (Buna cis 132 - BSL GmbH) | 20 |
| Precipitated silica (Ultrasil 7000 GR, Degussa-Hüls AG) | 80 |
| Silane (NXT silane, Degussa AG) | 9.7 |
| Stearic acid | 1.0 |
| Antiozonant (Dusantox 6 PPD (N-(1,3-dimethyl-butyl)-N'-phenyl-p-phenyllendiamin) Duslo) | 2.0 |
| Zinc oxide | 2.5 |
| Ozone protecting wax (Anitlux 654, Rhein Chemie Rheinau GmbH) | 1.5 |
| Softener (aromatic oil, VivaTec 500) | 20 |
| Vulcanization Package: | |
| Sulfur | 1.4 |
| CBS (N-cyclohexyl-2-benzothiazylsulfenamid; Vulcacit CZ/EG, Bayer AG) | 1.5 |
| DPG (diphenylguanidin, Vulkacit D, Lanxess Deutschland GmbH) | 1.5 |

TABLE 13

Vulcanization Process Data

| Example | Modifier | TS 1 [min] | TS 2 [min] | TC 50 [min] | TC 90 [min] | TC 95 [min] | Heat build up [° C.] |
|---|---|---|---|---|---|---|---|
| 17H [Ref] | (1) | 3.7 | 4.4 | 6.1 | 15.5 | 20.7 | NM |
| 18H | (1)/(5) | 3.6 | 4.1 | 5.9 | 17.2 | 22.6 | NM |

*NM = Not Measured

TABLE 14

Silica Containing Polymer Vulcanizate Composition Properties

| Ex. | Modifier | Elongation at break [%] | Tensile Strength [MPa] | Modulus 300 [MPa] | Tan δ at −10° C. | Tan δ at 0° C. | Tan δ at 60° C. |
|---|---|---|---|---|---|---|---|
| 17H [Ref] | (1) | 425 | 16.6 | 9.4 | 0.536 | 0.265 | 0.105 |
| 18H | (1)/(5) | 452 | 17.1 | 9.7 | 0.492 | 0.274 | 0.141 |

TABLE 15

Polymer and Silica Containing Polymer Composition Mooney Viscosities

| Ex. | Modifier | Polymer Mooney [MU] | Compound Mooney [MU] | Compound Mooney − Mooney [MU] |
|---|---|---|---|---|
| 17H [Ref] | (1) | 63.6 | 65.7 | 2.1 |
| 18H | (1)/(5) | 63.9 | 54.8 | −9.1 |

It was found that silane sulfide modified macromolecular compounds of Formula P1, P2, P3, P4, P5 or P6, in combination with silane sulfide modification agents of Formula 1, including Formula 5 and Formula 6, optionally coupling agents and optionally further modification agent(s), preferably selected from those of Formula 7, form polymers which can be used for the preparation of elastomeric polymer compositions and vulcanized elastomeric polymer compositions.

The present invention provides (second) polymer compositions comprising silica and/or carbon black as well as silane sulfide modified macromolecular compound(s) which have a lower Mooney viscosity increase during mixing of the individual components as compared with corresponding polymer compositions not containing silane sulfide modified macromolecular compound(s). This either leads to reduced Mooney viscosities of the resulting second polymer compositions (Option 1) or allows the use of silane sulfide modified macromolecular compounds with higher Mooney viscosity when compared with reference polymers not containing the silane sulfide modification, to arrive at second polymer compositions with Mooney viscosities in a range similar to reference compositions not containing the silane sulfide modified macromolecular compounds (Option 2).

The reduced Mooney viscosity enables an increased mixing throughput or a reduction of the number of individual mixing steps and also enables an increased extrusion speed of the finalized polymer composition. Reference is made to example 18H in Table 15 (Mooney viscosity of 54.8 MU), including silane sulfide modified polymer 18 in Table 3 (Mooney viscosity of 63.9 MU), and comparative example 17H in Table 15 (Mooney viscosity of 65.7 MU), based on reference polymer 17 in Table 3 (63.6 MU).

In order to demonstrate the formation of the silane sulfide chain end-modification agents according to Formula 1, Formula 5 and Formula 6 the structures of silane sulfide chain end-modification agents M3, M4, M5 and M6 were confirmed by $^1$H- and $^{13}$C-NMR spectroscopy (as described above) and the method of preparation of M3, M4, M5 and M6 is described above. Subsequently, the silane sulfide chain end-modification agents formed were used for the preparation of polymers.

Along with above mentioned application properties it was surprisingly found that silane sulfide modification agents led to higher polymer chain coupling degrees than polymers modified with alternative (non-inventive) modification agents in equivalent concentrations. For example the inventive modified polymer 3 in Table 3, made by using subject silane sulfide chain end-modification agent M3, has a coupling degree of 55.9% of the total amount of living polymer chains respectively, while reference polymers 1 and 2 not being made by using subject modification agents resulted in coupling degrees of 24.9 and 19.6%. It is generally accepted that an increased polymer coupling degree leads to relatively reduced polymer solution viscosities if the weight average molecular weight (Mw) of the polymer or the corresponding solvent free polymer Mooney viscosity is kept constant. Beneficially in that case the productivity of the polymerization process and thus the polymer production throughput can be increased. Alternatively, it is generally accepted, that an increased polymer coupling degree enables the manufacturing of polymers of increased weight average molecular weight (Mw) or of increased solvent free polymer Mooney viscosity but identical polymer solution viscosity compared with polymers having a relatively lower coupling degree. Polymers of increased weight average molecular weight (Mw) or of high solvent free Mooney viscosity are usually more difficult to process in mechanical mixers, roll mills or during extrusion of filler-containing polymer compositions. Surprisingly, we found relatively reduced Mooney viscosities for silane sulfide modified macromolecular compounds when mixed with silica or carbon black. As discussed above, the conditions, for example the presence of water at elevated temperature, during mechanical mixing of silane sulfide modified macromolecular compounds with fillers, such as for example carbon black and silica, lead to the cleavage of Si—S and Sn—S bonds present in the silane-sulfide modified macromolecular compounds of the present invention. Therefore, silane sulfide modified macromolecular compounds having a relatively high coupling degree are transformed during mechanical mixing with fillers into silane sulfide modified macromolecular compounds having a relatively lower coupling degree and/or linear modified macromolecular compounds of relatively lower weight average molecular weight (Mw) or relatively lower Mooney viscosity value. Therefore, the processing of silane sulfide modified macromolecular compounds during formation of polymer-filler compositions in mechanical mixers, as well as roll milling or extrusion of polymer-filler compositions is significantly simplified, and the mixing, roll milling or extrusion throughput can be increased.

The macromolecular compounds of the invention are comprised in a first composition. The first compositions may be converted into "second polymer compositions" (first stage mixing and second stage mixing according to Tables 4, 8 and 12 by addition of carbon black or silica filler to the modified macromolecular compound of the invention), then further converted into a vulcanized polymer composition, which is formed, for example, if the second stage mixing result according to Tables 4, 8 and 12 is cured at 160° C. for 20 min. The second polymer compositions (as listed in Tables 5, 9 and 13) and the vulcanized polymer compositions (as listed in Tables 6, 10 and 14), which are prepared under identical conditions at the same day by the identical operator, are identified with a capital letter, e.g. A, B, etc. The polymer contained in the vulcanized polymer composition is reflected by the polymer number, e.g. 1, 2, etc. As result, there are vulcanized polymer composition series, such as 1A, 2A, 3A and 4A which can be directly compared with each other.

The second polymer compositions based on macromolecular compounds made by using silane sulfide modifiers of the invention (see example 16G and 11E in Table 7 and example 3A and 8C in Table 11) have relatively lower Mooney viscosity increase, calculated as the difference of the Mooney viscosity of the second polymer composition comprising silane sulfide modified macromolecular compound and carbon black (also referred to as Compound Mooney in Tables 7 and 11) and of the Mooney viscosity of the silane sulfide modified macromolecular compound (also referred to as Polymer Mooney), as compared to corresponding polymer compositions comprising silica or carbon black and with reference polymers not containing silane sulfide modified macromolecular compounds. The second polymer compositions according to examples 16G and 11E in Table 7 contain carbon black filler as shown in Table 4. More particular, the Mooney viscosity increase resulting from the addition of carbon black to a polymer was reduced by 25.6 or 37.5 Mooney units (MU), respectively, when reference polymers 14G or 15G were replaced by silane sulfide modified composition 16G. Furthermore, the Mooney viscosity increase which results when carbon black is added to a polymer was reduced by 24.7 or 27.3 MU, respectively, when reference polymers 9E or 10E were replaced by silane sulfide modified composition 11E. The second polymer compositions according to example 3A and 8C in Table 11 contain silica filler as shown in Table 8. The Mooney viscosity increase which results when silica is added to a polymer was reduced by 17.1 or 16.1 MU, respectively, when reference polymers 1A or 2A were replaced by silane sulfide modified polymer 3A. Furthermore, the Mooney viscosity increase which results when silica is added to a polymer was reduced by 6.1 MU, when reference polymer 7C was replaced by silane sulfide modified polymer 8C.

The use of silane sulfide modified macromolecular compounds, compared with reference polymers not containing the silane sulfide modification, enables the production of vulcanized polymer compositions according to Option 2 having at least one of the properties lower "Tan δ at 60° C." values, higher "Tan δ at 0° C." values and higher "Tan δ at −10° C." values improved, while the other properties are at a comparable level. The processes of the present invention, combining A) polymerization initiator compounds with B) a silane sulfide modifier, optionally C) coupling agents and optionally D) other modification agent, provides an increased degree of polymer modification and an improved performance.

The vulcanized carbon black-containing polymer compositions based on polymers made with the silane sulfide modifiers of the invention (see example 13F in Tables 5 and 6) have relatively lower (or reduced) values for tan δ at 60° C.; relatively higher (or increased) values for tan δ at 0° C.; relatively higher (or increased) values for tan δ at −10° C. and relatively decreased tire heat built up, as compared with an elastomeric vulcanized polymer composition based on other polymers (see example 12F in Tables 5 and 6). Exemplary vulcanized composition 13F, based on silane sulfide modified polymer 13, obtained with silane sulfide modifier M4 of the invention and with further modifier M1, has a heat built up value of 85.5° C., a tan δ value at 60° C. of 0.079, a tan δ value at 0° C. of 0.730 and a tan δ value at −10° C. of 1.187, while vulcanized composition 12F, based on non-modified polymer 12, based on non-inventive chain-end modifiers M1 and M2, has a relatively higher heat built up value of 86.1° C., a relatively higher tan δ value at 60° C. of 0.086, a relatively lower tan δ value at 0° C. of 0.667 and a relatively lower tan δ value at −10° C. of 1.151.

The vulcanized silica-containing polymer compositions based on polymers made with the silane sulfide modifier of the invention (see example 3A in Tables 9 and 10) have relatively higher (or increased) values for tan δ at −10° C. and relatively decreased tire heat built up, when compared with an elastomeric vulcanized polymer compositions based on other polymers (see example 1A and 2A in Tables 9 and 10). Exemplary vulcanized composition 3A, based on silane sulfide modified polymer 3, obtained with silane sulfide modifier M3 of the invention, has a heat built up value of 88.4° C., and a tan δ value at −10° C. of 0.571, while vulcanized compositions 1A and 2A, both based on non-modified polymers 1 and 2, modified with other modifier M1 or modifiers M1 and M2, have a relatively higher heat built up value of 90.6° C. and 95.5° C. and a relatively lower tan δ value at −10° C. of 0.564 and 0.548, respectively.

One particular application for the modified elastomeric polymers lies in the preparation of elastomeric polymer compositions, which again are specifically used for tire treads and which can have one or more of the following key characteristics: reduced viscosity increase during manufacture; reduced rolling resistance; relatively decreased tire heat built up; increased wet grip; increased ice skid.

The invention claimed is:
1. A silane sulfide modified elastomeric macromolecular compound obtainable by reacting
  i) a living anionic elastomeric polymer and
  ii) a silane sulfide modifier represented by the following Formula (5) or Formula (6):

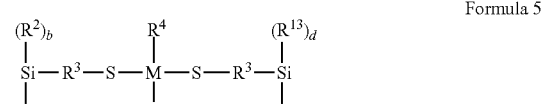

Formula 5

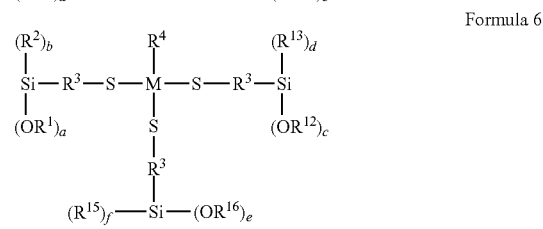

Formula 6 wherein
M is a silicon atom or a tin atom;
$R^3$ is at least divalent and is ($C_8$-$C_{16}$) alkylarylalkyl, ($C_7$-$C_{16}$) arylalkyl, ($C_7$-$C_{16}$) alkylaryl, or ($C_1$-$C_{16}$) alkyl, and each group may be substituted with one or more of the following groups: tertiary amine group, silyl group, ($C_7$-$C_{18}$) aralkyl group and ($C_6$-$C_{18}$) aryl group;
$R^1$, $R^{12}$ and $R^{16}$ are each independently selected from a hydrogen atom and ($C_1$-$C_4$) alkyl;

$R^2$, $R^{13}$ and $R^{15}$ are each independently selected from ($C_1$-$C_{16}$) alkyl, ($C_7$-$C_{16}$) alkylaryl and ($C_7$-$C_{16}$) arylalkyl;

$R^4$ and $R^{14}$ are each independently selected from ($C_1$-$C_{16}$) alkyl and ($C_7$-$C_{16}$) alkylaryl;

b, d and f are each independently selected from an integer of 0, 1 and 2; a, c and e are each independently selected from an integer of 1, 2 and 3; a+b=3; c+d=3; and e+f=3.

2. The silane sulfide modified elastomeric macromolecular compound according to claim 1, which is represented by the following Formula (P1)

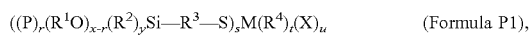  (Formula P1), wherein

P is a polymer chain comprising monomer units derived from at least one of the following monomer groups: butadiene, isoprene, styrene and alpha-methylstyrene, the number of monomer units per macromolecule ranging from 10 to 50.000;

M is a silicon atom or a tin atom;

x is an integer selected from 1, 2 and 3; y is an integer selected from 0, 1, and 2; r is an integer selected from 1, 2 and 3; wherein x+y+r=3;

s is an integer selected from 2, 3 and 4; t is an integer selected from 0, 1 and 2; u is an integer selected from 0, 1 and 2; wherein s+t+u=4;

$R^1$ is independently selected from a hydrogen atom and ($C_1$-$C_6$) alkyl;

$R^2$ is independently selected from ($C_1$-$C_{16}$) alkyl, ($C_7$-$C_{16}$) alkylaryl and ($C_7$-$C_{16}$) arylalkyl;

$R^3$ is at least divalent and is independently selected from ($C_1$-$C_{16}$)alkyl, ($C_8$-$C_{16}$) alkylarylalkyl, ($C_7$-$C_{16}$) arylalkyl and ($C_7$-$C_{16}$) alkylaryl, and each group may be substituted with one or more of the following groups: tertiary amine group, silyl group, ($C_7$-$C_{18}$) aralkyl group and ($C_6$-$C_{18}$) aryl group;

$R^4$ is independently selected from ($C_1$-$C_{16}$) alkyl and ($C_7$-$C_{16}$) alkylaryl; and X is independently selected from chloride, bromide and —$OR^5$; wherein $R^5$ is selected from ($C_1$-$C_{16}$) alkyl and ($C_7$-$C_{16}$) arylalkyl.

3. The silane sulfide modified elastomeric macromolecular compound according to claim 2, wherein $R^3$ is divalent ($C_1$-$C_{16}$) alkyl.

4. The silane sulfide modified elastomeric macromolecular compound according to claim 2, wherein X is selected from chloride, bromide and —$OR^5$; wherein $R^5$ is selected from ($C_1$-$C_{16}$) alkyl.

5. The silane sulfide modified elastomeric macromolecular compound according to claim 2, wherein $R^2$ and $R^4$ are independently selected from ($C_1$-$C_{16}$) alkyl.

6. The silane sulfide modified elastomeric macromolecular compound according to claim 2, wherein $R^1$, $R^2$, $R^4$ and $R^5$ are independently selected from ($C_1$-$C_4$) alkyl.

7. The silane sulfide modified elastomeric macromolecular compound according to claim 2, wherein s and t are each 2 and u is 0; or s is 3, t is 1 and u is 0.

8. The silane sulfide modified elastomeric macromolecular compound according to claim 2, wherein r is 1, x is 1 and y is 1; or r is 1, x is 0 and y is 2.

9. A polymer composition comprising at least one silane sulfide modified macromolecular compound as defined in claim 1 and one or more further components selected from components which are added to or formed as a result of the polymerization process used for making the modified macromolecular compound and components which remain after solvent removal from the polymerization process.

10. The polymer composition according to claim 9, which comprises at least one filler.

11. The polymer composition according to claim 10, wherein the filler is one or more selected from carbon black, silica, carbon-silica dual-phase-filler, clay, calcium carbonate, magnesium carbonate, lignin, and glass particles.

12. The polymer composition according to claim 11, wherein the filler comprises silica.

13. The polymer composition according to claim 11, wherein the filler comprises carbon black.

14. The polymer composition according to claim 9, which comprises a vulcanization agent.

15. The polymer composition according to claim 9, which comprises at least one polymer selected from the group consisting of polybutadiene, butadiene-styrene copolymers, butadiene-isoprene copolymers, polyisoprene and butadiene-styrene-isoprene terpolymers.

16. A vulcanized polymer composition comprising the reaction product of at least the following: at least one vulcanization agent; and the polymer composition as defined in claim 9.

17. A method for making a vulcanized polymer composition comprising reacting at least the following components: at least one vulcanization agent; and the polymer composition as defined in claim 9.

18. An article comprising at least one component formed from the vulcanized polymer composition as defined in claim 16.

19. The article according to claim 18, which is selected from the group consisting of a tire, a tire tread, a tire side wall, a tire carcass, a belt, a hose, a vibration damper, and a footwear component.

20. The silane sulfide modified elastomeric macromolecular compound according to claim 1, wherein $R^3$ is a ($C_1$-$C_{16}$) divalent alkyl group or ($C_8$-$C_{16}$) divalent alkylarylalkyl group.

21. The silane sulfide modified elastomeric macromolecular compound according to claim 1, wherein $R^3$ is selected from —$CH_2$—, —$(CH_2)_2$—, —$(CH_2)_3$—, —$(CH_2)_4$—, —$CH_2$—$C_6H_4$—$CH_2$— and —$C_6H_4$—$C(CH_3)_2$—$C_6H_4$—.

22. The silane sulfide modified elastomeric macromolecular compound according to claim 1, wherein $R^2$, $R^4$, $R^{13}$ and $R^{15}$ are each independently selected from ($C_1$-$C_{16}$) alkyl.

23. The silane sulfide modified elastomeric macromolecular compound according to claim 1, wherein M is a silicon atom; a, c and e are each an integer selected from 2 and 3; and b, d and f are each an integer selected from 0 and 1.

* * * * *